(12) United States Patent
Paris et al.

(10) Patent No.: US 12,232,730 B2
(45) Date of Patent: Feb. 25, 2025

(54) IMPLANTABLE FLOW CONNECTOR

(71) Applicant: TVA Medical, Inc., Franklin Lakes, NJ (US)

(72) Inventors: Michael Paris, Lansdale, PA (US); Adam Dakin, Fort Washington, PA (US); Todd Polk, Doylestown, PA (US); Mahesh Krishnamoorthy, Lansdale, PA (US); Jin Park, Parsippany, NJ (US); Michael Longo, Glenmoore, PA (US); Peter Hinchliffe, Campbell Hall, NY (US)

(73) Assignee: TVA Medical, Inc., Franklin Lakes, NJ (US)

( * ) Notice: Subject to any disclaimer, the term of this patent is extended or adjusted under 35 U.S.C. 154(b) by 1099 days.

(21) Appl. No.: 17/133,000

(22) Filed: Dec. 23, 2020

(65) Prior Publication Data
US 2021/0177420 A1   Jun. 17, 2021

Related U.S. Application Data

(60) Division of application No. 15/017,620, filed on Feb. 6, 2016, now Pat. No. 10,987,106, which is a
(Continued)

(51) Int. Cl.
*A61B 17/11* (2006.01)
*A61B 17/064* (2006.01)
(Continued)

(52) U.S. Cl.
CPC .......... *A61B 17/11* (2013.01); *A61B 17/0643* (2013.01); *A61B 17/0644* (2013.01);
(Continued)

(58) Field of Classification Search
CPC . A61B 17/11; A61B 17/0643; A61B 17/0644; A61B 17/12009;
(Continued)

(56) References Cited

U.S. PATENT DOCUMENTS 2,127,903 A   8/1938  Bowen
3,818,511 A   6/1974  Goldberg et al.
(Continued)

FOREIGN PATENT DOCUMENTS

EP   894475 A1   2/1999
JP   03018355 A   1/1991
(Continued)

OTHER PUBLICATIONS

"International Preliminary Report on Patentability," issued by The International Bureau of WIPO in connection with International Patent Application No. PCT/US2008/072166.
(Continued)

*Primary Examiner* — Philip R Wiest
(74) *Attorney, Agent, or Firm* — Dickinson Wright PLLC; Andrew D. Dorisio

(57) ABSTRACT

A method of implanting and securing an implantable flow connector in a body of a patient for providing communication of a first space within the body of the patient with a second space within the body of the patient. The method includes providing a flow connector having a lumen having a first orifice and a second orifice, inserting a retention device into the first space within the body, subsequently inserting the flow connector through an opening in the retention device so the second portion of the flow connector extends into the first space within the body and placing the second space within the body over the retention device.

20 Claims, 64 Drawing Sheets

Related U.S. Application Data continuation of application No. 13/792,012, filed on Mar. 9, 2013, now Pat. No. 9,282,967, which is a continuation-in-part of application No. 13/716,179, filed on Dec. 16, 2012, now Pat. No. 8,961,446, which is a continuation of application No. 12/185,811, filed on Aug. 4, 2008, now Pat. No. 8,366,651.

(60) Provisional application No. 61/624,375, filed on Apr. 15, 2012, provisional application No. 60/953,570, filed on Aug. 2, 2007.

(51) Int. Cl.
    *A61B 17/12*     (2006.01)
    *A61M 27/00*     (2006.01)

(52) U.S. Cl.
    CPC ............ *A61B 2017/1107* (2013.01); *A61B 2017/1135* (2013.01); *A61B 17/12009* (2013.01); *A61M 27/002* (2013.01)

(58) Field of Classification Search
    CPC .... A61B 2017/1107; A61B 2017/1135; A61M 27/002
    See application file for complete search history.

(56) References Cited

U.S. PATENT DOCUMENTS

| | | | |
|---|---|---|---|
| 3,974,835 | A | 8/1976 | Hardy |
| 4,352,358 | A | 10/1982 | Angelchik |
| 4,366,819 | A | 1/1983 | Kaster |
| 4,368,736 | A | 1/1983 | Kaster |
| 4,667,673 | A | 5/1987 | Li |
| 4,705,040 | A | 11/1987 | Mueller et al. |
| 4,744,364 | A | 5/1988 | Kensey |
| 4,787,386 | A | 11/1988 | Walsh et al. |
| 4,852,568 | A | 8/1989 | Kensey |
| 4,890,612 | A | 1/1990 | Kensey |
| 5,061,274 | A | 10/1991 | Kensey |
| 5,108,421 | A | 4/1992 | Fowler |
| 5,141,516 | A | 8/1992 | Detweiler |
| 5,156,619 | A | 10/1992 | Ehrenfeld |
| 5,192,302 | A | 3/1993 | Kensey et al. |
| 5,197,976 | A | 3/1993 | Herweck et al. |
| 5,222,974 | A | 6/1993 | Kensey et al. |
| 5,282,827 | A | 2/1994 | Kensey et al. |
| 5,330,445 | A | 7/1994 | Haaga |
| 5,453,090 | A | 9/1995 | Martinez et al. |
| 5,456,714 | A | 10/1995 | Owen |
| 5,503,635 | A | 4/1996 | Sauer et al. |
| 5,549,633 | A | 8/1996 | Evans et al. |
| 5,586,987 | A | 12/1996 | Fahy |
| 5,620,461 | A | 4/1997 | Muijs Van De Moer et al. |
| 5,634,936 | A | 6/1997 | Linden et al. |
| 5,643,340 | A | 7/1997 | Nunokawa |
| 5,649,959 | A | 7/1997 | Hannam et al. |
| 5,669,924 | A | 9/1997 | Shaknovich |
| 5,676,670 | A | 10/1997 | Kim |
| 5,683,451 | A | 11/1997 | Lenker et al. |
| 5,702,414 | A | 12/1997 | Richter et al. |
| 5,716,325 | A | 2/1998 | Bonutti |
| 5,728,134 | A | 3/1998 | Barak |
| 5,755,778 | A | 5/1998 | Kleshinski |
| 5,796,178 | A | 8/1998 | Onuma |
| 5,797,934 | A | 8/1998 | Rygaard |
| 5,817,113 | A | 10/1998 | Gifford et al. |
| 5,830,222 | A | 11/1998 | Makower |
| 5,853,422 | A | 12/1998 | Huebsch et al. |
| 5,868,697 | A | 2/1999 | Richter et al. |
| 5,868,761 | A | 2/1999 | Nicholas et al. |
| 5,868,763 | A | 2/1999 | Spence et al. |
| 5,868,777 | A | 2/1999 | Lam |
| 5,893,886 | A | 4/1999 | Zegdi et al. |
| 5,921,995 | A | 7/1999 | Kleshinski |
| 5,922,022 | A | 7/1999 | Nash et al. |
| 6,007,544 | A | 12/1999 | Kim |
| 6,007,576 | A * | 12/1999 | McClellan .............. A61F 2/064 623/23.71 |
| 6,017,352 | A | 1/2000 | Nash et al. |
| 6,019,788 | A | 2/2000 | Butters et al. |
| 6,030,395 | A | 2/2000 | Nash et al. |
| 6,036,702 | A | 3/2000 | Bachinski et al. |
| 6,036,703 | A | 3/2000 | Evans et al. |
| 6,036,705 | A | 3/2000 | Nash et al. |
| 6,056,762 | A | 5/2000 | Nash et al. |
| 6,063,114 | A | 5/2000 | Nash et al. |
| 6,068,638 | A | 5/2000 | Makower |
| 6,068,654 | A | 5/2000 | Berg et al. |
| 6,071,297 | A | 6/2000 | Salahieh et al. |
| 6,077,291 | A | 6/2000 | Das |
| 6,113,612 | A | 9/2000 | Swanson et al. |
| 6,117,145 | A | 9/2000 | Wood et al. |
| 6,149,681 | A | 11/2000 | Houser et al. |
| 6,152,937 | A | 11/2000 | Peterson et al. |
| 6,152,945 | A | 11/2000 | Bachinski et al. |
| 6,165,185 | A | 12/2000 | Shennib et al. |
| 6,171,329 | B1 | 1/2001 | Shaw et al. |
| 6,176,864 | B1 | 1/2001 | Chapman |
| 6,190,353 | B1 | 2/2001 | Makower et al. |
| 6,190,397 | B1 | 2/2001 | Spence et al. |
| 6,193,734 | B1 | 2/2001 | Bolduc et al. |
| 6,203,513 | B1 | 3/2001 | Yaron et al. |
| 6,206,893 | B1 | 3/2001 | Klein et al. |
| 6,206,913 | B1 | 3/2001 | Yencho et al. |
| 6,214,022 | B1 | 4/2001 | Taylor et al. |
| 6,214,029 | B1 | 4/2001 | Thill et al. |
| 6,217,585 | B1 | 4/2001 | Houser et al. |
| 6,231,587 | B1 | 5/2001 | Makower |
| 6,241,741 | B1 | 6/2001 | Duhaylongsod et al. |
| 6,241,768 | B1 | 6/2001 | Agarwal et al. |
| 6,251,116 | B1 | 6/2001 | Shennib et al. |
| 6,254,630 | B1 | 7/2001 | Inoue |
| 6,270,515 | B1 | 8/2001 | Linden et al. |
| 6,283,983 | B1 | 9/2001 | Makower et al. |
| 6,293,955 | B1 | 9/2001 | Houser et al. |
| 6,302,905 | B1 | 10/2001 | Goldsteen et al. |
| 6,350,280 | B1 | 2/2002 | Nash et al. |
| 6,371,965 | B2 | 4/2002 | Gifford et al. |
| 6,391,038 | B2 | 5/2002 | Vargas et al. |
| 6,395,015 | B1 | 5/2002 | Borst et al. |
| 6,395,019 | B2 | 5/2002 | Chobotov |
| 6,398,797 | B2 | 6/2002 | Bombard et al. |
| 6,402,764 | B1 | 6/2002 | Hendricksen et al. |
| 6,402,767 | B1 | 6/2002 | Nash et al. |
| 6,409,739 | B1 | 6/2002 | Nobles et al. |
| 6,419,681 | B1 | 7/2002 | Vargas et al. |
| 6,428,550 | B1 | 8/2002 | Vargas et al. |
| 6,440,163 | B1 | 8/2002 | Swanson et al. |
| 6,443,965 | B1 | 9/2002 | Gifford et al. |
| 6,451,048 | B1 | 9/2002 | Berg et al. |
| 6,458,140 | B2 | 10/2002 | Akin et al. |
| 6,461,320 | B1 | 10/2002 | Yencho et al. |
| 6,464,709 | B2 | 10/2002 | Shennib et al. |
| 6,471,713 | B1 | 10/2002 | Vargas et al. |
| 6,478,817 | B2 | 11/2002 | Schmitt et al. |
| 6,485,496 | B1 | 11/2002 | Suyker et al. |
| 6,485,513 | B1 | 11/2002 | Fan |
| 6,494,889 | B1 | 12/2002 | Fleischman et al. |
| 6,497,710 | B2 | 12/2002 | Yencho et al. |
| 6,508,824 | B1 | 1/2003 | Flaherty et al. |
| 6,517,558 | B2 | 2/2003 | Gittings et al. |
| 6,537,287 | B1 | 3/2003 | Yencho et al. |
| 6,537,288 | B2 | 3/2003 | Vargas et al. |
| 6,554,764 | B1 | 4/2003 | Vargas et al. |
| 6,565,581 | B1 | 5/2003 | Spence et al. |
| 6,582,463 | B1 | 6/2003 | Mowry et al. |
| 6,585,762 | B1 | 7/2003 | Stanish |
| 6,589,277 | B1 | 7/2003 | Fabiani et al. |
| 6,589,278 | B1 | 7/2003 | Harris et al. |
| 6,599,302 | B2 | 7/2003 | Houser et al. |
| 6,602,263 | B1 | 8/2003 | Swanson et al. |
| 6,616,675 | B1 | 9/2003 | Evard et al. |
| 6,620,129 | B2 | 9/2003 | Stecker et al. |

(56) References Cited

U.S. PATENT DOCUMENTS

| | | |
|---|---|---|
| 6,626,920 B2 | 9/2003 | Whayne |
| 6,626,939 B1 | 9/2003 | Burnside et al. |
| 6,648,900 B2 | 11/2003 | Fleischman et al. |
| 6,648,901 B2 | 11/2003 | Fleischman et al. |
| 6,652,543 B2 | 11/2003 | Spence et al. |
| 6,655,386 B1 | 12/2003 | Makower et al. |
| 6,673,085 B1 | 1/2004 | Berg |
| 6,695,875 B2 | 2/2004 | Stelter et al. |
| 6,699,257 B2 | 3/2004 | Gifford et al. |
| 6,702,828 B2 | 3/2004 | Whayne |
| 6,709,441 B2 | 3/2004 | Bolduc et al. |
| 6,712,831 B1 | 3/2004 | Kaplan et al. |
| 6,719,769 B2 | 4/2004 | Donohoe et al. |
| 6,719,781 B1 | 4/2004 | Kim |
| 6,726,697 B2 | 4/2004 | Nicholas et al. |
| 6,736,825 B2 | 5/2004 | Blatter et al. |
| 6,740,101 B2 | 5/2004 | Houser et al. |
| 6,743,243 B1 | 6/2004 | Roy et al. |
| 6,776,785 B1 | 8/2004 | Yencho et al. |
| 6,786,914 B1 | 9/2004 | Vargas et al. |
| 6,790,229 B1 | 9/2004 | Berreklouw |
| 6,821,286 B1 | 11/2004 | Carranza et al. |
| 6,858,035 B2 | 2/2005 | Whayne |
| 6,866,674 B2 | 3/2005 | Galdonik et al. |
| 6,869,437 B1 | 3/2005 | Hausen et al. |
| 6,893,449 B2 | 5/2005 | Vargas et al. |
| 6,905,504 B1 | 6/2005 | Vargas |
| 6,911,042 B2 | 6/2005 | Weadock |
| 6,913,607 B2 | 7/2005 | Ainsworth et al. |
| 6,913,609 B2 | 7/2005 | Yencho et al. |
| 6,916,327 B2 | 7/2005 | Northrup, III et al. |
| 6,926,690 B2 | 8/2005 | Renati |
| 6,926,724 B1 | 8/2005 | Chu |
| 6,942,675 B1 | 9/2005 | Vargas |
| 6,962,596 B2 | 11/2005 | Bolduc et al. |
| 6,972,023 B2 * | 12/2005 | Whayne ............... A61B 17/064 606/151 |
| 7,008,436 B2 | 3/2006 | Barath |
| 7,018,388 B2 | 3/2006 | Yencho et al. |
| 7,025,773 B2 | 4/2006 | Gittings et al. |
| 7,029,482 B1 | 4/2006 | Vargas et al. |
| 7,041,110 B2 | 5/2006 | Yencho et al. |
| 7,041,112 B2 | 5/2006 | Vargas et al. |
| 7,063,711 B1 | 6/2006 | Loshakove et al. |
| 7,063,712 B2 | 6/2006 | Vargas et al. |
| 7,128,749 B1 | 10/2006 | Vargas et al. |
| 7,160,311 B2 | 1/2007 | Blatter et al. |
| 7,172,608 B2 | 2/2007 | Vargas et al. |
| 7,175,637 B2 | 2/2007 | Vargas et al. |
| 7,182,771 B1 * | 2/2007 | Houser ............... A61B 17/11 623/1.36 |
| 7,270,670 B1 | 9/2007 | Yencho |
| 7,285,131 B1 | 10/2007 | Bombard et al. |
| 7,291,157 B1 | 11/2007 | Hausen et al. |
| 7,300,444 B1 | 11/2007 | Nielsen et al. |
| 7,303,569 B2 | 12/2007 | Yencho et al. |
| 7,303,570 B2 | 12/2007 | Bombard et al. |
| 7,309,343 B2 | 12/2007 | Vargas et al. |
| 7,351,247 B2 | 4/2008 | Kupiecki et al. |
| 7,371,243 B1 | 5/2008 | Nielsen et al. |
| 7,427,261 B1 | 9/2008 | Carranza et al. |
| 7,666,197 B2 | 2/2010 | Orban, III |
| 7,766,924 B1 | 8/2010 | Bombard et al. |
| 7,794,471 B1 | 9/2010 | Bender et al. |
| 7,892,246 B2 | 2/2011 | Akin et al. |
| 7,892,247 B2 | 2/2011 | Conston et al. |
| 7,922,733 B2 | 4/2011 | Borghi |
| 8,052,741 B2 | 11/2011 | Bruszewski et al. |
| 8,105,345 B2 | 1/2012 | Golden et al. |
| 8,142,387 B2 | 3/2012 | Heise et al. |
| 8,182,494 B1 | 5/2012 | Yencho et al. |
| 8,353,920 B2 | 1/2013 | Mikkaichi |
| 8,353,921 B2 | 1/2013 | Schaller et al. |
| 8,361,092 B1 * | 1/2013 | Asfora ............... A61B 17/08 623/1.23 |
| 8,366,651 B2 | 2/2013 | Dakin et al. |
| 8,690,816 B2 | 4/2014 | Dakin et al. |
| 8,961,446 B2 | 2/2015 | Dakin et al. |
| 9,282,967 B2 * | 3/2016 | Paris ............... A61B 17/0643 |
| 9,345,485 B2 | 5/2016 | Dakin et al. |
| 10,434,293 B2 * | 10/2019 | Park ............... A61M 1/3655 |
| 2001/0004699 A1 | 6/2001 | Gittings et al. |
| 2001/0047165 A1 | 11/2001 | Makower et al. |
| 2001/0049539 A1 | 12/2001 | Rehil |
| 2002/0022853 A1 | 2/2002 | Swanson et al. |
| 2002/0029079 A1 | 3/2002 | Kim et al. |
| 2002/0032462 A1 | 3/2002 | Houser et al. |
| 2002/0091398 A1 | 7/2002 | Galdonik et al. |
| 2003/0028205 A1 | 2/2003 | Vargas et al. |
| 2003/0065344 A1 | 4/2003 | Kirsch et al. |
| 2003/0100920 A1 | 5/2003 | Akin et al. |
| 2003/0212418 A1 | 11/2003 | Yencho et al. |
| 2003/0225425 A1 | 12/2003 | Kupiecki et al. |
| 2003/0229365 A1 | 12/2003 | Whayne et al. |
| 2003/0236518 A1 | 12/2003 | Marchitto et al. |
| 2003/0236542 A1 | 12/2003 | Makower |
| 2004/0024345 A1 | 2/2004 | Gharib et al. |
| 2004/0044349 A1 | 3/2004 | Barry et al. |
| 2004/0049212 A1 | 3/2004 | Whayne |
| 2004/0073282 A1 | 4/2004 | Stanish |
| 2004/0087984 A1 | 5/2004 | Kupiecki et al. |
| 2004/0087985 A1 | 5/2004 | Loshakove et al. |
| 2004/0088042 A1 | 5/2004 | Kim et al. |
| 2004/0092975 A1 | 5/2004 | Loshakove et al. |
| 2004/0097991 A1 | 5/2004 | Vargas et al. |
| 2004/0102796 A1 | 5/2004 | Hill et al. |
| 2004/0122318 A1 | 6/2004 | Flaherty et al. |
| 2004/0133225 A1 | 7/2004 | Makower |
| 2004/0158143 A1 | 8/2004 | Flaherty et al. |
| 2004/0158267 A1 | 8/2004 | Sancoff et al. |
| 2004/0249400 A1 | 12/2004 | Vargas et al. |
| 2004/0249415 A1 | 12/2004 | Vargas et al. |
| 2004/0260318 A1 | 12/2004 | Hunter et al. |
| 2005/0033329 A1 | 2/2005 | Bombard et al. |
| 2005/0043751 A1 | 2/2005 | Phan et al. |
| 2005/0043752 A1 | 2/2005 | Phan et al. |
| 2005/0137614 A1 | 6/2005 | Porter et al. |
| 2005/0149073 A1 | 7/2005 | Arani et al. |
| 2005/0165426 A1 | 7/2005 | Manzo |
| 2005/0192604 A1 | 9/2005 | Carson et al. |
| 2005/0251163 A1 | 11/2005 | Tilson et al. |
| 2005/0251180 A1 | 11/2005 | Burton et al. |
| 2005/0251187 A1 | 11/2005 | Beane et al. |
| 2006/0025788 A1 | 2/2006 | Loshakove et al. |
| 2006/0064119 A9 | 3/2006 | Tilson et al. |
| 2006/0241342 A1 | 10/2006 | Macaulay et al. |
| 2007/0005128 A1 | 1/2007 | Scholz et al. |
| 2007/0027526 A1 | 2/2007 | Demetriades et al. |
| 2007/0156079 A1 | 7/2007 | Brown |
| 2007/0282245 A1 | 12/2007 | Tu et al. |
| 2008/0009889 A1 | 1/2008 | Pokorney et al. |
| 2008/0009936 A1 | 1/2008 | Kim et al. |
| 2008/0109069 A1 | 5/2008 | Coleman et al. |
| 2008/0262604 A1 | 10/2008 | Stengel |
| 2009/0036817 A1 | 2/2009 | Dakin et al. |
| 2009/0036820 A1 | 2/2009 | Dakin et al. |
| 2009/0076531 A1 | 3/2009 | Richardson et al. |
| 2009/0143793 A1 | 6/2009 | Chua et al. |
| 2010/0130995 A1 | 5/2010 | Yevzlin et al. |
| 2011/0118764 A1 | 5/2011 | Beane et al. |
| 2011/0184329 A1 | 7/2011 | Kramer et al. |
| 2012/0065652 A1 | 3/2012 | Cully et al. |
| 2012/0123451 A1 | 5/2012 | Asfora et al. |
| 2013/0158462 A1 | 6/2013 | Wardle et al. |
| 2016/0096008 A1 | 4/2016 | Park et al. |
| 2016/0151066 A1 | 6/2016 | Paris et al. |

FOREIGN PATENT DOCUMENTS

| | | |
|---|---|---|
| JP | 97511409 | 11/2001 |
| JP | 2003220065 A | 8/2003 |
| WO | 9014796 A1 | 12/1990 |
| WO | 9514442 A1 | 6/1995 |
| WO | 9636377 A1 | 11/1996 |

(56) References Cited

FOREIGN PATENT DOCUMENTS

| WO | 9727898 A1 | 8/1997 |
|----|------------|--------|
| WO | 9731590 A1 | 9/1997 |
| WO | 9802099 A1 | 1/1998 |
| WO | 9807399 A1 | 2/1998 |
| WO | 9816174 A1 | 4/1998 |
| WO | 9819629 A2 | 5/1998 |
| WO | 9819636 A2 | 5/1998 |
| WO | 9840036 A1 | 9/1998 |
| WO | 9852471 A1 | 11/1998 |
| WO | 9852474 A1 | 11/1998 |
| WO | 9852495 A1 | 11/1998 |
| WO | 9908603 A1 | 2/1999 |
| WO | 9911180 A1 | 3/1999 |
| WO | 9948427 A1 | 9/1999 |
| WO | 0027310 A2 | 5/2000 |
| WO | 0027313 A2 | 5/2000 |
| WO | 0041633 A1 | 7/2000 |
| WO | 0049951 A1 | 8/2000 |
| WO | 0053104 A1 | 9/2000 |
| WO | 0069365 A2 | 11/2000 |
| WO | 0117440 A1 | 3/2001 |
| WO | 0139672 A2 | 6/2001 |
| WO | 0141653 A2 | 6/2001 |
| WO | 0178801 A2 | 10/2001 |
| WO | 02058591 A3 | 3/2003 |

OTHER PUBLICATIONS

"International Preliminary Report on Patentability," issued by The International Bureau of WIPO in connection with International Patent Application No. PCT/US2008/072167.

The extended European search report for application No. 08782616.0 or PCT/US2008/072166 dated Jun. 5, 2015.

The extended European search report for application No. 08782617.8 or PCT/US2008/072167 dated Jun. 10, 2015.

"International Search Report and Written Opinion," issued by The International Bureau ofWIPO in connection with International Patent Application No. PCT/US2011/052159.

International Search Report and Written Opinion issued by the International Bureau of WIPO in connection with International Patent Application No. PCT/US2013/0033629 dated Oct. 1, 2013.

\* cited by examiner

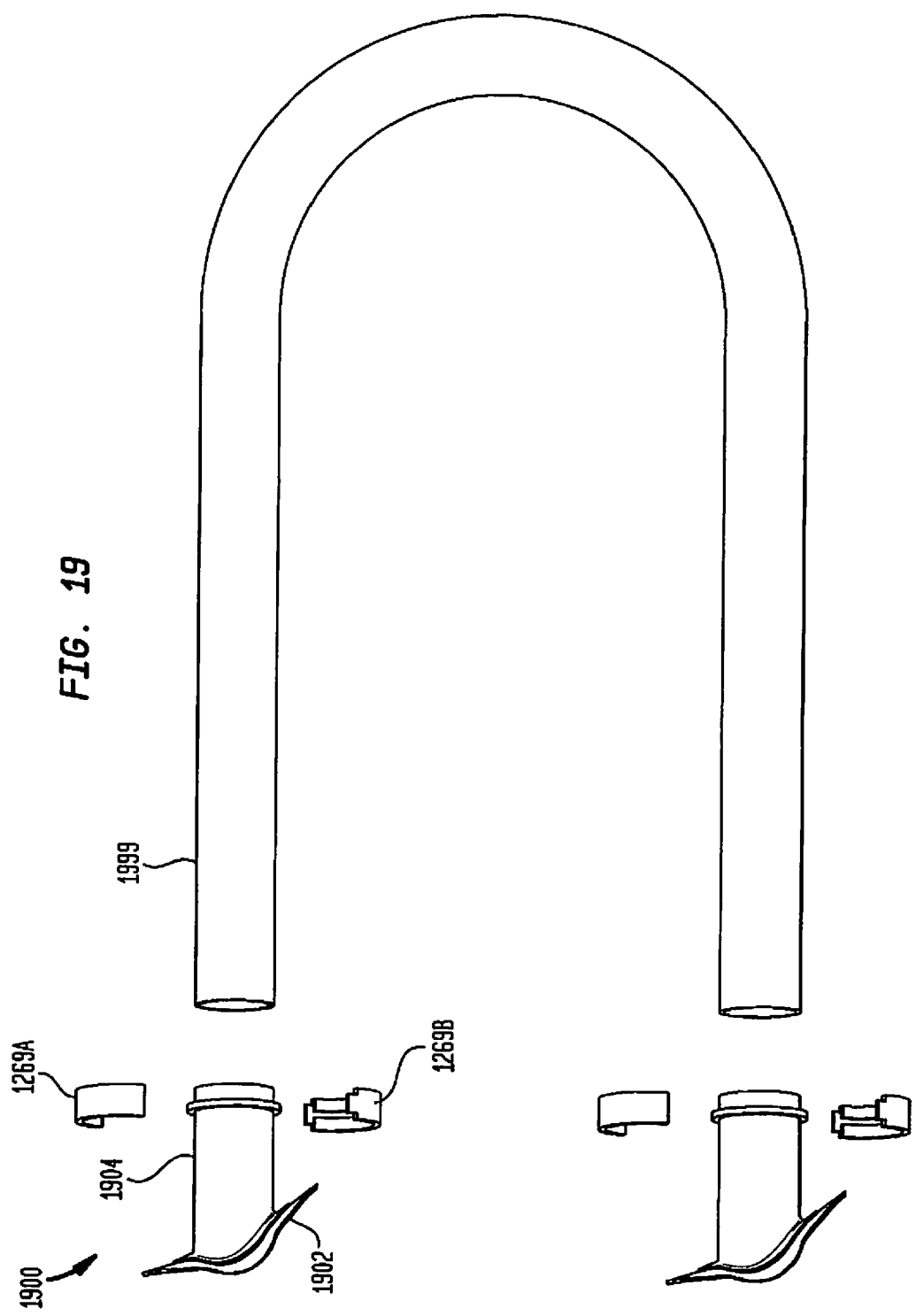

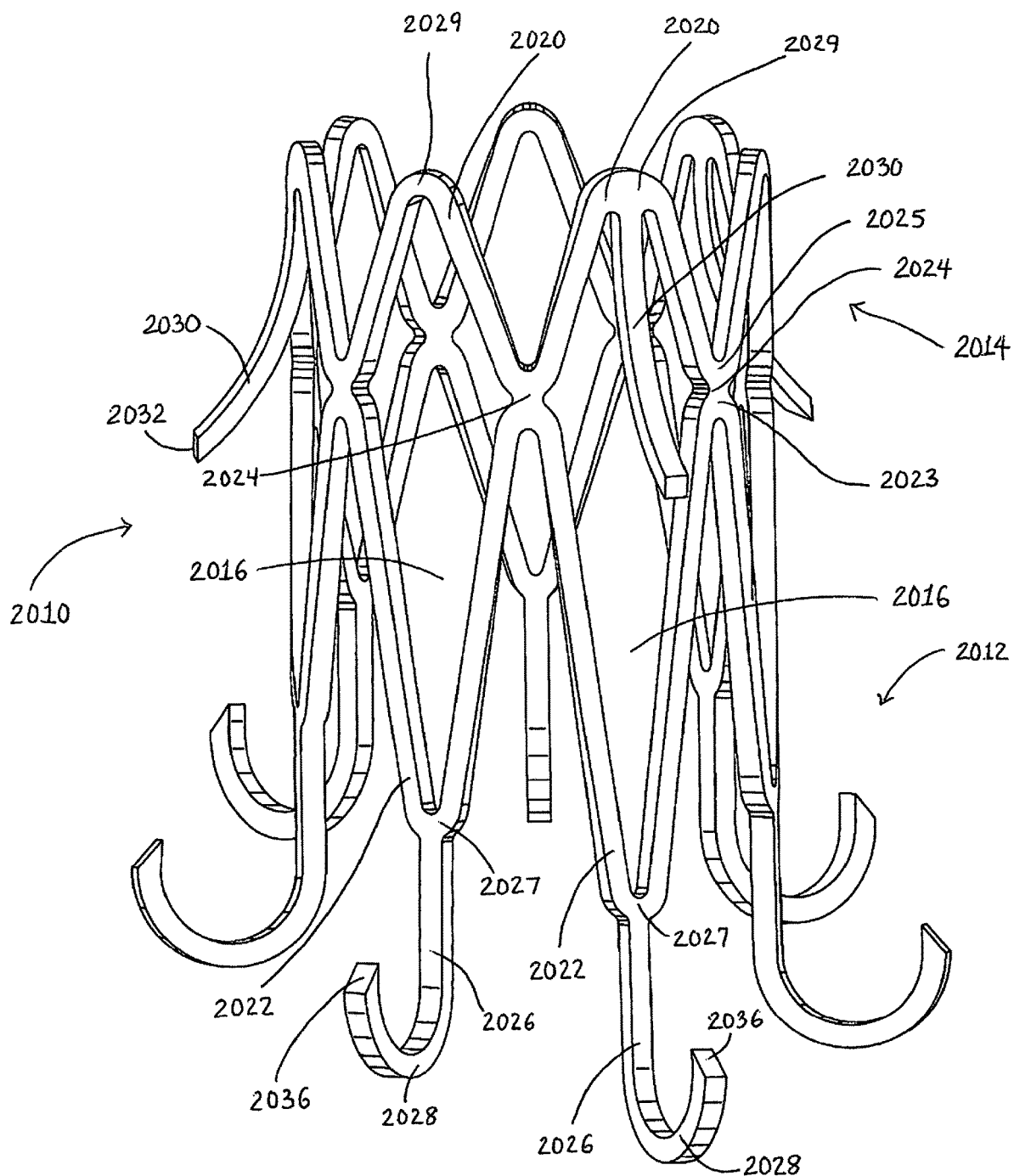
FIG_20

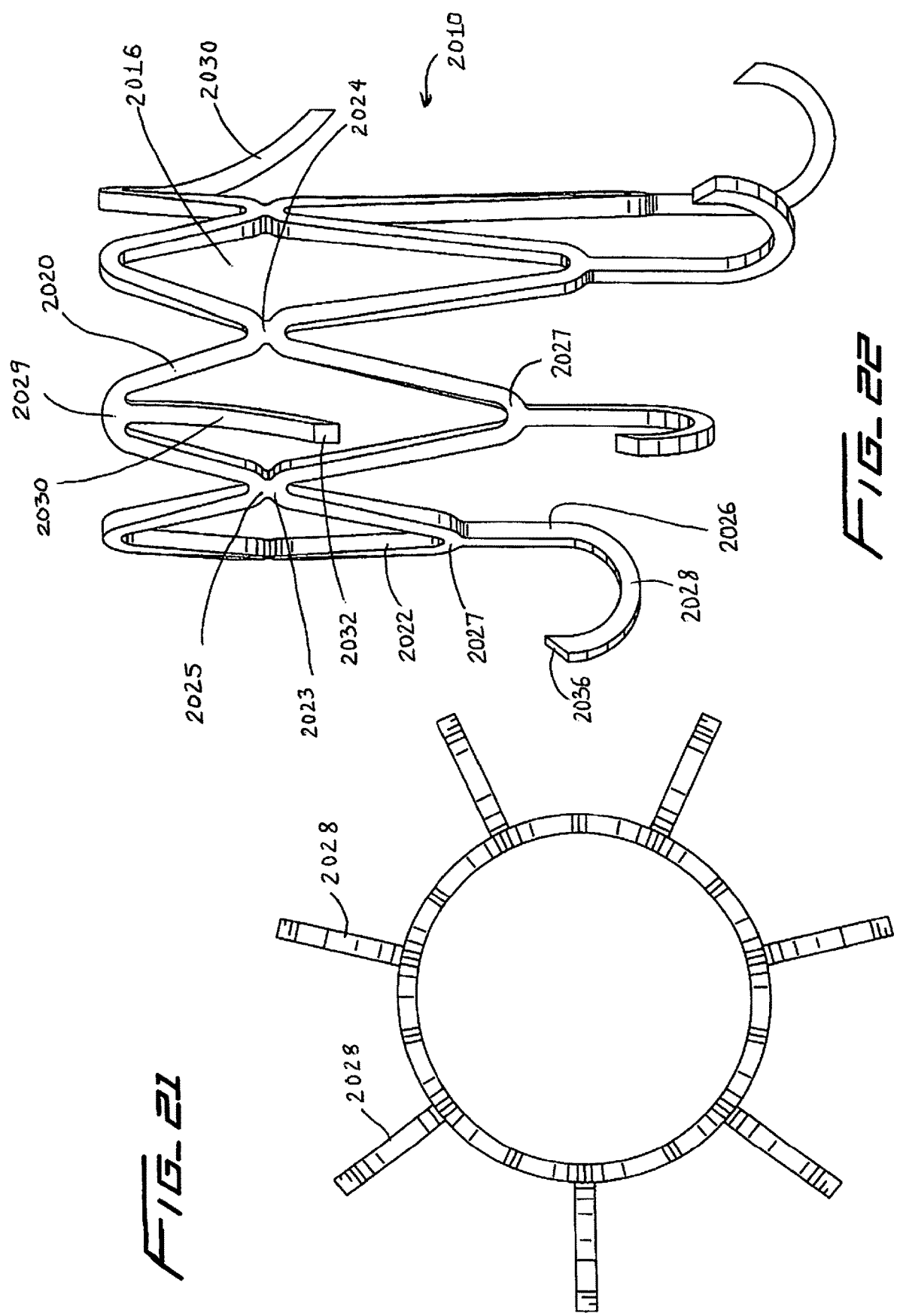

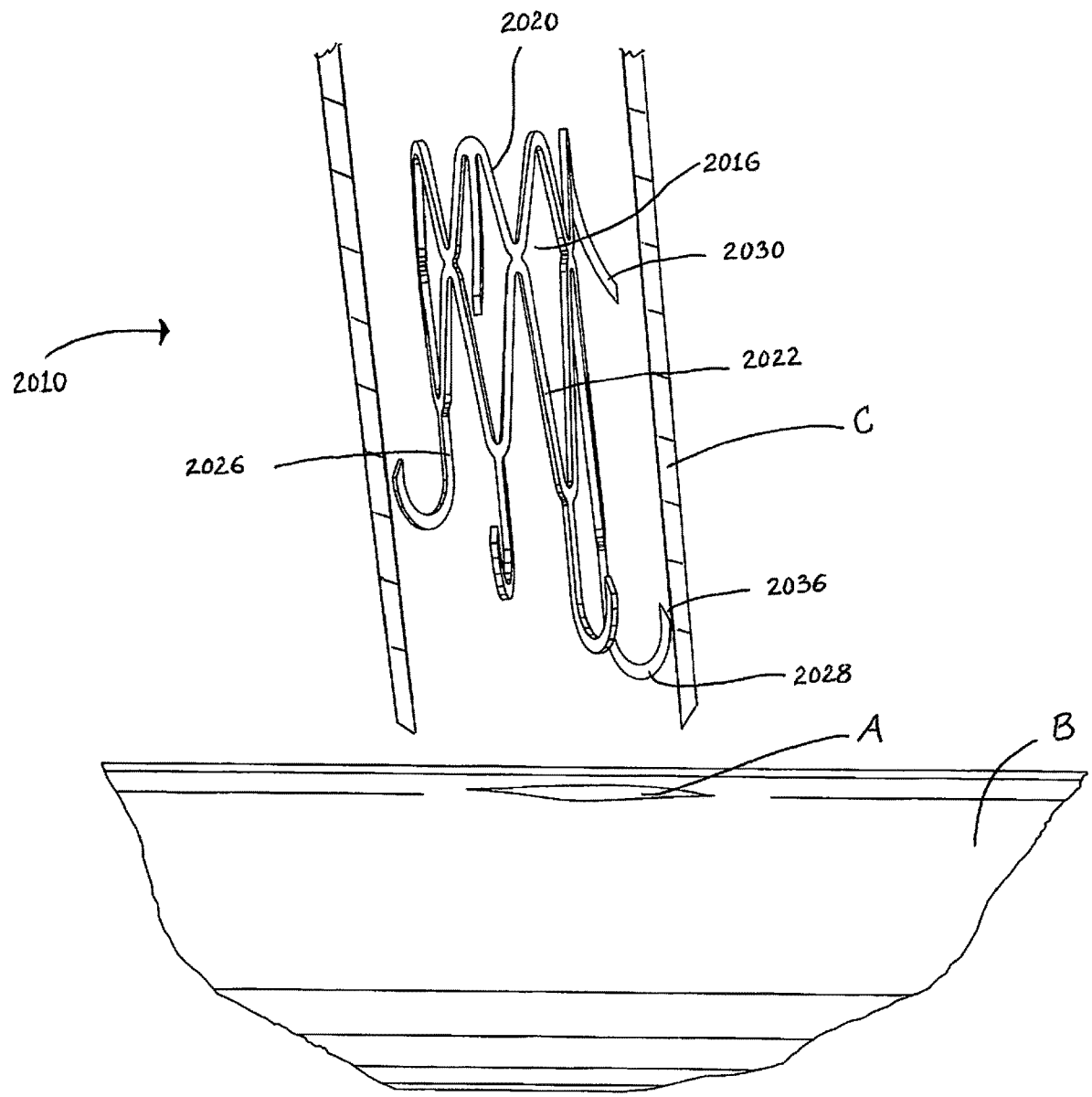
FIG_23

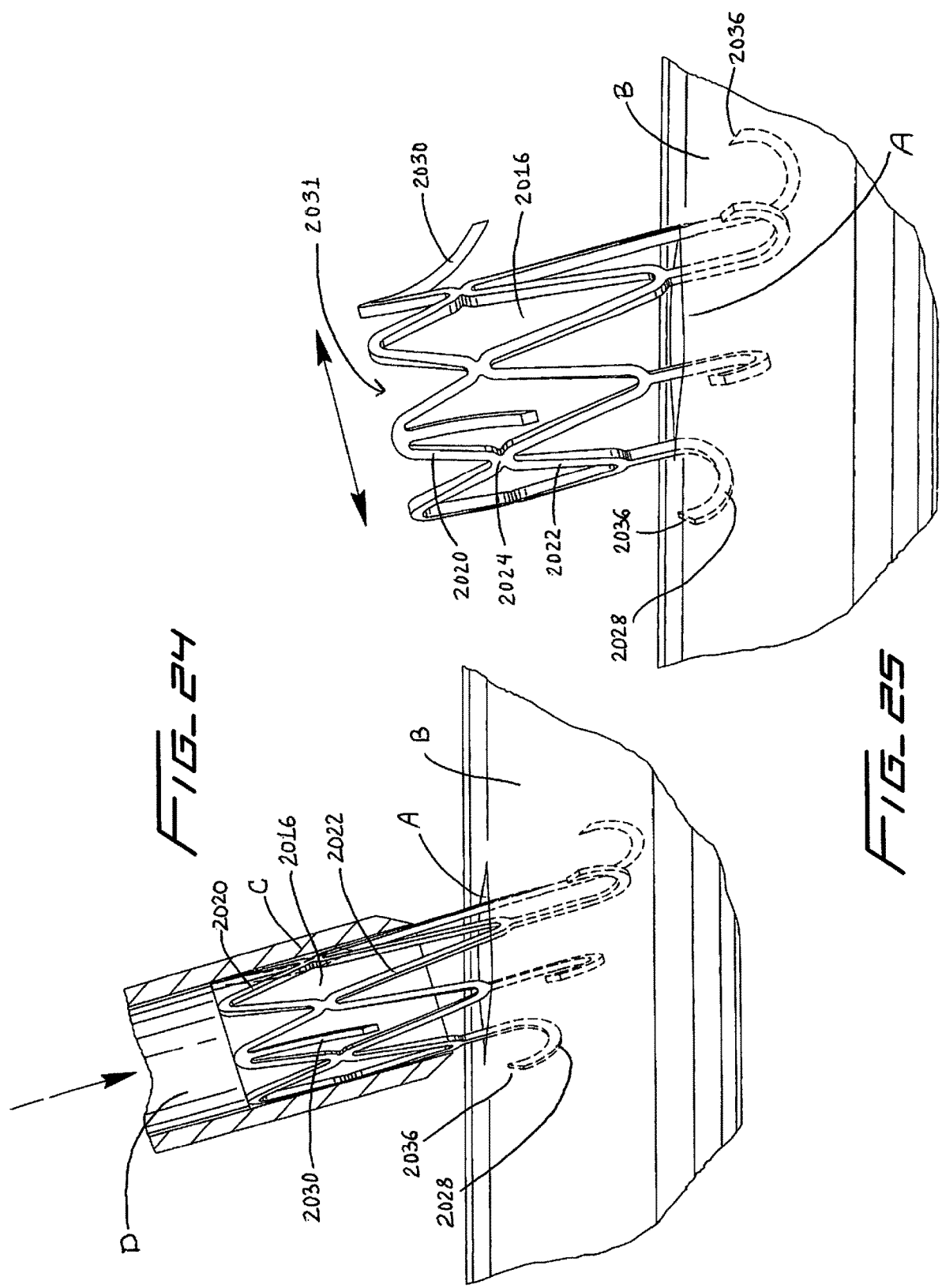

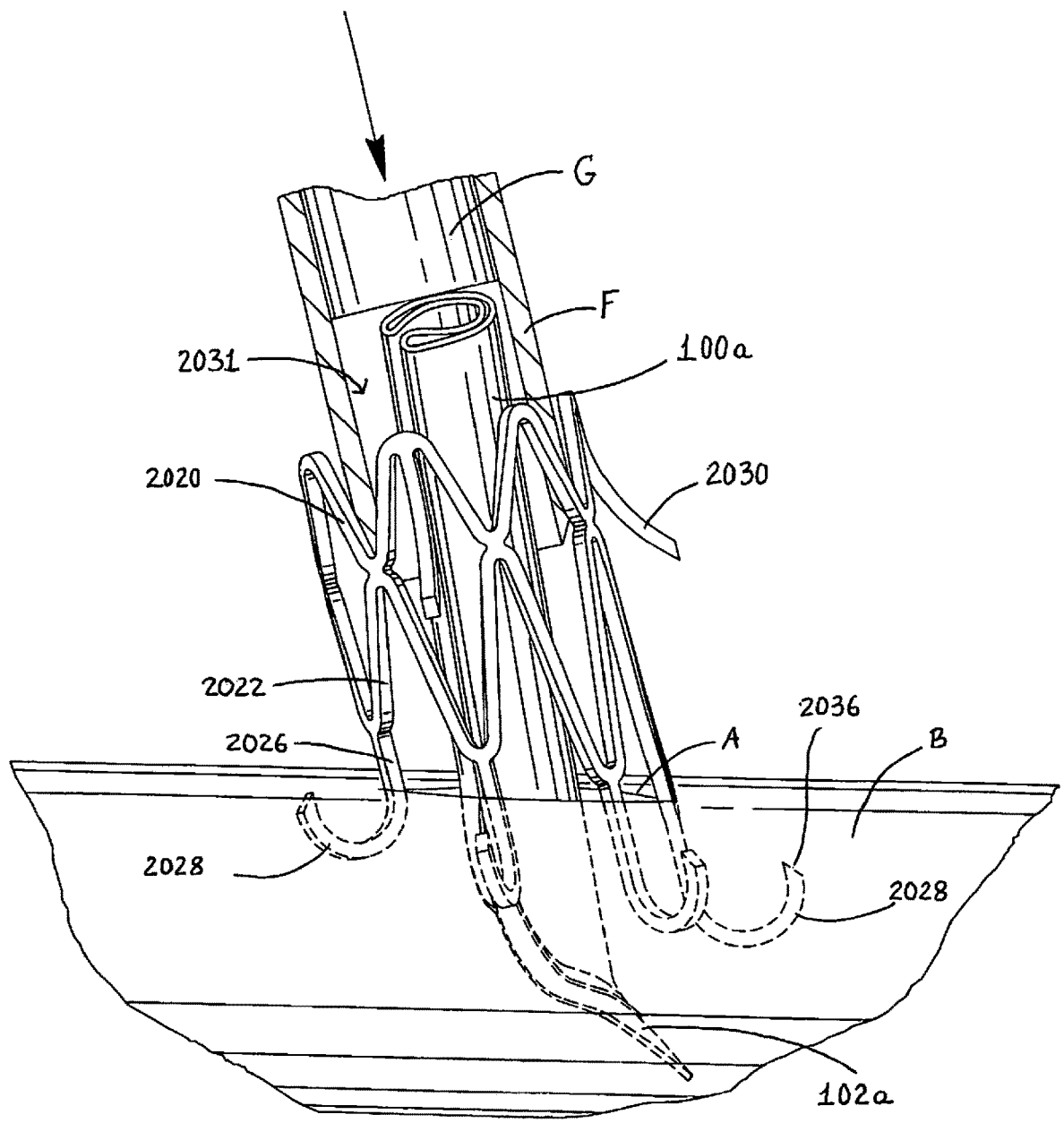

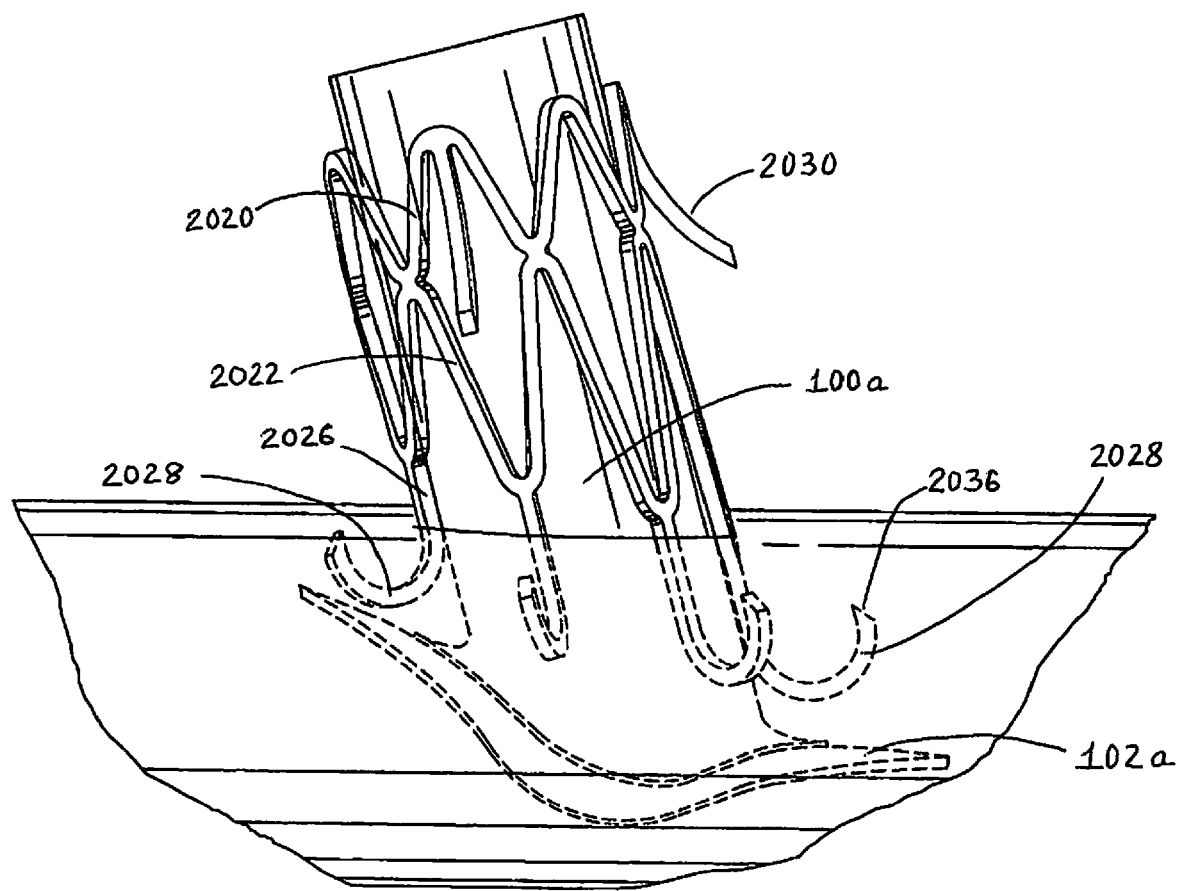
FIG_27

FIG_31

FIG_34

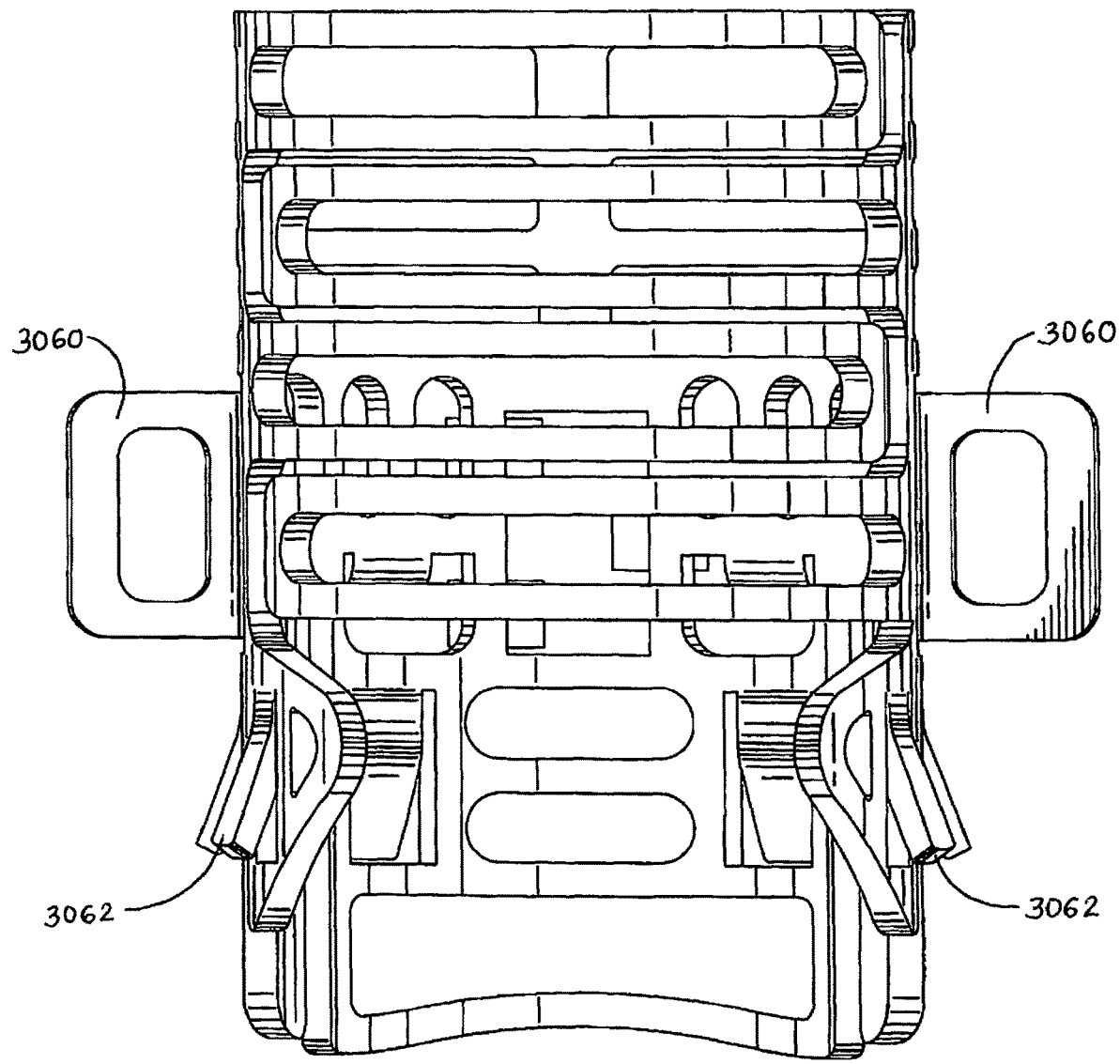
FIG_36

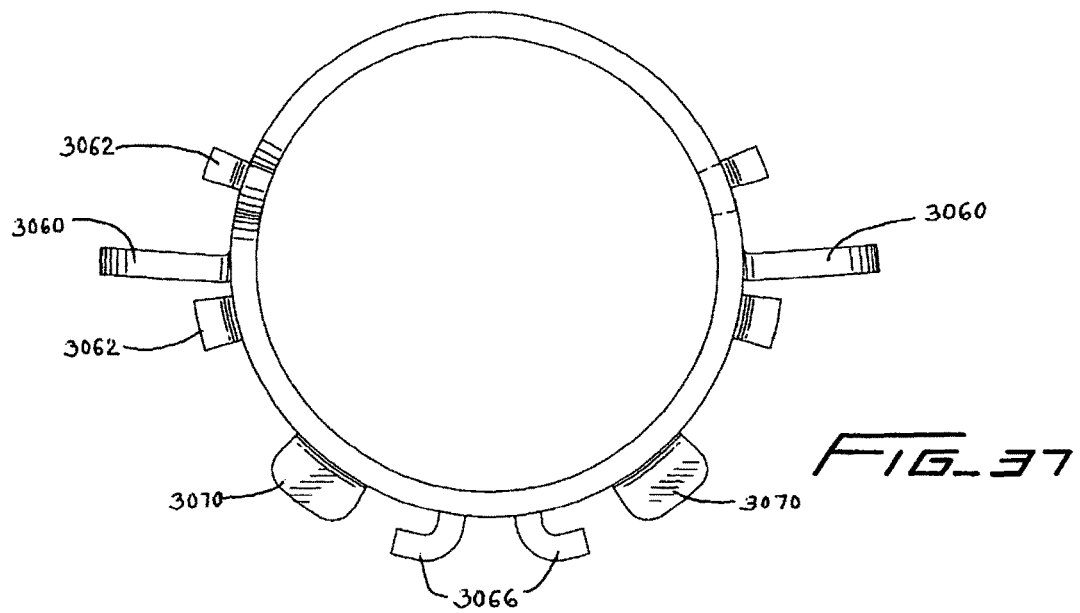
FIG_37
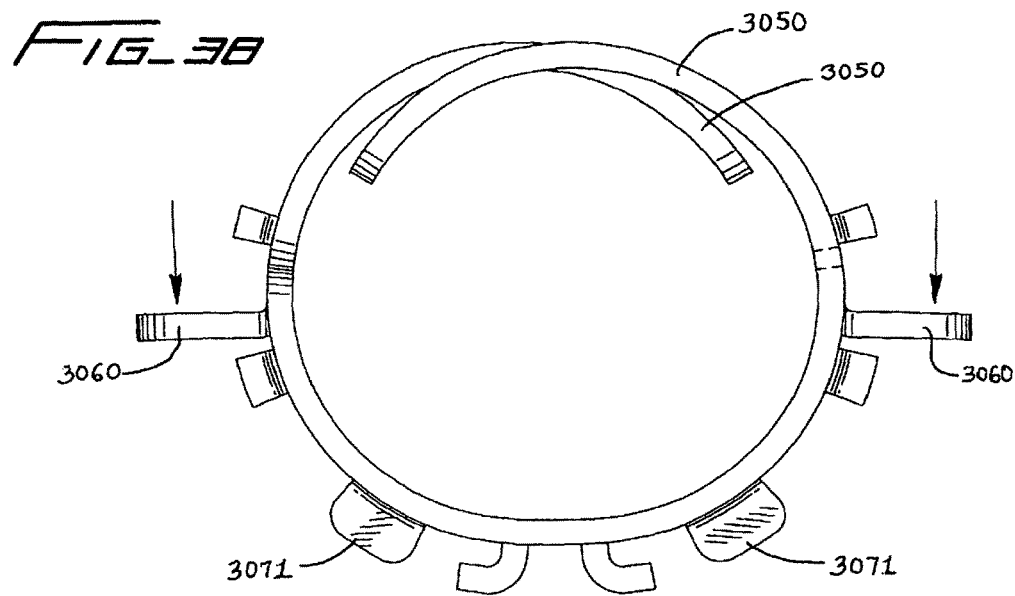
FIG_38

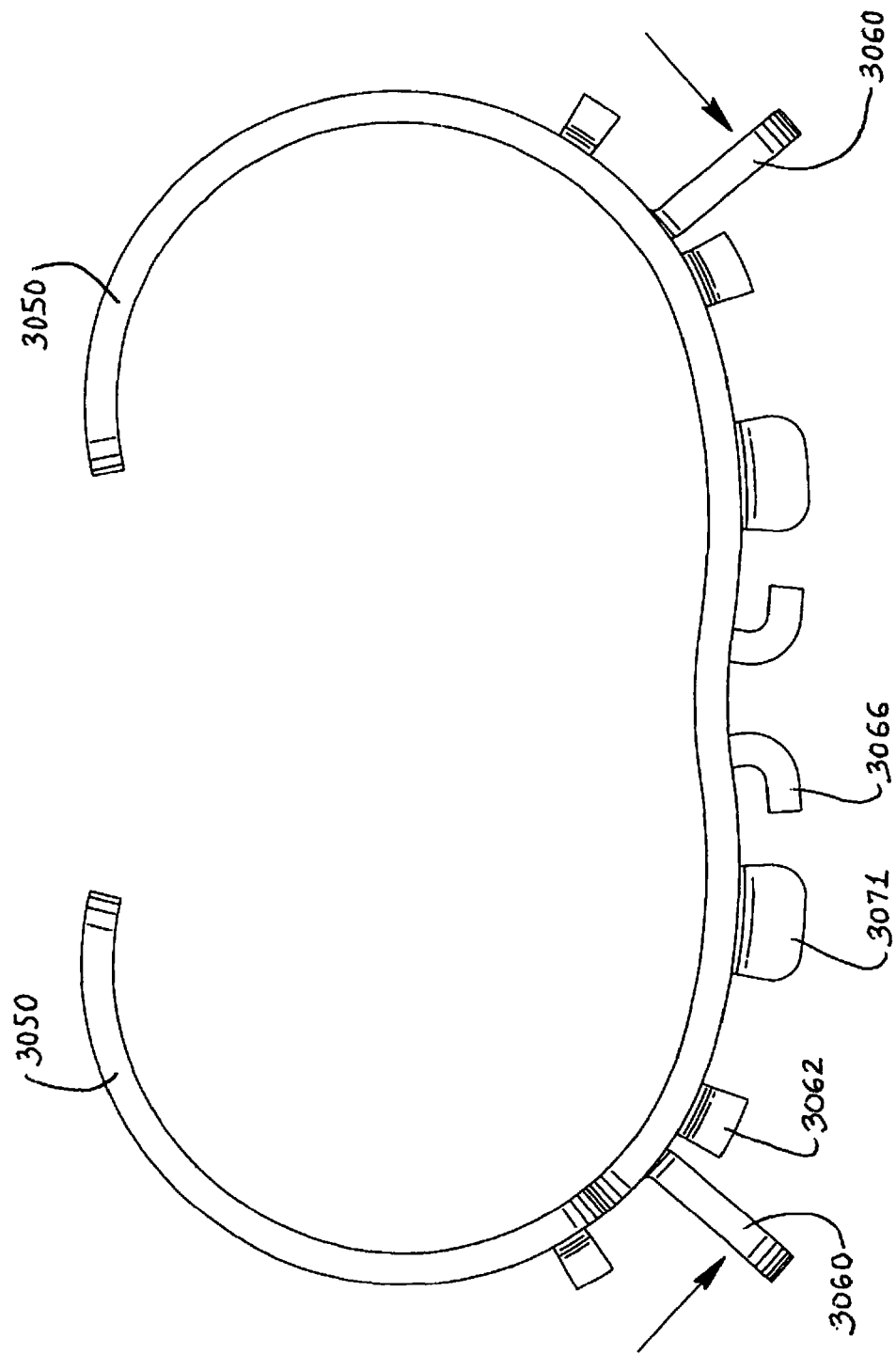

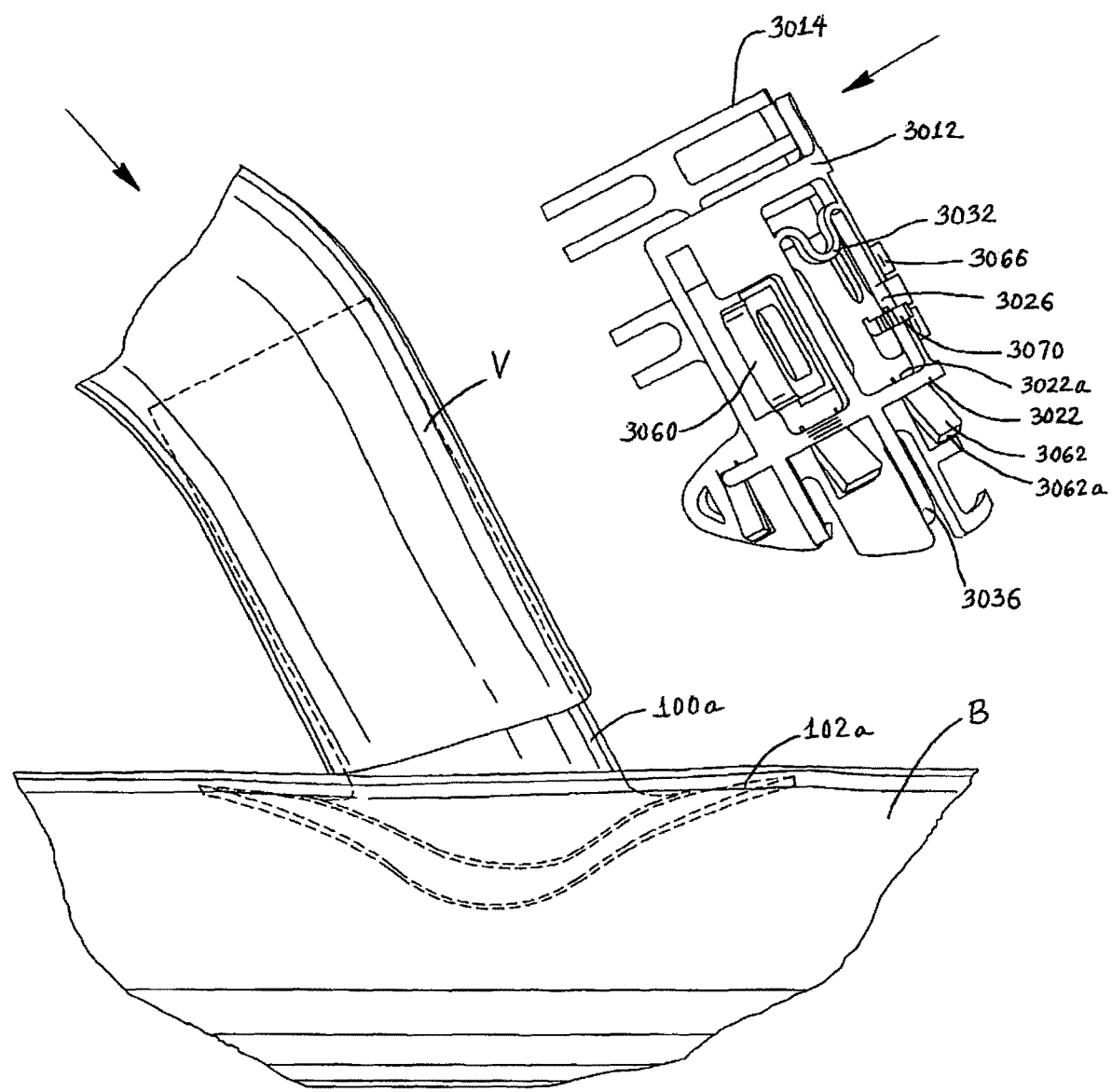

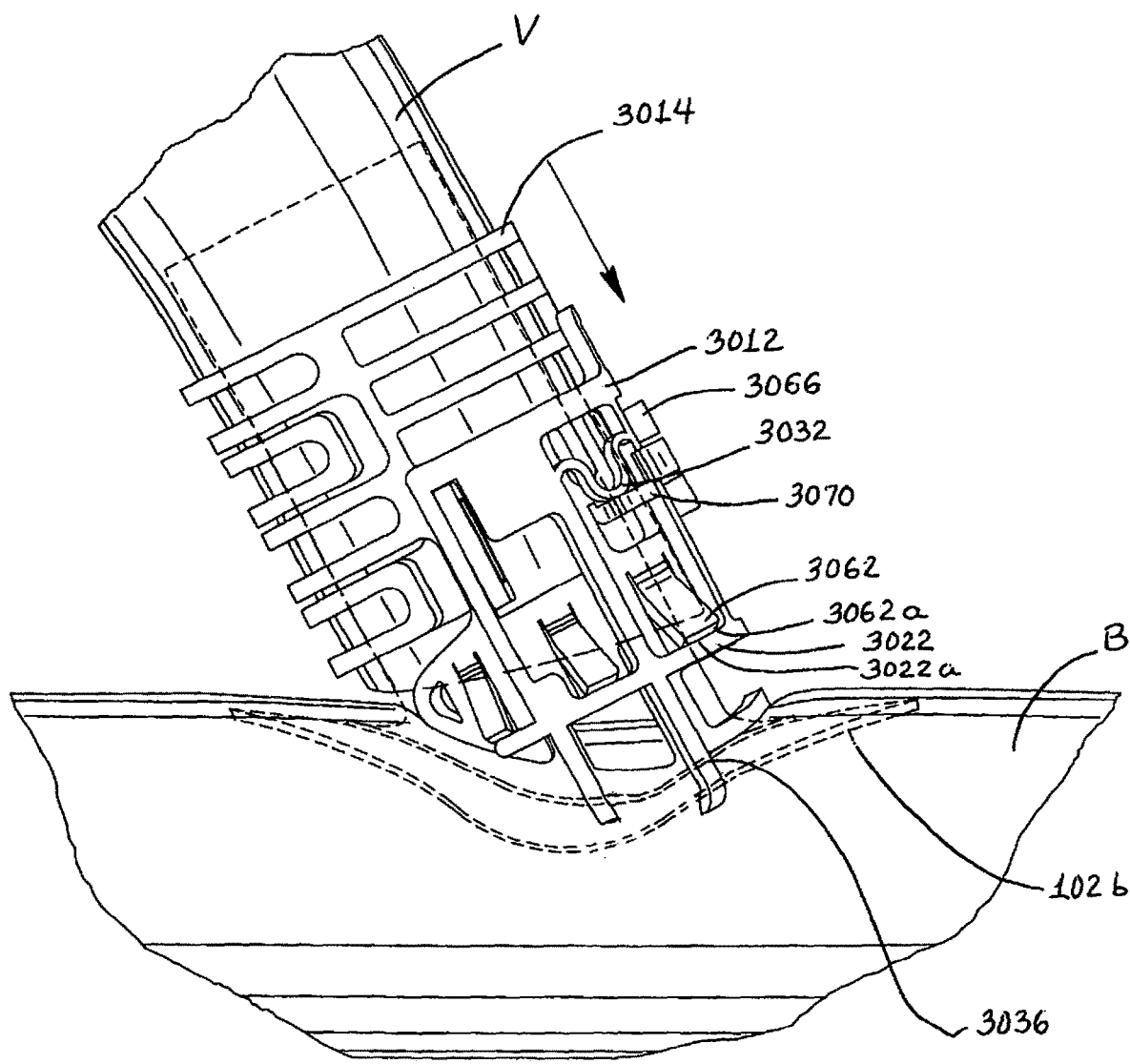
FIG_41

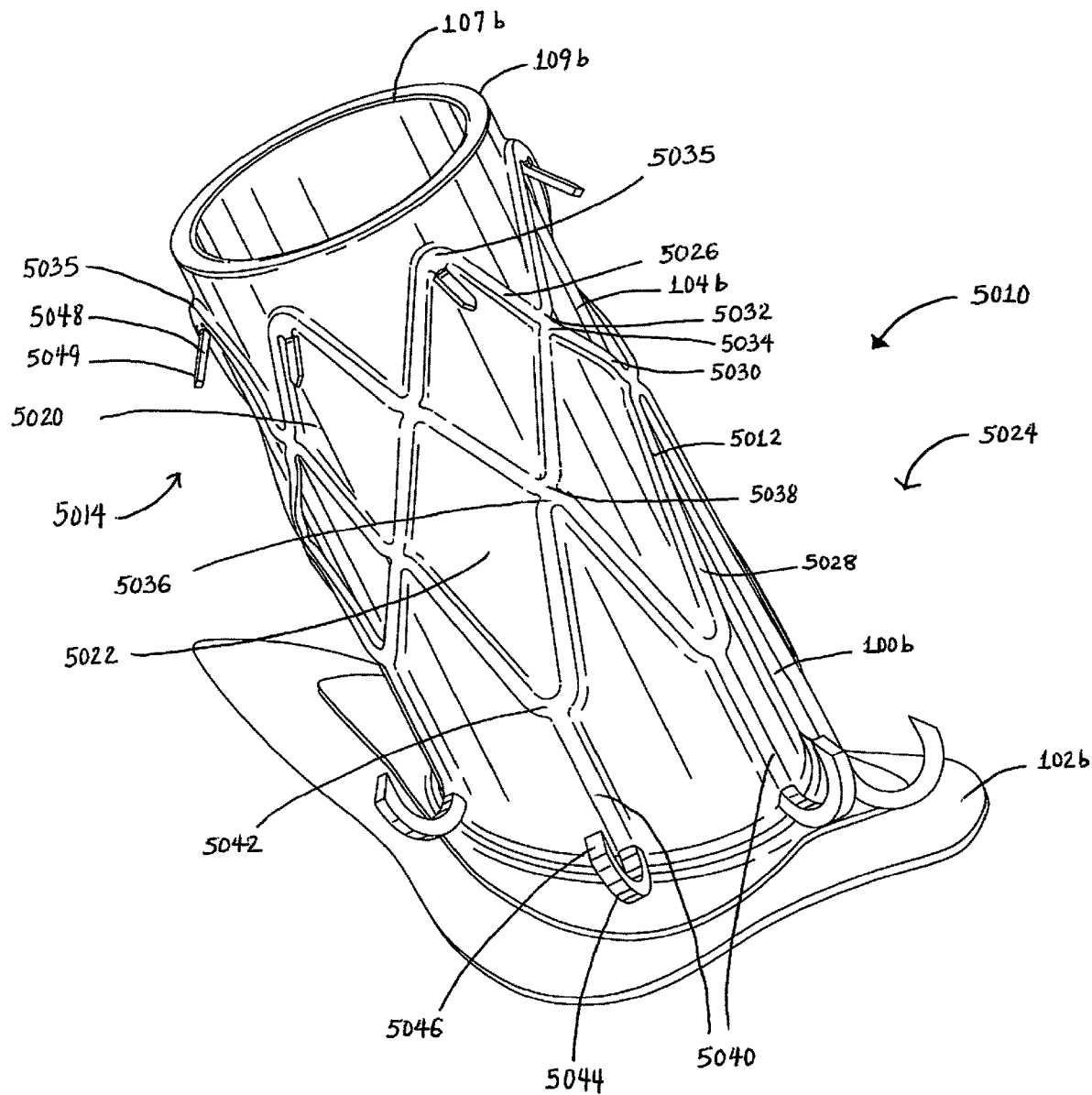

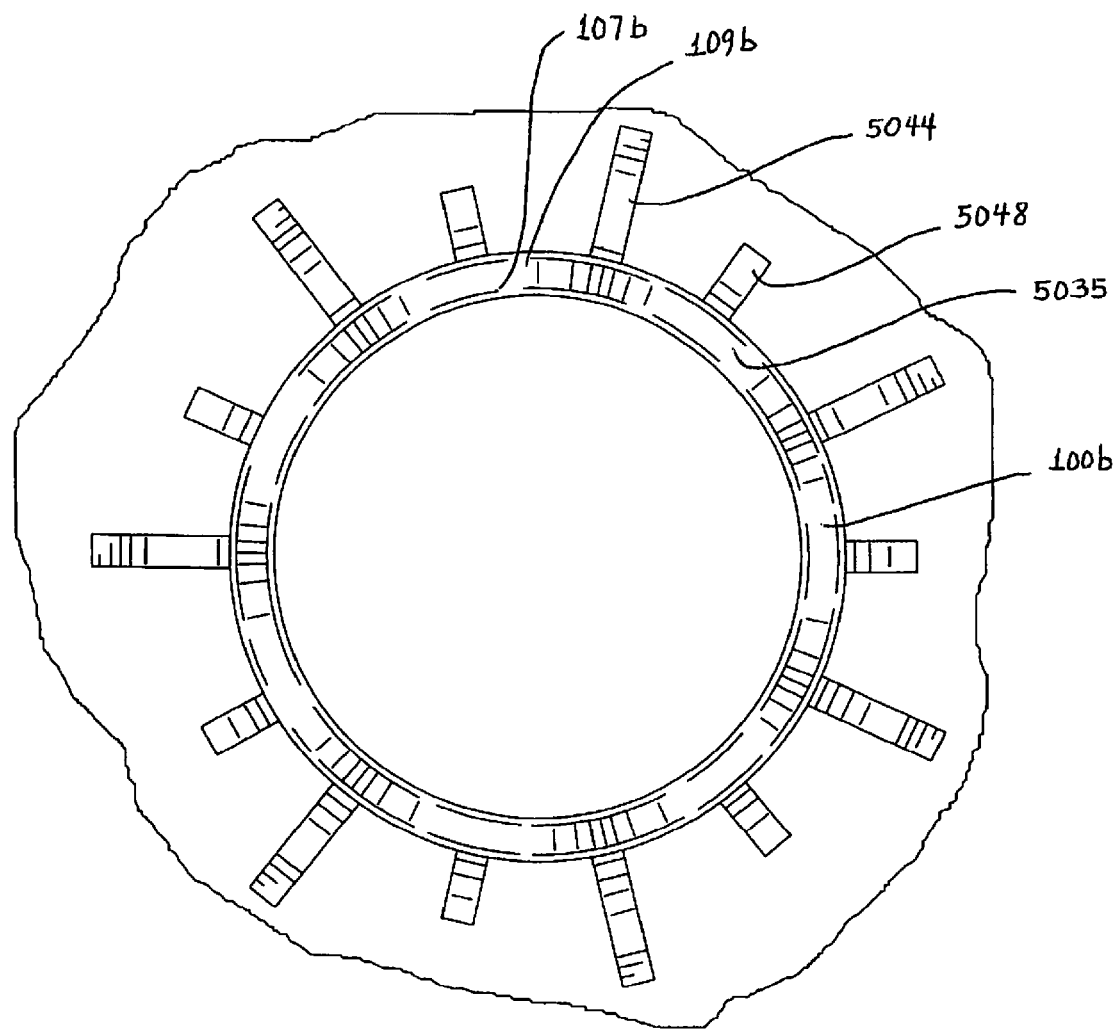

FIG_46

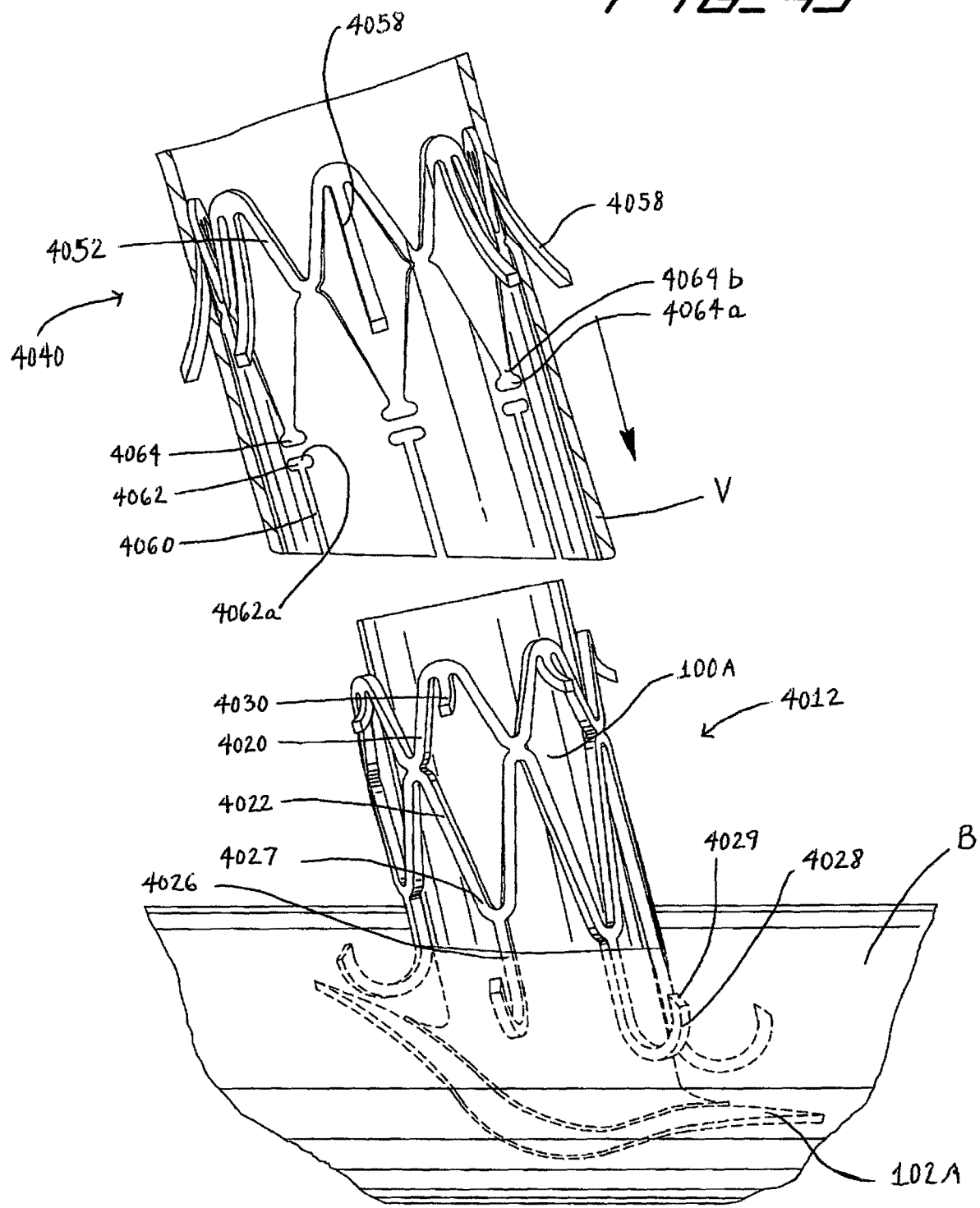
FIG_49

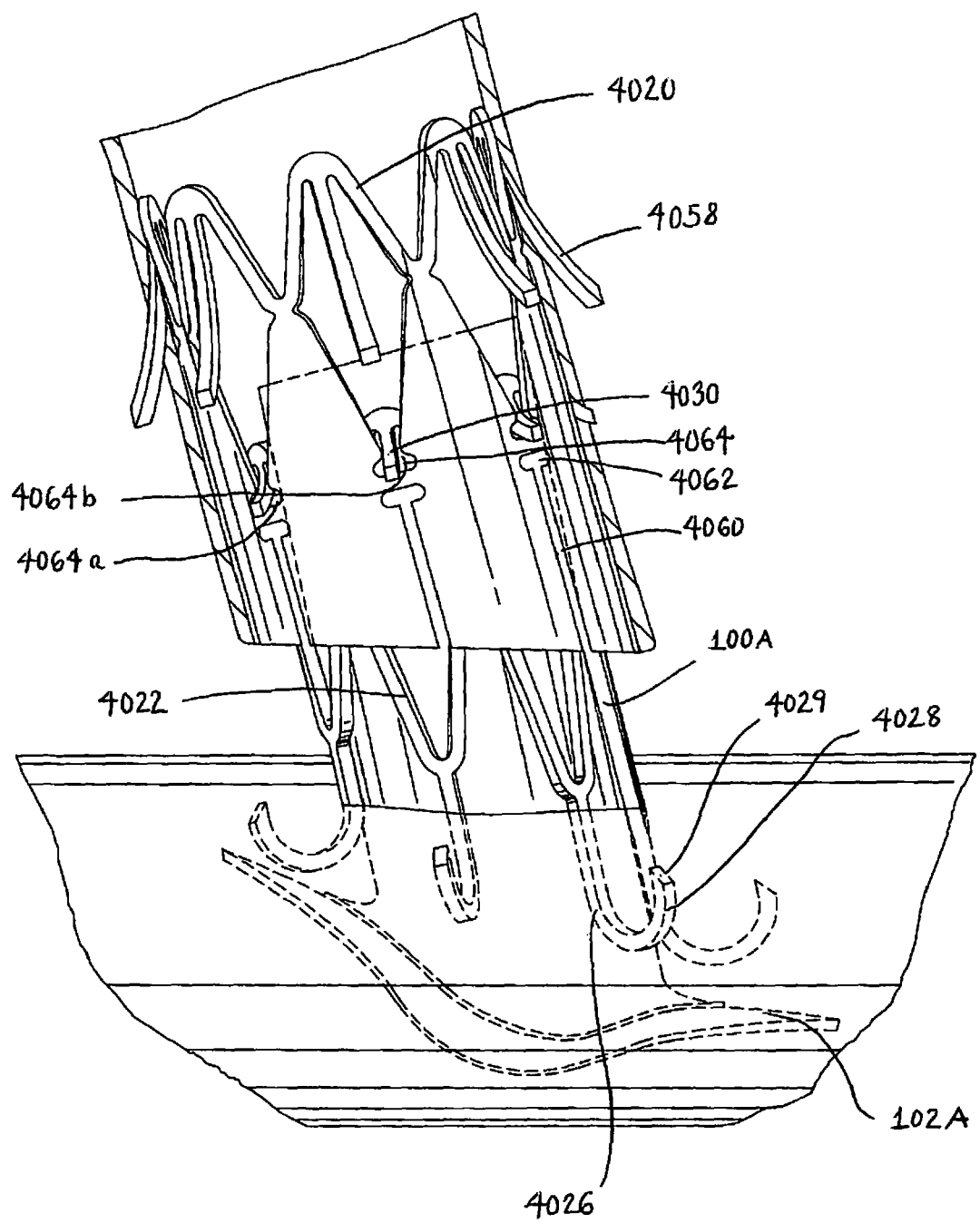
FIG_50

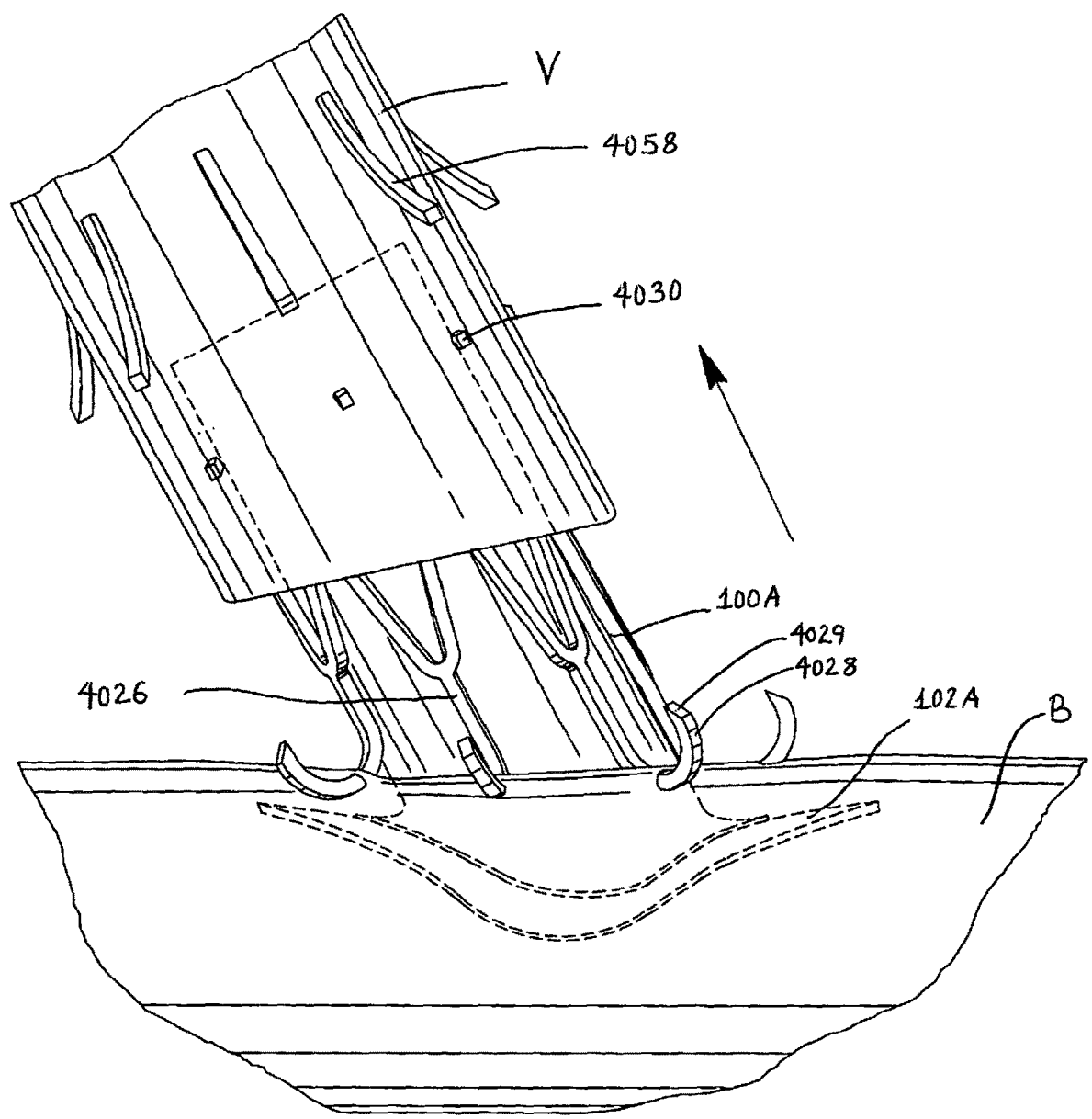

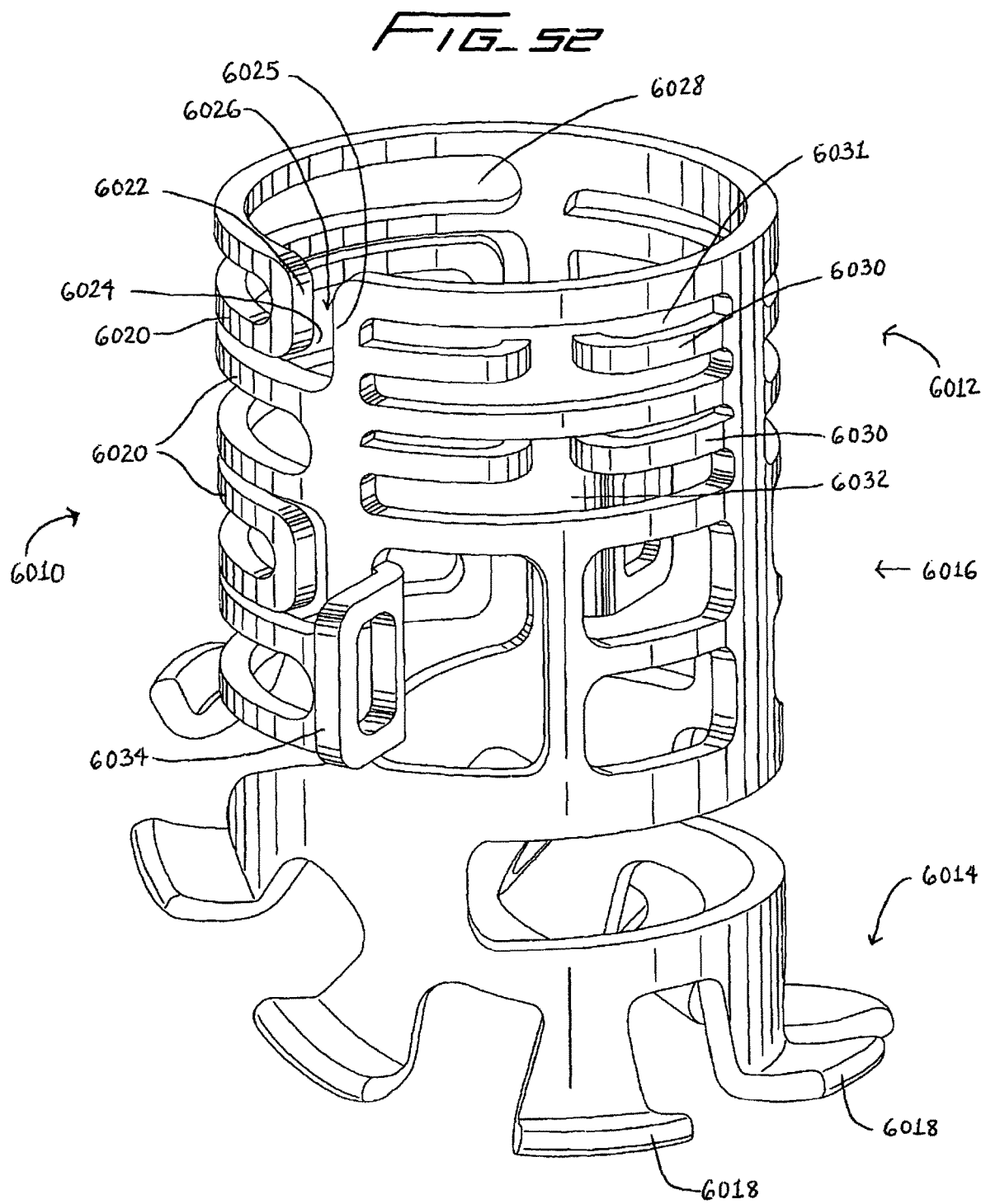

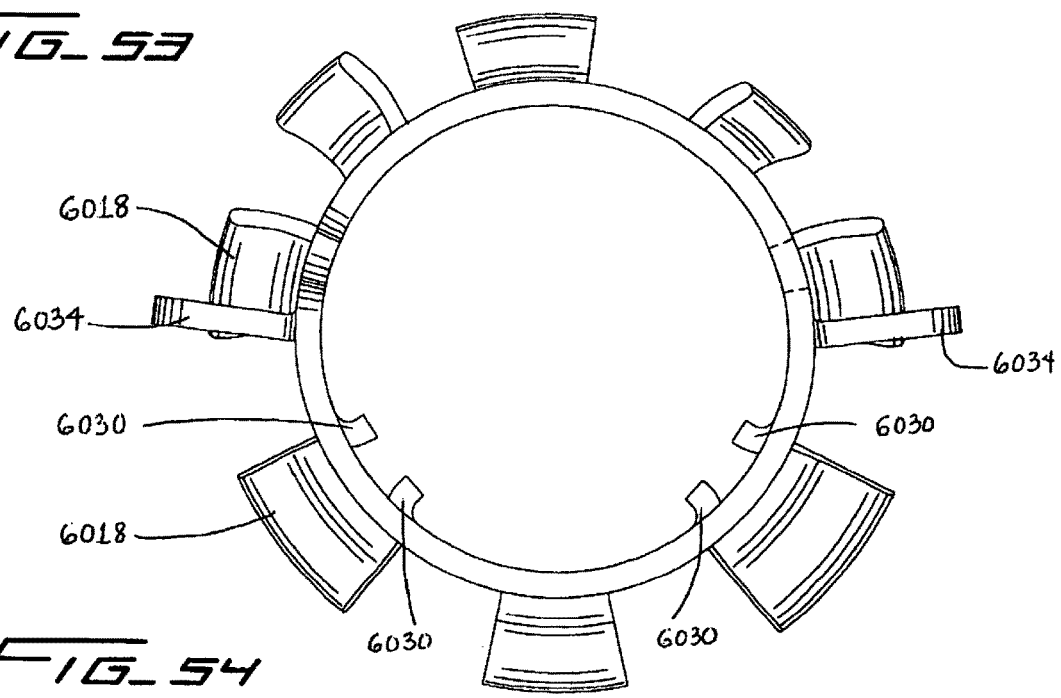
FIG_53
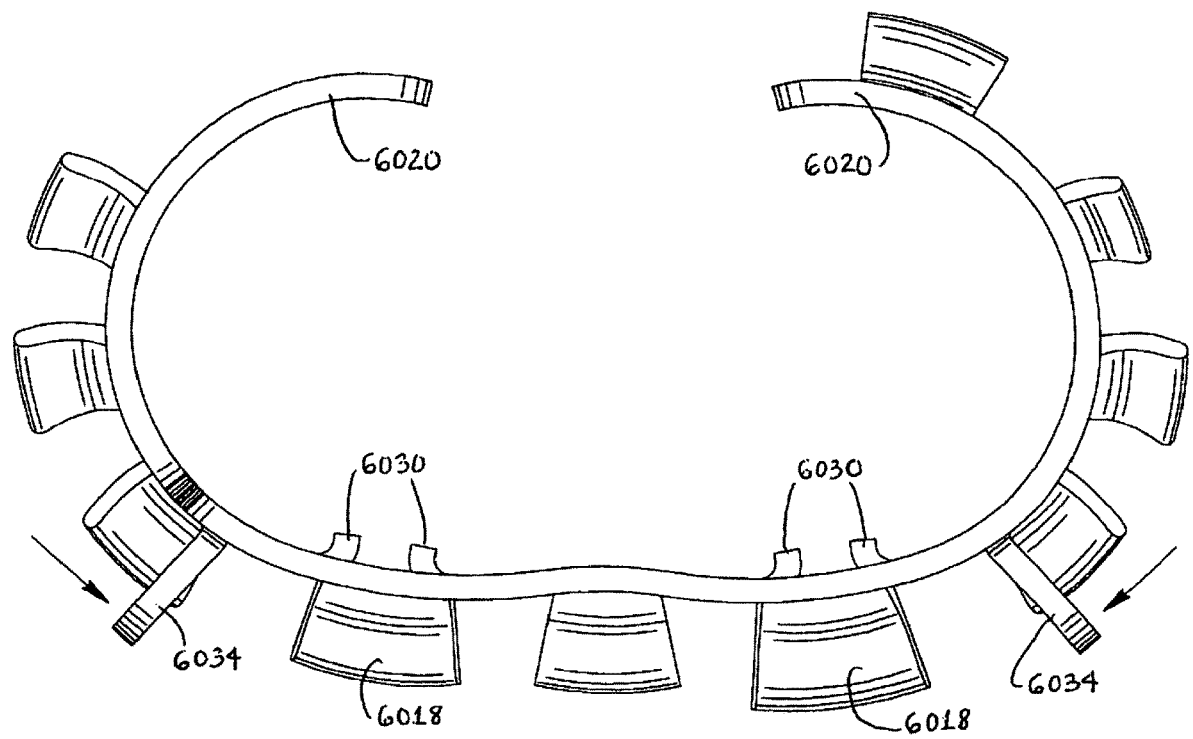
FIG_54

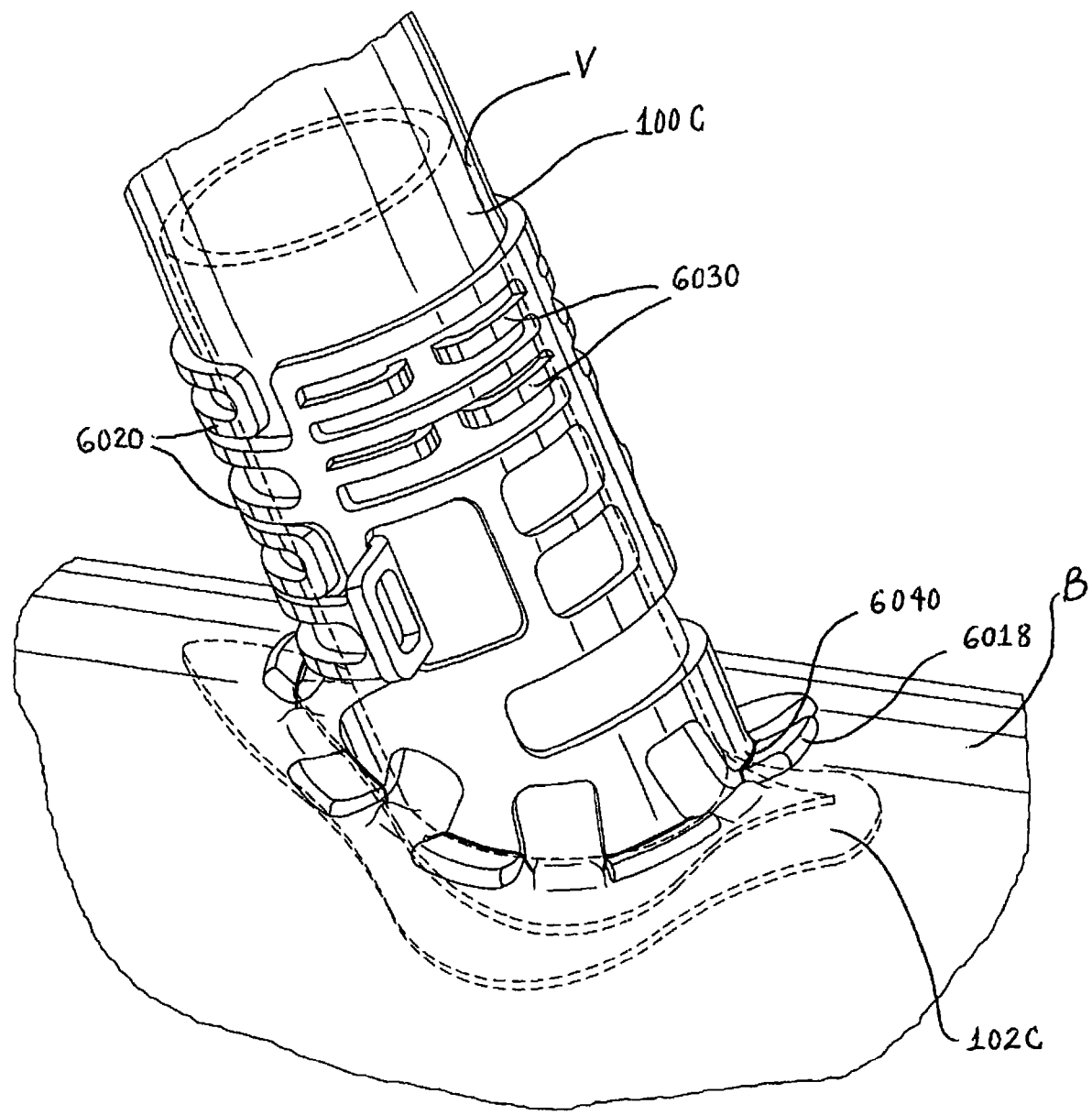

IMPLANTABLE FLOW CONNECTOR

CROSS-REFERENCE TO RELATED APPLICATIONS

This application is a Divisional Patent Application which claims the benefit of U.S. patent application Ser. No. 15/017,620, filed Feb. 6, 2016 and is a continuation of U.S. application Ser. No. 13/792,012, filed Mar. 9, 2013 which claims benefits to U.S. Provisional application No. 61/624,375, filed Apr. 15, 2012 and is a continuation in part of U.S. application Ser. No. 13/716,179, filed Dec. 16, 2012 now U.S. Pat. No. 8,961,446, which is a continuation of U.S. application Ser. No. 12/185,811, filed Aug. 4, 2008, now U.S. Pat. No. 8,366,651, which claims the benefit of U.S. Provisional Application No. 60/953,570, filed Aug. 2, 2007. The entire contents of each of these applications are hereby incorporated by reference herein.

BACKGROUND

Field of the Invention

The present invention relates generally to implantable medical devices and, more particularly, to implantable flow connectors.

Related Art

The mammalian body has numerous tissue-enclosed body spaces. For example, body conduits such as blood vessels, lymph and tear ducts, bowels, urethra, etc., have a lumen through which fluid is carried to facilitate circulation, excretion or other fluid transfer function. Tissue-enclosed body spaces also include body reservoirs such as the stomach, bladder, gall bladder, lymph nodes, etc., which temporarily or permanently retain fluid.

It is often necessary or desirable to directly or indirectly connect body spaces to one another, to other areas in the body, or to an external or implantable medical device such as a sensor, pump, drug delivery system, or other permanently or temporarily implanted therapeutic device. For example, when vessels are damaged, severed or occluded due to physiological conditions, surgical intervention, or disease, certain sections of those vessels are typically bypassed to allow for the free and continuous flow of fluids. For example, an anastomosis is commonly performed for the purpose of connecting different blood vessels together to optimize or redirect blood flow around a damaged or occluded portion of a vessel or to redirect arterial flow into the venous system for enabling dialysis access.

In the context of the peripheral vascular and/or the cardiovascular system, atherosclerosis may cause partial or complete occlusion of an arterial vessel. This may result in restricted blood flow which may compromise perfusion to the tissue served by the blood flow. In the case of an occluded coronary vessel, for example, an area of the heart's myocardium would be compromised, which may lead to a myocardial infarction or other ischemic heart syndrome such as congestive heart failure. In the case of peripheral vascular atherosclerotic disease, occluded vessels lead to ischemic syndromes such as threatened limbs, stroke and other morbidities. Many cases, such a blockage or restriction in the blood flow leading to the heart or peripheral vessels, may be treated by a surgical procedure known as an artery bypass graft procedure.

A bypass procedure involves establishing an alternate blood supply path to bypass a diseased section of a diseased or compromised artery. In the bypass procedure, a surgeon typically dissects one end of a source or "pedicled" artery (such as the internal mammary artery in the case of coronary artery bypass), or a free vessel segment (typically the saphenous vein in the leg), to use as a graft conduit to bypass the obstruction in the affected artery to restore normal blood flow. The graft vessel is connected to the obstructed vessel by means of an anastomosis procedure wherein an opening in the graft vessel is sutured to the obstructed vessel at an arteriotomy site made within the obstructed vessel. There are other indications for vessel anastomoses including revascularizing diseased arteries by creating a side-to side anastomosis between the distal end of the artery and an adjacent vein, thereby allowing the portion of the vein distal the occlusion to become "arterialized." Another indication includes arterial revascularization by "arterializing" a vein through creation of a conduit downstream of the occlusive disease.

The creation of an arteriovenous (AV) fistula is another instance where two body conduits are joined together and involves surgically joining an artery to a vein. AV fistulas are formed for a variety of reasons, one being to provide vascular access for hemodialysis patients. In such an application, the most common site for creation of the AV fistula is the upper extremity, though the lower extremity may also be used. Various surgical techniques and methods may be employed to create the AV fistula. Another indication for creation of an AV fistula is the connection of major vessels such as the aorta and the vena cava in patients with chronic obstruction pulmonary disease (COPD).

The patency of an anastomosis contributes to a successful bypass or AV fistula, both by acute and long-term evaluation. Patency may be compromised due to technical, biomechanical or pathophysiological causes. Among the technical and biomechanical causes for compromised patency are poorly achieved anastomoses due to, for example, poor technique, trauma, thrombosis, intimal hyperplasia or adverse biological responses to the anastomosis. Improperly anastomosed vessels may lead to leakage, create thrombus and/or lead to further stenosis at the communication site, possibly requiring re-operation or further intervention. As such, forming an anastomosis is a critical procedure in bypass or AV fistula surgery, requiring precision and accuracy on the part of the surgeon.

A common traditional approach for forming an anastomosis is to suture together natural or artificial openings in the vessels. To do so, according to one approach, a surgeon delicately sews the vessels together being careful not to suture too tightly so as to tear the delicate tissue, nor to suture too loosely so as to permit leakage of fluid from the anastomosis. In addition to creating a surgical field in which it is difficult to see, leakage of fluid from the anastomosis can cause serious acute or chronic complications, which may be fatal. In addition to the inherent inconsistencies in suture tightness, incision length, placement of the suture, stitch size, and reproducibility, suturing an anastomosis can be very time consuming. This difficulty is compounded by the relatively small dimensions of the vessels involved or the diseased state of the vessel when creating an AV fistula.

SUMMARY

In accordance with one aspect of the present invention, an implantable flow connector for fluidly coupling a source tissue-enclosed body space with a destination conduit is provided. The flow connector includes a conduit having a lumen terminating at a first orifice at a first end of the conduit implantable in the source body space through an opening formed in a tissue wall of the source body space, and a second end of the conduit having a second orifice implantable in the destination conduit through an opening at an end of the destination conduit, and a circumferential flange radially extending from the conduit, proximate the conduit first end, configured to be implanted in the source body space adjacent an opening in the tissue wall of the source body space such that the conduit extends through the opening.

In accordance with another aspect of the present invention, a system for coupling a first space within the body of a patient with a second space within the body of the patient is provided. The system comprises a retention device and a flow connector. The flow connector is insertable into the first and second spaces within the body and has a conduit having a lumen having a first orifice at a first portion of the conduit and a second orifice at a second portion of the conduit, the conduit providing communication between the first and second spaces within the body. The retention device retains the conduit with respect to the first space within the body and is engageable with the first space within the body.

Preferably, the retention device is movable to a reduced profile position for insertion.

In some embodiments, the retention device includes a first set of engaging elements extending therefrom configured to penetrate a wall of the first space within the body and/or a second set of engaging elements extending therefrom configured to penetrate a wall of the second space within the body.

In some embodiments, the flow connector is positioned within an opening in the retention device and in a placement position the retention device is positioned between an outer surface of the flow connector and an inner surface of the second space within the body. The flow connector can apply an outwardly directed radial force to the retention device. In other embodiments, the retention device is positioned about an outer surface of the second space within the body and in a placement position the second body space is positioned between an outer surface of the flow connector and an inner surface of the retention device.

The flow connector preferably includes a flange extending radially outwardly and insertable into the first body space. The flange can include first and second lateral sections and first and second longitudinal sections, the first and second lateral sections configured to cooperate with walls of the first space such that the flange sealingly conforms to an inner surface of a tissue wall adjacent an opening in the first space. The first and second longitudinal sections can extend further radially from the conduit than the first and second lateral sections.

In some embodiments, the retention device comprises an inner component and an outer component wherein at least one of the inner and outer components is relatively slidable with respect to the other component. The outer component can include a compression member to provide a proximal force on the inner body member. The inner body member can be movable from a first configuration to a second spread configuration to provide an axial opening therein for side receipt of the second body space.

In some embodiments, the retention device includes a proximal component and a distal component wherein the proximal component is engageable with the first body space and the distal component is engageable with the second body space, the proximal and distal components interlocking.

The various retention devices disclosed herein can include a plurality of struts and the plurality of struts can in some embodiments form closed geometric shapes.

In accordance with another aspect of the present invention, a system for coupling a first space within the body of a patient with a second space within the body of the patient is provided comprising a flow connector having a conduit having a lumen having a first orifice at a first portion of the conduit and a second orifice at a second portion of the conduit, the conduit configured to be implanted into the second space within the body to provide communication between the first and second spaces within the body. The system of this aspect also includes a retention device having an opening to receive the conduit, the retention device having a first set of engaging members to engage the first space within the body and a second set of engaging members to engage the second space within the body, the retention device maintaining the conduit in position with respect to at least of the first and second body spaces. The first set of engaging members can comprise a first set of penetrating elements with penetrating tips protruding radially therefrom to penetrate a wall of the first space within the body and the second set of engaging elements can comprise penetrating elements configured to pierce a wall of the second space within the body when the second space is positioned over the retention device.

In some embodiments, in a placement position the retention device is disposed between an outer surface of the conduit and an inner wall of the second space within the body.

The retention device is preferably movable to a reduced profile configuration for insertion.

In some embodiments, the retention device comprises first and second components movable from a spaced position to an engaged position, the first set of engaging members extending from the first component and the second set of engaging elements extending from the second component.

In some embodiments, the first set of engaging members extends toward a proximal end of the retention device.

In some embodiments, the flow connector includes a flange extending radially from the first portion of the conduit and is configured to be implanted in the first space within the body in accordance with another aspect of the present invention, a system is provided for coupling a first space within the body of a patient with a second space within the body of the patient comprising a flow connector insertable into the first and second spaces within the body, the flow connector having a conduit having a lumen having a first orifice at a first portion of the conduit and a second orifice at a second portion of the conduit, the conduit providing communication between the first and second spaces within the body. The system of this aspect includes a retention device for retaining the conduit within the second space within the body, the retention device including a plurality of struts and having an axial opening to receive and engage the flow connector Preferably, the retention device is movable to a reduced profile position for insertion.

In some embodiments, the retention device is movable to an expanded open position to receive the flow connector therein.

In accordance with another aspect of the present invention, a system for fluidly coupling a first space within the body of a patient with a second space within the body of the patient is provided comprising a first device, a second device engageable with the first device, and a flow connector having a conduit having a lumen having a first orifice at a first portion of the conduit and a second orifice at a second portion of the conduit, the conduit configured to be implanted into the second space within the body to provide communication between the first and second spaces within the body. The first device engages with at least one of the flow connector and the first space within the body and the second device engages with at least one of the flow connector and second space within the body.

In some embodiments, a first plurality of engaging elements extend from the first device to engage a wall of the first body space and a second plurality of engaging elements extend from the second device to engage a wall of the second body space.

In some embodiments, the second device is positioned over the first device and internal of the second body space. In some embodiments, at least one of the first and second devices can be slidable relative to the other device and the second device can be positioned external of the second body space. The first device can extend distally of the first device when the first and second devices are interlocked.

In accordance with another aspect of the present invention, an implantable flow connector implantable into a body of a patient for fluidly coupling a first space within the body of the patient with a second space within the body of the patient is provided. The implantable flow connector comprises a conduit having a lumen having a first orifice at a first portion of the conduit and a second orifice at a second portion of the conduit, the conduit configured to be implanted into the second space within the body to provide fluid flow between the first and second spaces within the body, and a retention portion having radially extending wall engaging portions, the retention device engageable with the first and second spaces within the body.

In some embodiments, the retention portion is embedded in a wall of the conduit.

The retention portion can include a plurality of struts with radially extending penetrating elements. The flow connector can include a flange extending radially from the conduit.

In accordance with another aspect of the present invention, a system for coupling a first space within the body of a patient with a second space within the body of the patient is provided, the system comprising a flow connector having a conduit and a flange, the conduit having a lumen having a first orifice at a first portion of the conduit and a second orifice at a second portion of the conduit, the conduit configured to be implanted into the second space within the body to provide communication between the first and second spaces within the body, the conduit dimensioned to receive the second space within the body thereover, the flange extending radially from the first portion of the conduit and configured to be implanted in the first space within the body, and a retention device having an opening to receive the first body space such that in a placement position the first space within the body is positioned between an external wall of the flow connector and an internal wall of the retention device, the retention device having a plurality of anchoring tabs at a distal portion positionable external of the first space within the body. Preferably, the anchoring tabs provide an anchor for suture passed through the first space within the body.

In accordance with another aspect of the present invention, a retention device for retaining a first body space and a second body space is provided, the retention device comprising a first set of engaging members extending from the first component to engage the first body space and a second set of engaging members extending from the second component to engage the second body space to retain the first and second body spaces to couple the first and second body spaces. In some embodiments, the retention device enables fluid coupling of the first and second body spaces. A non-porous material can be attached internal and/or external of the retention device to enable fluid coupling of the first and second body spaces.

In some embodiments, the retention device comprises a first component and a second component, the first component movable relative to the second component, and a first set of engaging members can extend from the first component and the second set of engaging members can extend from the second component. Preferably, the first and second engaging members have tissue penetrating tips. In some embodiments, the first and second components releasably interlock. The first and second components can interlock by a protrusion on one of the components engaging an opening in the other component.

In some embodiments, the retention device is formed of a plurality of struts and has an axial opening.

The present invention also includes method of implanting the flow connector. In accordance with one method of the present invention a method of implanting and securing an implantable flow connector in a body of a patient for providing communication of a first space within the body of the patient with a second space within the body of the patient is provided comprising the steps of a) providing a flow connector having a lumen having a first orifice at a first portion of the conduit and a second orifice at a second portion. b) providing a retention device having a proximal portion and a distal portion, c) inserting the retention device into the first space within the body, d) subsequently inserting the flow connector through an opening in the retention device so the second portion of the flow connector extends into the first space within the body; and e) placing the second space within the body over the retention device.

In some embodiments, the step of inserting the retention device into the first space within the body comprises compressing the retention device to reduce its outer diameter.

In some embodiments, the step of inserting the retention device includes placing the retention device in a delivery cannula wherein it is compressed and then releasing the retention device from the cannula so it returns to a non-compressed position.

In some embodiments, the retention device includes a first set of engaging elements with penetrating tips penetrating the first space within the body when the distal portion of the retention device is in a placement position within the first space within the body and/or a second set of engaging elements with penetrating tips penetrating a wall of the second space within the body when the second space within the body is in a placement position over the retention device.

The second portion of the flow connector can include a flange extending radially from the connector and engaging an inner wall of the first space within the body.

In some embodiments, the retention device includes a first component and a second component, and the method further includes the step of interlocking the first and second components. In some embodiments, the first component is distal of the second component and the second component engages the first space within the body and the first component engages the second space within the body.

In some embodiments, one of the first and second components has at least one locking tab and the other component has at least one slot, and the step of interlocking the components includes the step of causing the at least one locking tab to locking engage the at least one slot, and preferably the components can be released after locking if desired.

In some embodiments, the step of inserting the flow connector through an opening in the retention device includes the step of placing the flow connector in a reduced profile position within a delivery member and inserting the delivery member through the opening in the retention device.

In some embodiments, the first space within the body is a source body space and a proximal portion of the flow connector is inserted through an opening formed in a tissue wall of the source body space, and the second space within the body is a destination element and a distal portion of the flow connector is insertable into the destination element through an opening in a surface of the destination element.

In accordance with another aspect of the present invention, a method for forming a sutureless anastomosis between a first space within a body of a patient and a second space within the body of the patient is provided, the method comprising the steps of a) providing a flow connector having a lumen having a first orifice at a first portion of the conduit and a second orifice at a second portion, b) providing a retention device having a plurality of penetrating members engageable with the wall of at least one of the spaces within the body; and c) positioning the flow connector internally of the retention device.

In some embodiments, the flow connector includes a flange extending radially outwardly from the second portion, and the flange of the flow connector can be positioned in the first space within the body and the first orifice can be positioned within the second space within the body.

The method can further comprise the step of inserting the retention device into the first space within the body wherein the step of positioning the flow connector internally of the retention device occurs subsequent to the step of inserting the retention device into the first space within the body. The step of positioning the flow connector internally of the retention device can further comprise the step of opening the retention device to provide a side entry to receive the flow connector therein.

The method may further comprise the step of placing the second space within the body over an external wall of the retention device, and this step can occur in some embodiments subsequent to the step of positioning the flow connector internally of the retention device.

In some embodiments, the retention device includes first and second components, and the method further comprises the step of interlocking the first and second components to secure the components together and to maintain a fluid connection between the first space within the body and the second space within the body. The step of interlocking the components can include the step of sliding the first component over the second component.

In accordance with another aspect of the present invention, a method of implanting and securing an implantable flow connector in a body of a patient for providing communication of a first space within the body of the patient with a second space within the body of the patient is provided, the method comprising a) providing a flow connector having a lumen having a first orifice at a first portion of the conduit, a second orifice at a second portion and a retention portion, the retention portion having a first plurality of penetrating members to engage the first body space, b) inserting the flow connector into the first space within the body, and c) placing the second space within the body over the flow connector.

A second plurality of penetrating members can be positioned proximal of the first plurality of penetrating members to penetrate the second body space when positioned over the flow connector.

In some embodiments, the step of placing the second space within the body over the retention device occurs subsequent to the step of inserting the flow connector into the first space within the body.

In accordance with another aspect of the present invention, a method of implanting and securing an implantable flow connector in a body of a patient for providing communication of a first space within the body of the patient with a second space within the body of the patient is provided, the method comprising the steps of a) providing a flow connector having a lumen having a first orifice at a first portion of the conduit and a second orifice at a second portion, b) providing a retention device having a proximal portion and a distal portion, c) inserting a proximal portion of the flow connector into the first body space, d) placing the second space within the body over the flow connector and e) subsequently placing the retention device over the second space within the body.

The step of placing the retention device over the second space within the body can comprise the step of opening the retention device to provide a side entry for the second space within the body.

In some embodiments, the retention device has an outer component and an inner component, wherein the outer component engages the first space within the body, and the method may further comprise the step of moving one of the first and second components relative to the other component to interlock the first and second components.

In some embodiments, the step of placing the retention device over the second body space places a plurality of suture tabs on an external surface of the first body space.

BRIEF DESCRIPTION OF THE DRAWINGS

Embodiments of the present invention are described herein in conjunction with the accompanying drawings, in which:

FIG. 19 is a perspective view of one embodiment of the present invention in which an artificial conduit and two flow connectors are provided for implantation in a recipient;

FIG. 20 is a perspective view of a first embodiment of a retention device for use with the flow connector;

FIG. 21 is a top view of the retention device of FIG. 20;

FIG. 22 is a perspective view of the retention device of FIG. 20;

FIG. 23 is a perspective view of the retention device of FIG. 20 shown prior to insertion through the opening in the first body space, e.g. artery, and shown in a reduced profile position within an insertion cannula;

FIG. 24 is a perspective view of the retention device of FIG. 20 shown inserted through the opening in the artery;

FIG. 25 is a view similar to FIG. 24 showing expansion of the retention device when removed from the insertion cannula;

FIG. 26 is a perspective view illustrating a flow connector being inserted in a reduced profile configuration within a delivery sheath (cannula) through the axial opening of the retention device and into the artery;

FIG. 27 illustrates the flow connector released from the delivery sheath to expand within the axial opening in the retention device;

FIG. 36 is a rear view of the inner member of the retention device of FIG.

FIG. 37 is a top view of the retention device of FIG. 32 in the normal placement configuration;

FIG. 38 is a top view of the retention device of FIG. 32 shown starting to be spread to an open position for receiving the second body space, e.g. a vein;

FIG. 39 is a top view of the retention device of FIG. 32 shown in the open (spread) position for receiving the vein;

FIG. 40 illustrates a flow connector positioned within the first body space, e.g. an artery, a vein positioned over the flow connector, and the retention device of FIG. 32 being moved toward the vein for positioning thereover;

FIG. 41 illustrates the retention device of FIG. 32 positioned over the vein and flow connector and further showing the distal portion of the outer body member secured to the artery and the outer and inner members interlocked;

FIG. 42 is a perspective view of another alternate embodiment of the retention device of the present invention, the retention device embedded in a flow connector;

FIG. 43 is a top view of the retention device of FIG. 42;

FIG. 49 illustrates the distal connector of FIG. 47 positioned within the artery and the proximal connector of FIG. 47 being moved toward the distal connector and having a second body space, e.g. a vein (shown in cross-section) positioned thereover;

FIG. 50 is a view similar to FIG. 49 showing the proximal connector interlocked with the distal connector;

FIG. 51 is a view similar to FIG. 50 showing the retention device and flow connector pulled proximally so the hooks of the distal connector penetrate the wall of the artery around the opening;

FIG. 52 is a perspective view of another alternate embodiment of the retention device of the present invention;

FIG. 53 is a top view of the retention device of FIG. 52;

FIG. 54 is a top view of the retention device shown in the open (spread) position to receive a second body space, e.g. a vein, within the opening; and FIG. 55 illustrates the retention device of FIG. 52 positioned around a vein having a flow connector therein and abutting an outer surface of the wall of the artery.

DETAILED DESCRIPTION

Aspects of the present invention are generally directed to an implantable flow connector. Other aspects of the present invention are also directed to an implantable flow connector and a retention device for securing the flow connector. The flow connector of the present invention is configured to be implanted in a tissue-enclosed body space such as a body conduit or body reservoir to provide a flow path for fluid from the source body space to another body space, a man-made or body conduit, an external or implanted medical device, or other destination element.

Embodiments of the flow connector comprise a conduit having a lumen that terminates at an orifice on opposing ends of the conduit, and a flange radially extending from one of the two ends of the conduit. The flow connector is configured to be implanted into the source body space via a natural or artificial opening (e.g., a man-made opening) in a region of the tissue wall that defines the body space. The flange surrounds the conduit orifice through which the conduit lumen is fluidically coupled to the interior of the body space, and is configured to be self-retained in the body space.

The conduit is also configured to be retained in the noted destination device or body space or body region (collectively and generally referred to herein as the destination element). For example, when the destination element is a tissue-enclosed body space, the conduit is configured to be implanted into the destination body space via a natural or artificial opening in the tissue wall defining that body space. Once implanted, fluid exiting the conduit orifice at the distal end of the flow connector flows into the destination element. As such, the flow connector of the present invention fluidically couples the source body space and destination device or body space.

As noted, embodiments of the flow connector of the present invention may be used to fluidically couple any tissue-enclosed body space or implanted medical device to any type of destination including any other tissue-enclosed body space, other areas in the body, or an external or implanted medical device. Embodiments of the flow connector may be configured to be implanted in any tissue-enclosed body space including, but not limited to, body conduits such as blood vessels, lymph ducts, tear ducts, bowels, urethra, etc., which have a lumen through which fluid is carried to facilitate circulation, excretion or other fluid transfer, as well as body reservoirs such as the stomach, bladder, gall bladder, lymph nodes, etc., which temporarily or permanently retain fluid. For ease of description, embodiments of the flow connector described below are specifically configured for implantation to create an arteriovenous (AV) fistula and, more specifically, an AV fistula in the upper or lower extremity to provide vascular access for hemodialysis patients.

Figure 1A:
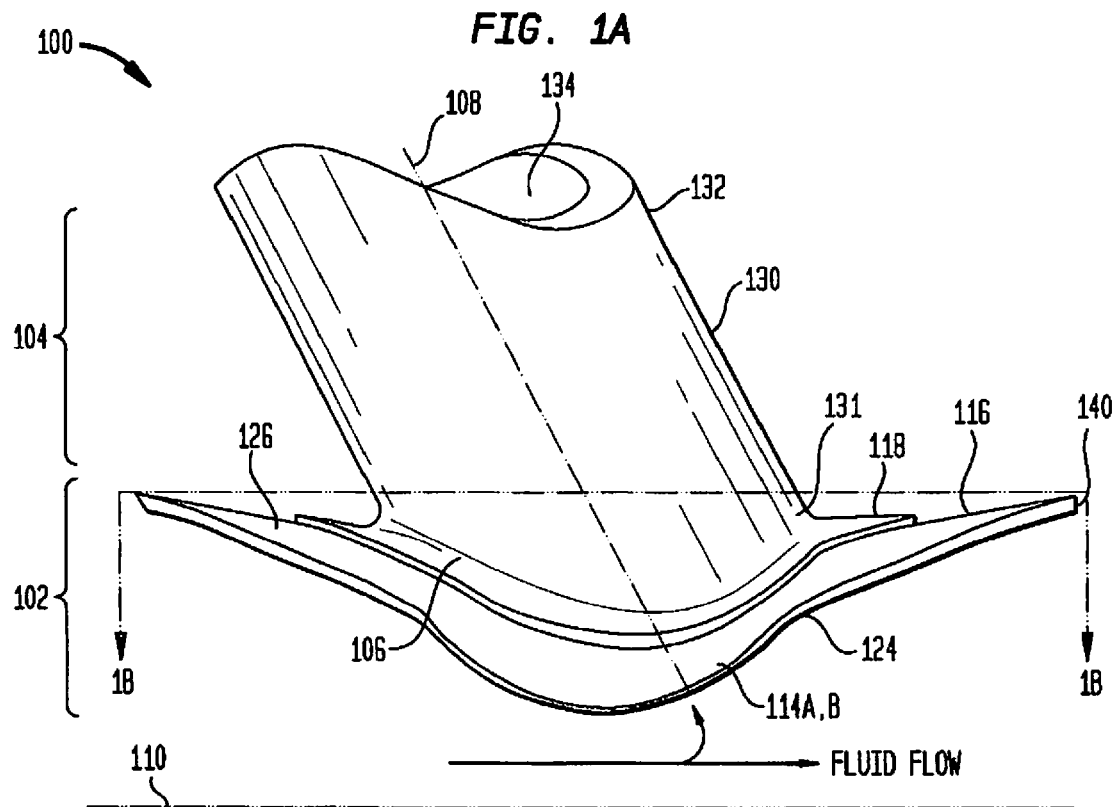
FIG. 1A is a side view of one embodiment of a flow connector of the present invention.

FIG. 1A is a side view of one embodiment of a flow connector of the present invention. In FIG. 1A, flange 102 is a circumferential flange and is configured to radially extend from conduit 104 proximate to its first or proximal end 131 of conduit 104. Conduit 104 terminates at proximal end 131 of conduit 104 at an orifice. A second orifice is disposed on the opposite side of conduit 104 at its distal end 132. Flange 102 comprises a contact surface 126, which is configured to contact an inner surface of the tissue wall defining the source body space of a recipient when it is implanted therein. On the opposite side of flange 102 from contact surface 126 is an exposed surface 128 which is exposed to fluids passing through the source body space (not shown).

Figure 1B:
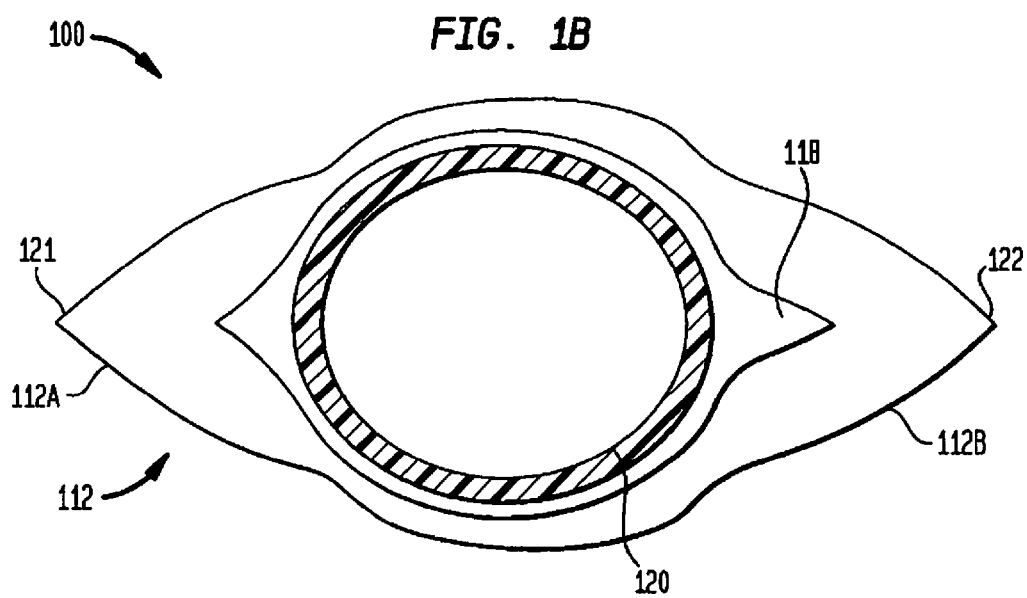
FIG. 1B is a modified top view of the embodiment of the present invention illustrated in FIG. 1A taken along cross-section line 1B-1B in FIG. 1A.
Figure 1C:
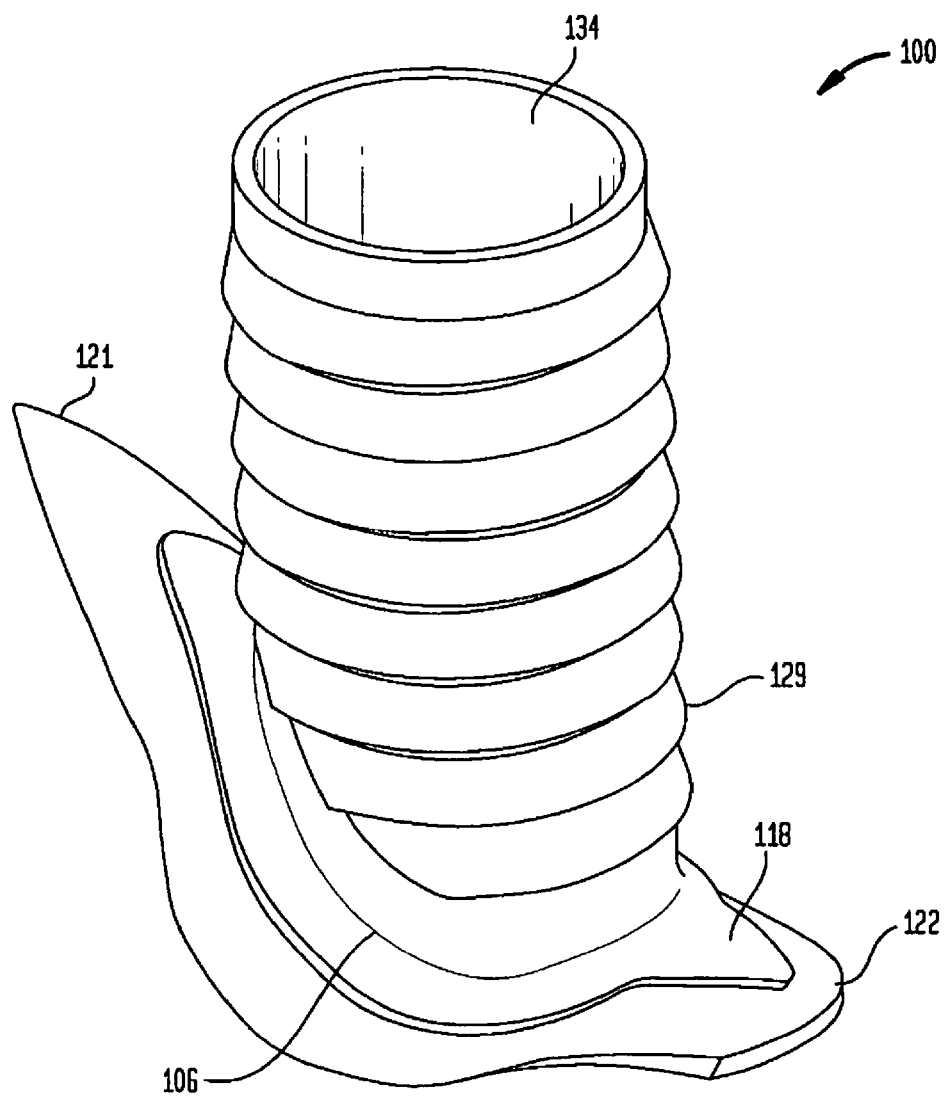
FIG. 1C is an isometric view of another embodiment of the flow connector of the present invention.
Figure 1D:
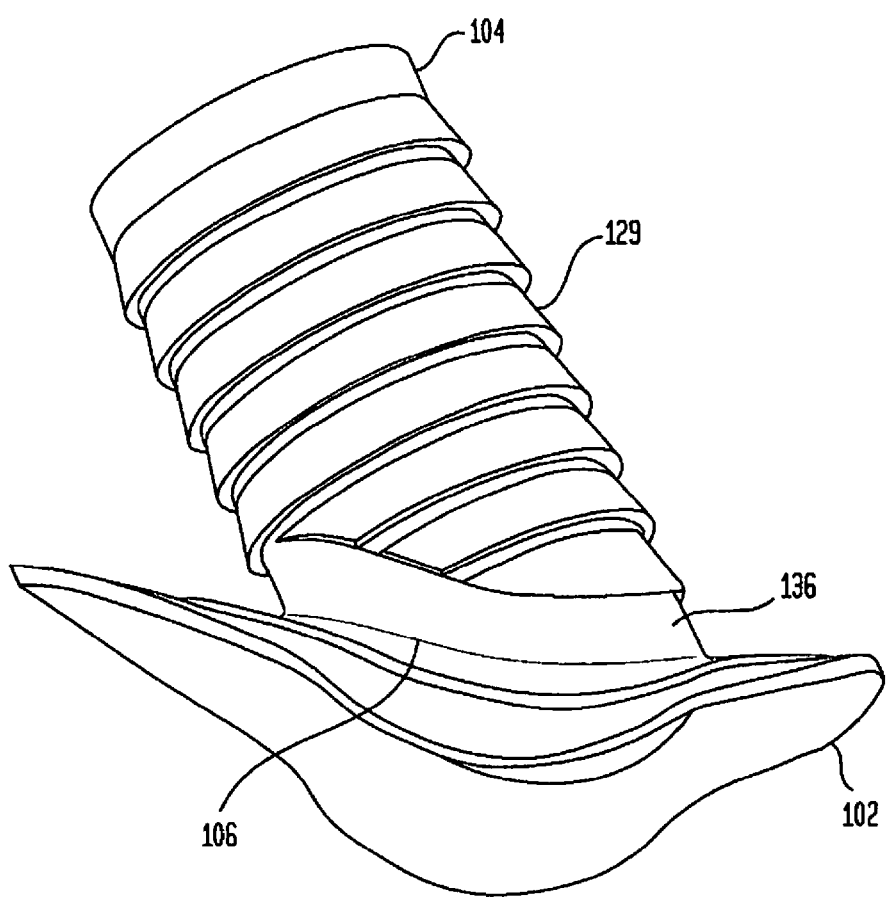
FIG. 1D is another isometric view of the embodiment of e flow connector illustrated in FIG. 1C.
Figure 1E:
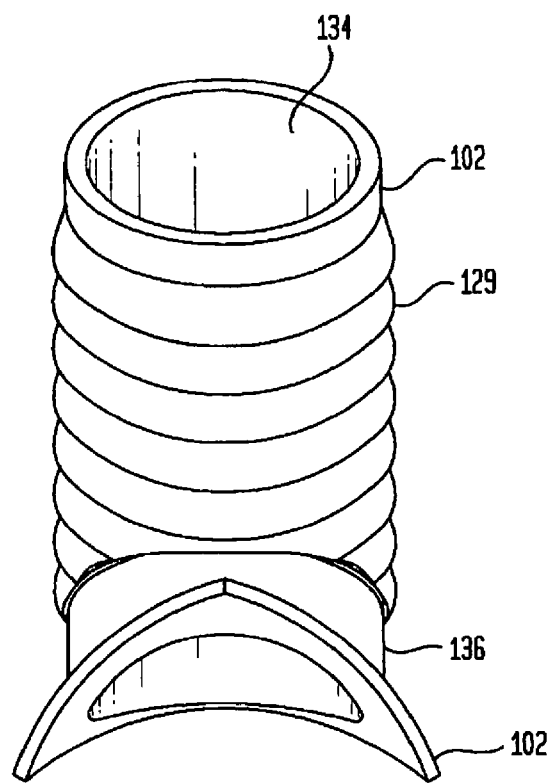
FIG. 1E is yet another isometric view of the embodiment of the flow connector illustrated in FIG. 1C.

In one embodiment of the present invention, flange 102 comprises a plurality of circumferentially adjacent sections. For example, a pair of opposing flange sections 112A and 112E can be provided. In those embodiments designed for implantation in a body conduit, flange sections 112 are referred to as longitudinal flanges, and flange section 112A is referred to as heel section 112A while flange section 112B is referred to as toe section 112B. In addition to longitudinal sections 112, there is a pair of substantially similar lateral sections 114A, 114B extending from opposing sides of conduit 104 approximately equidistant from flanges 112A, 112B. Circumferentially opposed sections 114A, 114B, also referred to herein as lateral sections 114 due to their substantially orthogonal positioning relative to longitudinal sections 112, are configured to extend from flange 102 as illustrated in FIGS. 1C-1E, on opposing sides of conduit 104, and are further configured to extend circumferentially around a longitudinal axis 110 of the source body space in which flange 102 is to be implanted. The circumferential radius of lateral sections 114A, 114B is selected based on the radius of curvature of the region of the source body space in which flow connector 100 is to be implanted. In one embodiment, the radius 297 defined from longitudinal axis 110 to contact surface 126 of lateral sections 114A, 114B is substantially equal to the radius 298 defined from longitudinal axis 110 to the inner surface of the source body space. In other embodiments, radius 297 defined from longitudinal axis 110 to contact surface 126 of lateral sections 114A, 114B is larger than the radius 298 defined from longitudinal axis 110 to the inner surface of the source body space. Furthermore, in those embodiments, flange 102 is constructed of shape-memory material such that external forces exerted on flange 102 made of memory material may cause flange 102 to at least partially bend, but the nature of the memory material will generate forces to return flange 102 to its original shape. In such embodiments where the radius of lateral sections 114A, B is greater, that radius defined from longitudinal axis 110 to contact surface 126 of lateral sections 114A, B may be 1 to 10% larger than the radius defined from longitudinal axis 110 to the inner surface of the source body space. The larger radius of lateral sections 114A, B combined with the nature of the memory material with which it is constructed will generate a chronic outward force when flow connector 100 is implanted within the source body space, which will in turn cause the walls of the source body space to resist the outward force, thereby providing a compression force to lateral sections 114A, B. The compression force applied to lateral sections 114A, B in turn urges contact surface 126 of flange 102 towards the opening in the tissue wall of the source body space, thus providing a seal between contact surface 126 of flange 102 and the tissue wall such that fluid within the source body space will not leak after implantation of flow connector 100. It is to be understood that in one embodiment of the present invention, some fluid from the source body space may or may not leak immediately after implantation. However, with normal physiological healing processes, such leakage will soon thereafter cease as the aforementioned seal will be provided by contact surface 126 on flange 102 with the tissue wall, thereby eliminating the need for additional elements such as glue, sutures etc. in order to stop or prevent fluid leakage.

In addition to providing a seal between contact surface 126 and flange 102, as described above, the larger radius of lateral sections 114A, B combined with the nature of the memory material with which it is constructed also acts to provide support for flow connector 100. As used herein, supporting flow connector 100 refers to physically supporting flow connector 100 such that it retains its position within the source body space, after implantation, without other components or objects contributing towards the retaining of its implanted position.

In one embodiment of the present invention, lateral sections 114A, B extend circumferentially around the interior surface of the source body space so as to leave approximately 180° of the source conduit's interior surface circumferentially uncovered by lateral sections 114A, B and flow connector 100 generally. By leaving approximately 180° uncovered, obstruction to the flow of fluid within the source body space is minimized while enhancing stability provided by lateral sections 114A, B to flow connector 100 when implanted. Longitudinal sections 112 are also circumferentially curved with respect to the interior surface of the source body space such that contact surface 126 makes contact with the interior surface of the source body space in a sealing region 116, thereby providing a fluid tight or hydrophobic seal as well as stability between flow connector 100 and the source body space.

Adjacent to sealing region 116 is reinforcement region 118, configured to provide physical support to flow connector 100 by being constructed and arranged to oppose various explanting or other forces that may be exerted on flange 102 and conduit 104 when flow connector 100 is implanted in the source body conduit. Reinforcement region 118 is configured to have a rigidity that it aids in the opposition of deflection forces, and is therefore less prone to flexing of portions of flange 102 and/or conduit 104. The rigidity of reinforcement region 118 decreases in a radially-increasing direction thereby aiding in the implantation of flange 102 in the source body space. It should be appreciated that the rigidity may be provided in various ways, according to various embodiments of the present invention. For example, reinforcement region 118 may have a composition with a rigidity which makes it more rigid than sealing region 116 or other portions of flange 102. For example, in one embodiment of the present invention, sealing region 116 may be manufactured with material having a Shore value of 80 A and reinforcement region 118 may be manufactured with material having a Shore value of 55 D. In other embodiments, reinforcement region 118 may be manufactured with the same material as its adjacent or other sections of flange 102, but reinforcement region 118 may be configured to be thicker than adjacent sections of flange 102, thereby making reinforcement region 118 more rigid. By avoiding substantial deflecting or bending, flange 102 remains larger than the aperture in the source body space through which flange 102 was inserted, thus preventing explanting or pull-out from the source body space. As used herein, substantial deflecting by flange 102 refers to the reduction of the surface area of flange 102 to a size allowing flange 102 in its deflected state to fit through aperture in the source body space through which flange 102 was inserted.

Reinforcement region 118 is proximal to conduit 104 so as to provide structural integrity to conduit 104 such at the orifice at the proximal end 131 of conduit 104 can withstand a greater amount of compression force than without reinforcement region 118 being present. As will be further discussed below, reinforcement region 118 also may assist in opposing explant forces that may be applied, intentionally or inadvertently, on flow connector 100. Although reinforcement section 118 is illustrated in FIGS. 1A-1C to be substantially contiguous, it is to be understood that in other embodiments of the present invention reinforcement section 118 may not be contiguous but may have multiple reinforcement regions 118 disposed circumferentially around conduit 104. Similarly, it is to be understood that although reinforcement region 118 is illustrated in FIG. 1B is shown as having a similar or at least a corresponding perimeter as that of flange sections 112, 114, in other embodiments of the present invention, reinforcement region 118 may have a perimeter which is shaped differently from that of flange sections 112, 114.

Longitudinal sections 112 are configured to facilitate implantation of flow connector 100 while also opposing pullout forces which may otherwise pull flow connector 100 out from the source body space (not shown) after flow connector 100 is implanted. Lateral sections 114A, 13 are also configured to facilitate implantation and further configured to maintain the position of flow connector 100 with respect to the source body space (not shown) after flow connector 100 is implanted. In one embodiment of the present invention, lateral sections 114A, B have a radius of curvature substantially identical to the radius of curvature of the source body space into which it is to be implanted. In other embodiments of the present invention, lateral sections 114A, B has a curvature radius which is slightly larger than the curvature radius of the source body space into which it is to be implanted. When this embodiment is implanted in the source body space, the larger curvature radius of lateral sections 114A, B will cause the source body space to generate compression forces on the larger lateral sections 114A, B which will in turn promote the maintenance of the position of flow connector 100 in the source body space.

FIG. 1B is a cross-sectional view along the line 1B-1B noted in FIG. 1A, in which a substantial portion of the conduit body 130 is shown as if removed for the purpose of showing an unobstructed view of the longitudinal sections 112 and lateral sections 114. In the embodiment shown in FIG. 1B, heel section 112A and toe section 112B have apices, heel section apex 121 and toe section apex 122, respectively, when viewed from the perspective illustrated in FIG. 1B. In this embodiment, heel section apex 121 and toe section apex 122 come to a sharp point which may be helpful in redirecting fluid flowing within the source body space so as to prevent or minimize disturbances in flow shear stress, eddy flow, foil effects, turbulence, resistance, tube wall deformation, and tensile stress/strain distributions that can lead to intimal hyperplasia and other similar or associated conditions. Similarly, as depicted in FIG. 1A, flange edge 140 may be chamfered to an angle, for example 60°, so as to similarly redirect fluid flowing within the source body space for the same purpose.

Multiple cutout regions 124 are disposed between longitudinal sections 112 and lateral sections 114. Cutout regions 124 represent an absence of material between those flanges 112, 114 and are dimensioned and configured to facilitate temporary foldover of flanges 112, 114 during implantation of flow connector 100. Sealing region 116 is also disposed over a portion of cutout regions 124 to ensure that the contact surface 126 around conduit body 130 is sealed with respect to the source body space so that fluids flowing through the source body space remains either within the source body space or through the lumen of conduit 104.

Figure 1F:
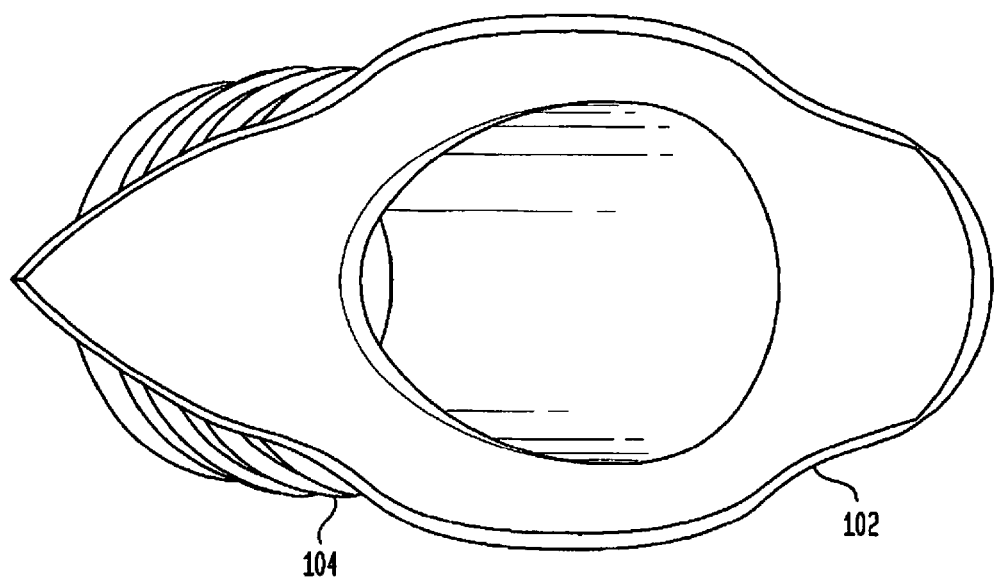
FIG. 1F is a further isometric view of the embodiment of the flow connector illustrated in FIG. 1C.

As noted above, flow connector 100 also comprises conduit 104 which is connected to flange 102 along joint region 106. At joint region 106, the proximal end 131 of conduit body 130 and flange 102 are joined such that first conduit orifice 120 leads into the lumen of conduit body 130, as illustrated in FIGS. 1E and 1F, which shows at least a partial view of exposed surface 128 of flange 102, as well as first conduit orifice 120 leading into the lumen of conduit body 130. In the embodiment illustrated in FIGS. 1A and 1B, conduit portion 106 is depicted largely as comprising a cylindrical conduit body 130. However, it is to be appreciated by one having ordinary skill in the art that conduit body 130 may have other shaped tubular bodies other than a cylindrical one in other embodiments of the present invention. For example, in other embodiments of the present invention, conduit body 130 may comprise a conduit body 130 with a rectangular or irregular cross section and a similarly shaped longitudinal lumen disposed therein. On the opposite end of conduit body 130 from proximal end 131 is distal end 132 of conduit body 130 as well as second conduit orifice 134 which is disposed at distal end 132. Second conduit orifice 134 allows fluid flow traveling through the lumen of conduit body 130 to exit through second conduit orifice 134. For example, in one embodiment of the present invention in which a source body space, such as a vein or artery, is coupled to conduit 104, fluid flowing through the source body space into which flange 102 is implanted is diverted through first conduit orifice 120, through the lumen of conduit body 130 and out of second conduit orifice 134 into the source body space.

Although the construction of flow connector 100 may vary depending on the one or more source conduits in which flow connector 100 is to be implanted, embodiments of the present invention may differ in terms of the material comprising flow connector 100, the durometer values of materials selected, thicknesses of the various components of flow connector 100 described herein or shown in the figures, and are considered a part of certain embodiments of the present invention. In one embodiment, flange 102 has a thickness ranging between approximately 0.15 mm and approximately 0.35 mm. Similarly, the outside diameter of conduit body 130 has a similar thickness range between approximately 0.15 mm and 0.50 mm and more preferably, of between approximately 0.30 mm and approximately 0.45 mm. In another embodiment, the outside diameter of conduit body 130 has a thickness of approximately 0.35 mm. The thickness of flange 102 may be decreased as flange 102 is made to extend further which will maintain the pullout forces necessary for flange 100 to be pulled out of the source body space in which it is implanted. Similarly, the thickness of flange 102 may be increased as the flange 102 is made to extend less.

Figure 5:
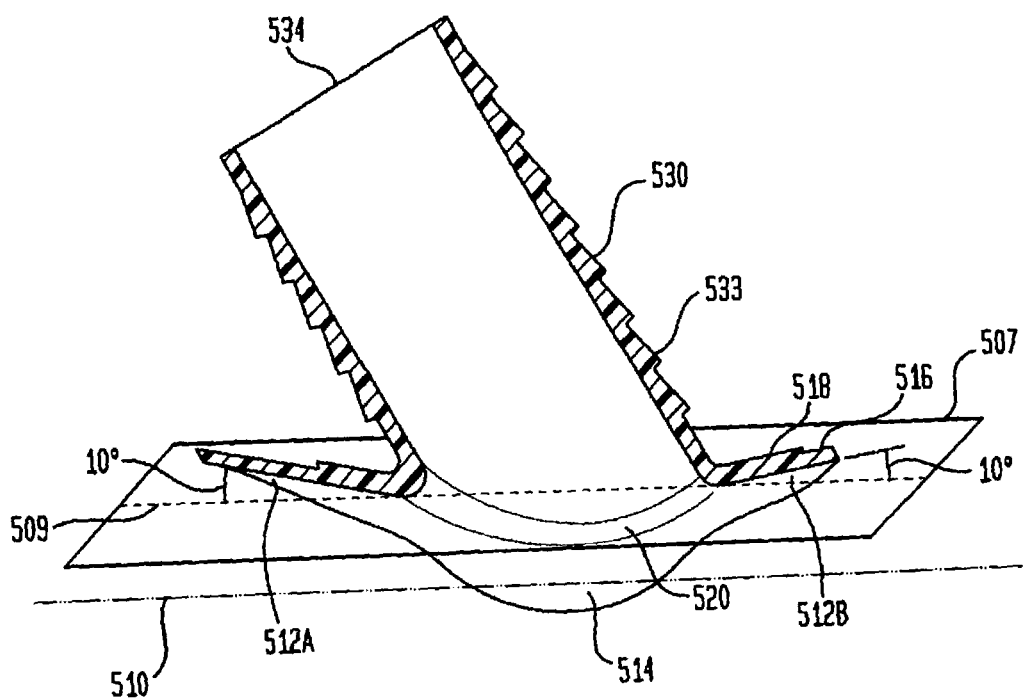
FIG. 5 is a cross-sectional view of one embodiment of the present invention with an imaginary plane having an imaginary midline.

As shown in FIG. 1C-1F and in cross-section in FIG. 5, conduit body 130 may comprise a series of barbs or protrusions 129 which extend radially from conduit body 130. In one embodiment of the present invention, the protrusions 129 provide periodic increases in the outside diameter of conduit body 130 so that the source body space within which conduit body 130 is inserted are positioned over conduit body 130 in a friction fit over the increased diameter portions of protrusions 131. Furthermore, once the source body space is positioned over conduit 104 over protrusions 131, one or more sutures may be disposed circumferentially around conduit body 130 and in the areas between, conduit body 130 and the outer diameter of protrusions 131, thereby snugly retaining the source body space in place with respect to conduit 104. When one or more sutures are thus disposed, the one or more sutures that compress the source body space towards the conduit portion 104 will maintain its position since the diameter of the one or more sutures are fixed to be smaller than the outer diameter of the protrusions, which therefore provides an interference fit to prevent the one or more sutures from translating along the longitudinal axis 108 of conduit body 130.

Figure 2A:
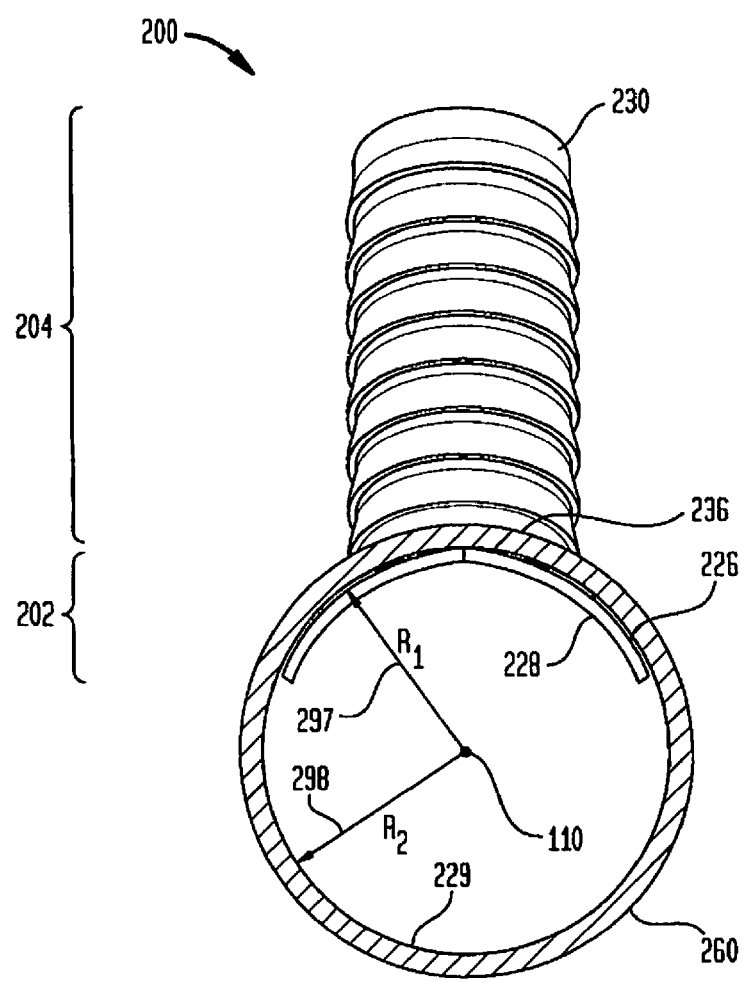
FIG. 2A is a cross-sectional view of a first tissue-enclosed body space in a recipient having one embodiment of the present invention implanted therein.
Figure 2B:
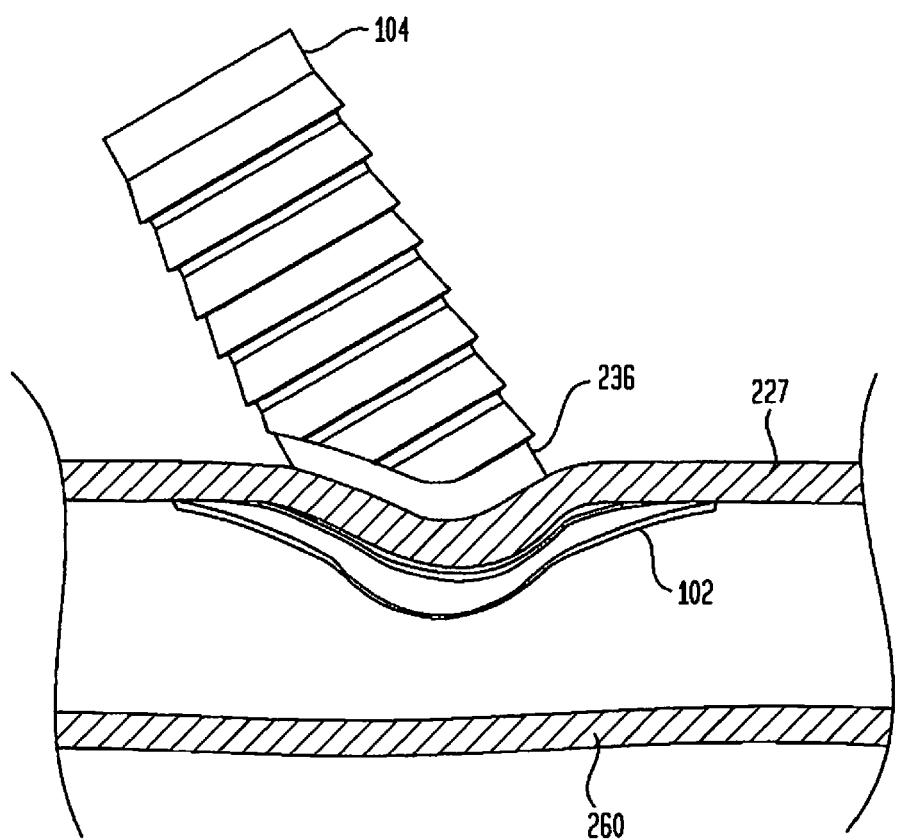
FIG. 2B is another cross-sectional view of a first tissue-enclosed body space in a recipient having one embodiment of the present invention implanted therein.

In certain embodiments of the present invention, conduit body 130, shown in FIGS. 2A and 2B as conduit body 230, has a conduit recess 236 disposed thereon. Conduit recess 236 is configured such that a source body space, such as source body space 260, rests within conduit recess 236 when flange 102, shown in FIGS. 2A and 2B as flange 202, is positioned within the source body space as described below. In one embodiment of the present invention, conduit recess 236 is configured to have a depth of between 0.5 mm and 1.0 mm in order to accommodate a source body space to allow it to rest therein. In other embodiments of the present invention, recess 236 may be configured to have a deeper recess, for example 1.0 mm. The height of the conduit recess 236, measured from flange 202 toward the distal end of conduit body 204 is approximately 0.8 mm, which will vary depending on the thickness of the source body space 260 which is accommodated within conduit recess 236, as depicted in FIG. 2A. Also as shown in FIG. 2B, conduit 204 of one embodiment of the present invention is shown to be angled approximately 60° from the horizontal axis in the illustration with respect to flange 202. This angle may vary in other embodiments of the present invention depending on the situation or the needs of the recipient. For example, in other embodiments of the present invention, conduit 204 may be configured with an angle between 10° to 90° from the horizontal axis shown in FIG. 2B. As one having skill in the art would appreciate, this angle can be from the opposite side as well with respect to flange 202.

As noted previously, flow connector 100, shown in FIG. 3 as flow connector 300, is configured to be at least partially placed within a source body space. In the embodiment illustrated in FIG. 3, flange 102 is configured to be positioned through an opening 303 on source body space 360. More specifically, one or more of heel section 312A, toe section 312B, and lateral sections 314A, B are temporarily deformed or bent with respect to flow connector 100 so that flange 102 can be inserted through opening 303. Opening 303 may be an existing opening or may be manually and/or intentionally formed, at least in part, to allow flange 102 to be inserted therethrough during the implantation of flow connector 300 within source body space 360. In the embodiment shown in FIG. 3, heel section 312A is longer than toe section 312B. The greater length of heel section 312A is configured to promote stability and the position of flange 102 within source body space 360. Additionally, the shorter length of toe section 312B, in the present embodiment of the invention, is configured to promote easier insertion of flange 102, especially in implantation methods where only lateral sections 314A, B are temporarily deformed, with longitudinal sections 312 inserted through opening 303 in their substantially extended position.

Figure 3:
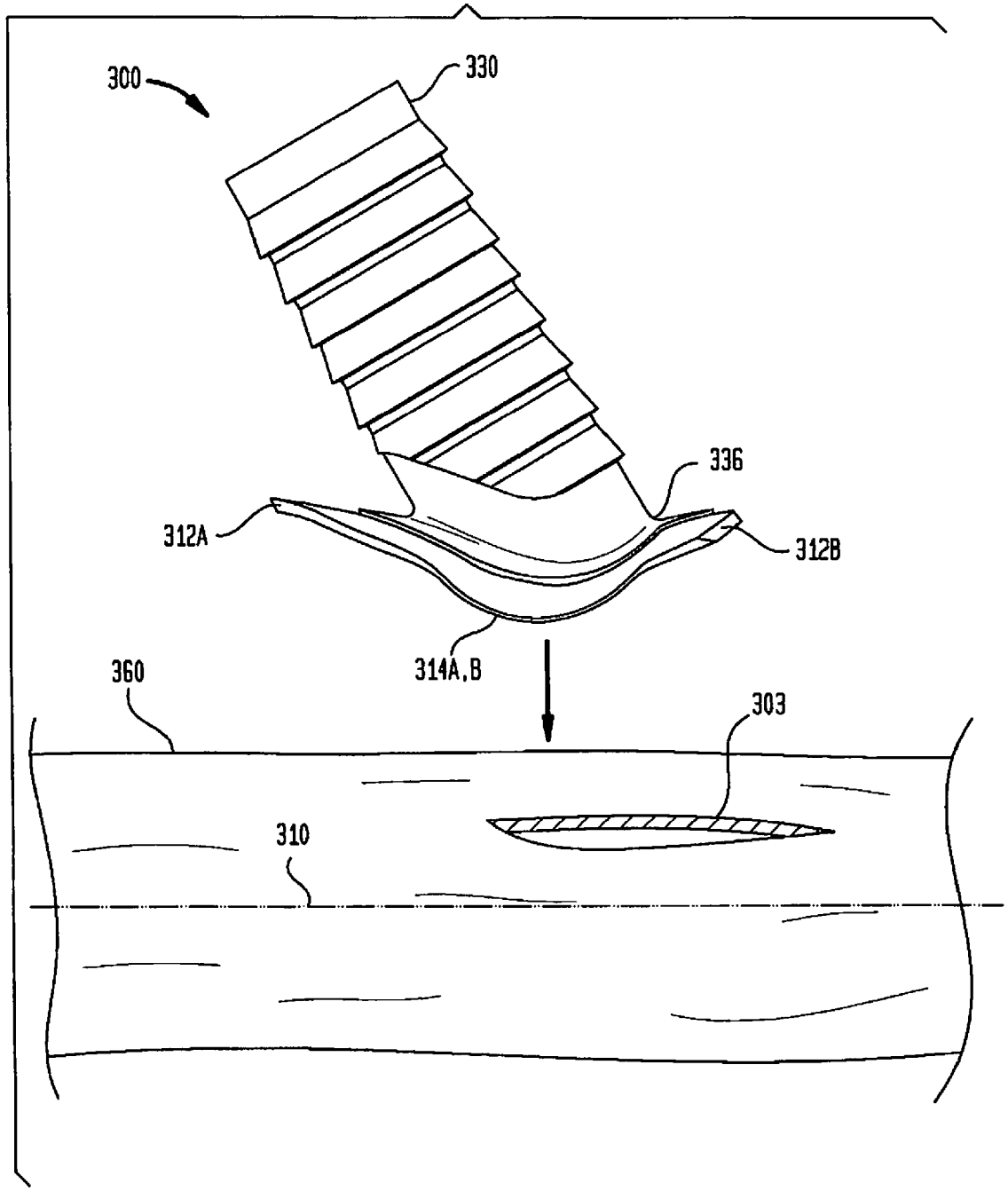
FIG. 3 is a perspective view of another embodiment of the flow connector of the present invention illustrated with respect to a tissue-enclosed body space into which the flow connector of the present invention is to be implanted.

In the embodiment illustrated in FIG. 3, the fluid flowing substantially along longitudinal axis 310 through source body space 360 is flowing from the direction of heel section 312A and flowing towards the direction of toe section 312B. As is seen in the embodiment illustrated in FIGS. 1 and 3, the longitudinal axis 108 of conduit body 130 is angled with respect to the longitudinal axis 310 of source body space 360 at an angle of approximately 60° towards to direction of heel section 312A. In this embodiment of the present invention, the 60° angled source body space 360 is provided to promote, among other things, a controlled rate and/or volume of fluid flow from source body space 360 into conduit body 330. In other embodiments of the present invention, that angle may not be 60°, but may instead be some other angle, depending on the placement of flow connector 300 within the recipient or the purpose for which flow connector 300 will be used once implanted. For example, in other embodiments of the present invention, conduit body 330 may be angled 90 or 120° with respect to longitudinal axis 310 in order to achieve a desired rate or volume of flow from source body space 360.

Figure 4:
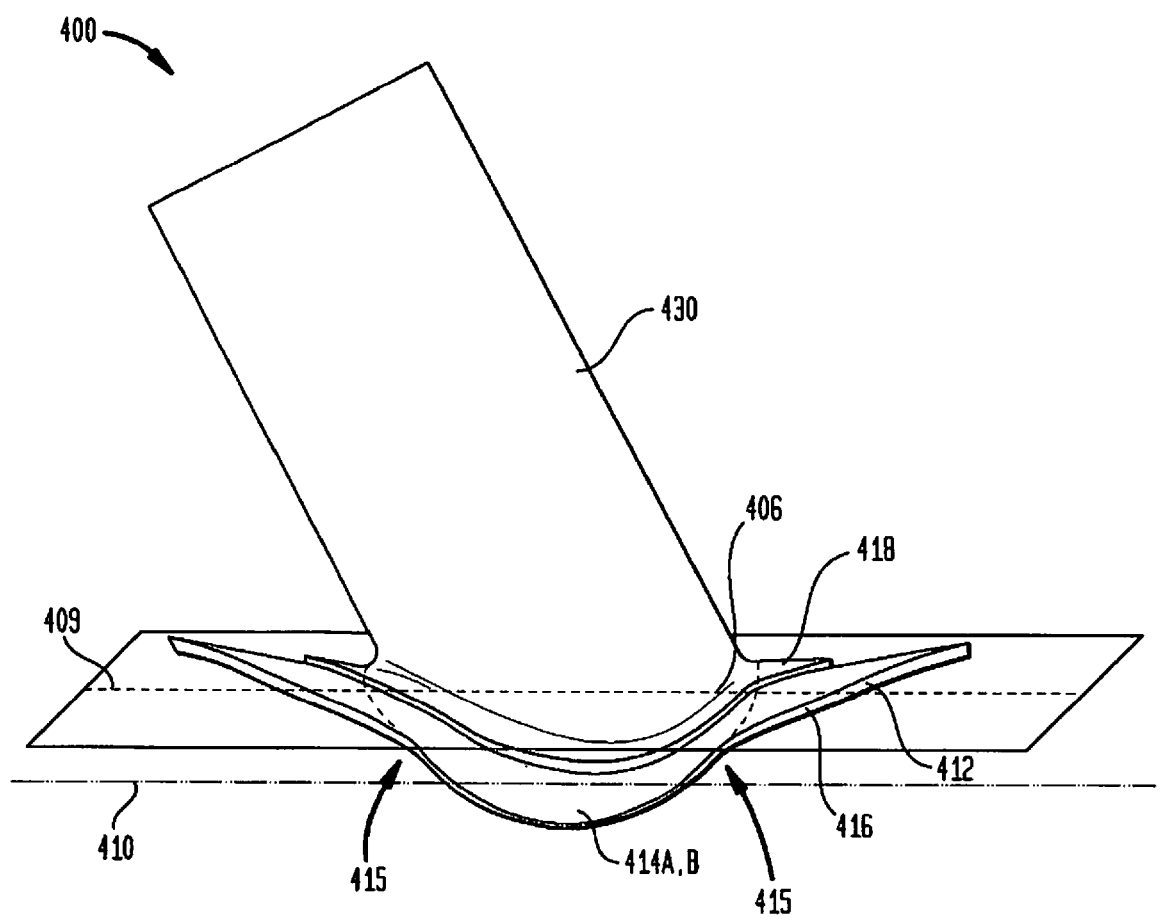
FIG. 4 is a perspective view of one embodiment of the present invention with an imaginary plane having an imaginary midline.

In FIGS. 4 and 5, an imaginary plane having a midline 409 is shown with respect to flow connector 400 and longitudinal axis 410 of source body space (not shown), according to one embodiment of the present invention. Midline 409 is parallel with respect to longitudinal axis 410 and is disposed on the exposed surface 128 around first conduit orifice 120. In the embodiment depicted, longitudinal sections 412 are angled upwards 10° from midline 409 starting at transition points 415 as shown. In other embodiments of the present invention, longitudinal sections 412 may be angled by a different amount, for example between 0 and 15°. The angling of longitudinal sections 412 upwards towards the inner surface of the source body space in which flow connector 400 is implanted will cause to be generated one or more deflection forces as a result of longitudinal sections 412 being pressed into the wall of the source body space. These deflection forces will cause a deflection of longitudinal sections 412 downward such that longitudinal sections 412 will be more parallel with midline 409 and longitudinal axis 410 of the source body space. This deflection downward will permit later flanges 414A, B to be disposed closer to the inner wall of the source body space than if the deflection did not occur, and will also cause a broader contact between contact surface 126 and the inside wall of the source body space once flow connector 400 is positioned within the source body space. FIG. 5 illustrates the imaginary line with midline 409, now shown as midline 509, as well as the 10° angling of longitudinal sections 412, now shown as longitudinal sections 512, with respect to longitudinal axis 510 of the source body space.

Figure 6:
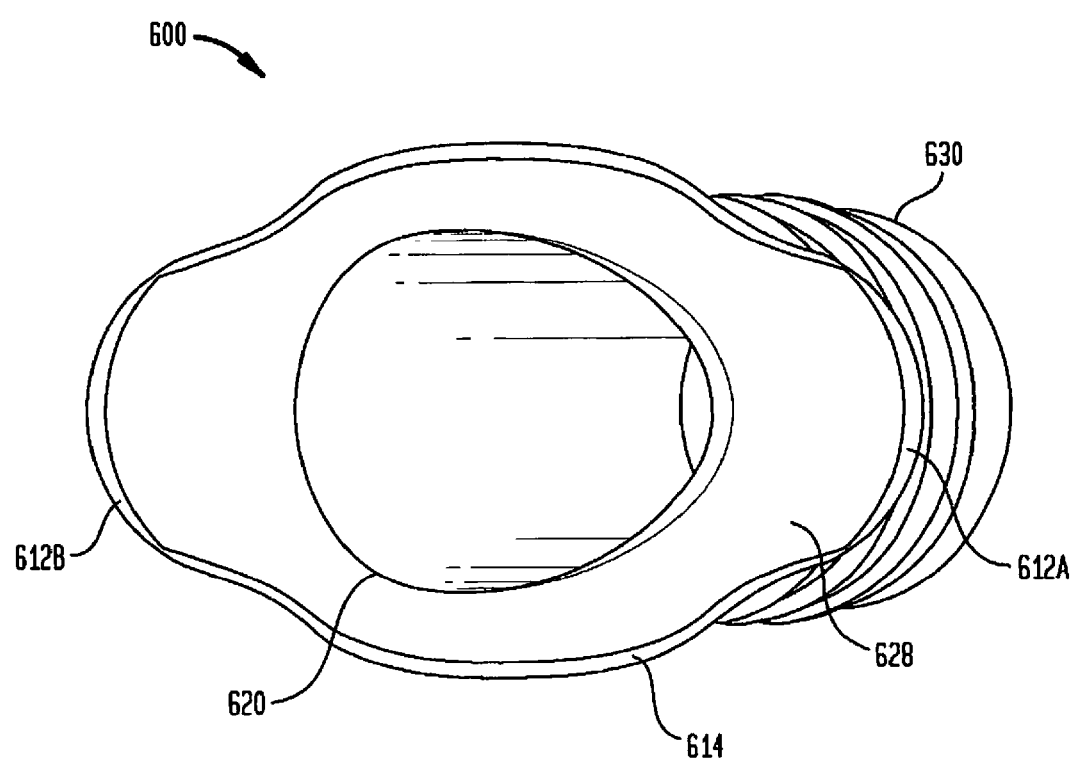
FIG. 6 illustrates a bottom view of another embodiment of the flow connector of the present invention.

Embodiments of the present invention include embodiments having different configurations of longitudinal and lateral sections. In the embodiment illustrated in FIG. 6, longitudinal sections 612A and 612B have about the same dimensions. In FIG. 6, heel section 612A is configured to be longer and to come to a pointed apex as illustrated. Toe section 612B is configured to be shorter than heel section 612A and has an apex which is more round than the apex of the heel section 612A. The shorter length of toe section 612B is sufficient, in cooperation with longer heel section 612A, to oppose the pullout forces described previously, while promoting easier insertion of flange 602 into the opening (not shown) of the source body space. In certain embodiments of the present invention, sections 612A, B are configured to each be approximately 35-65% in length of the outside diameter of first conduit orifice 620. In alternative embodiments of the present invention, sections 612A, B are each configured to be approximately 50% in length of the outside diameter of first conduit orifice 620.

Figure 7A:
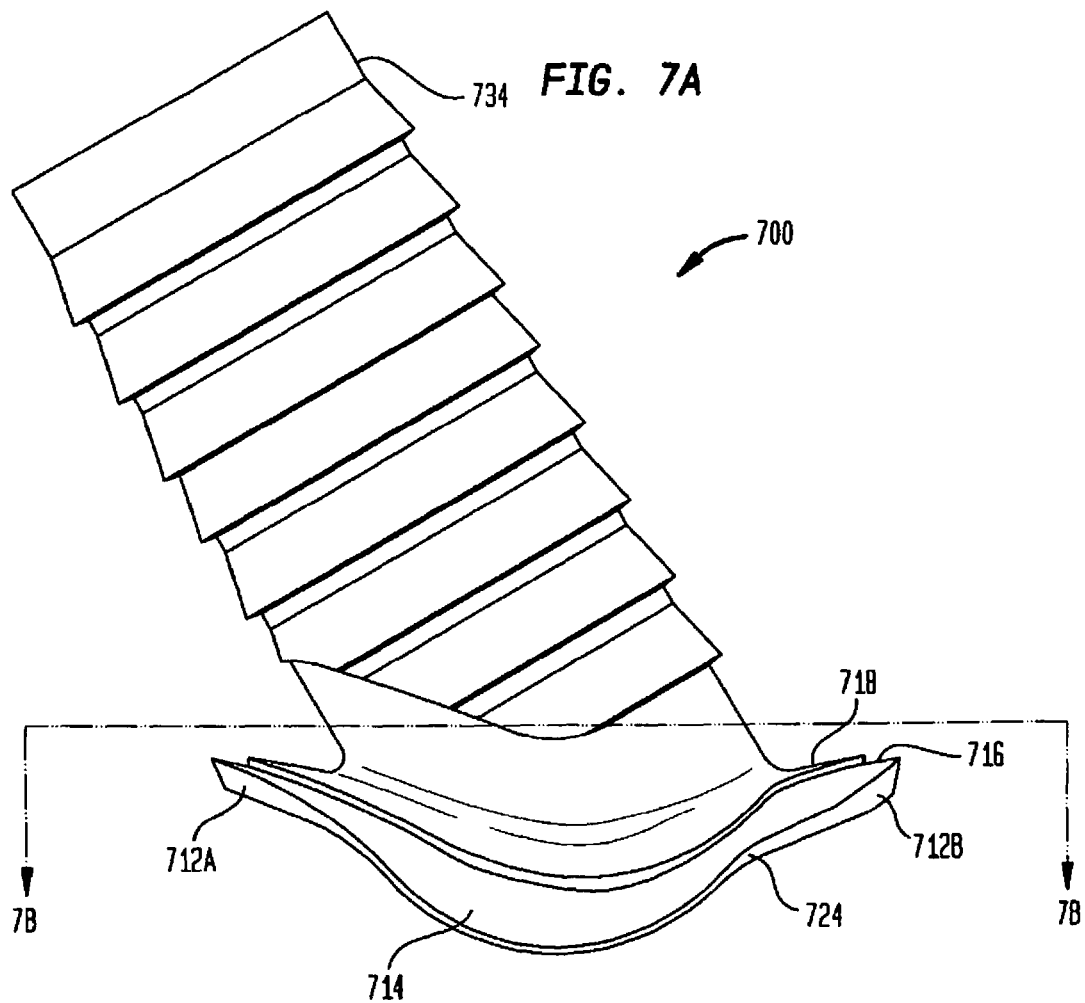
FIG. 7A illustrates a perspective view of an alternate embodiment of the flow connector of the present invention having shorter longitudinal sections than the embodiment illustrated in FIG. 1A.
Figure 7B:
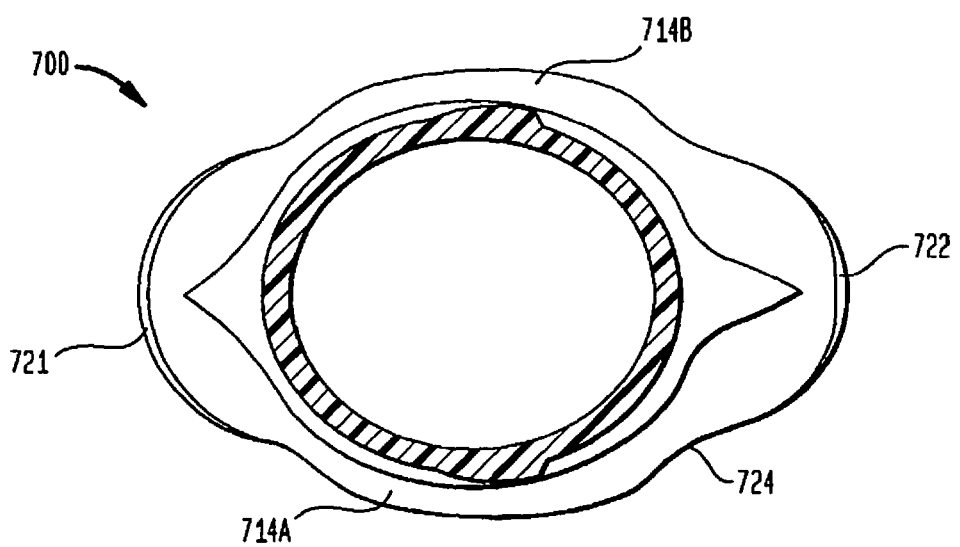
FIG. 7B illustrates a perspective top view of the embodiment of the flow connector illustrated in FIG. 7A.
Figure 8A:
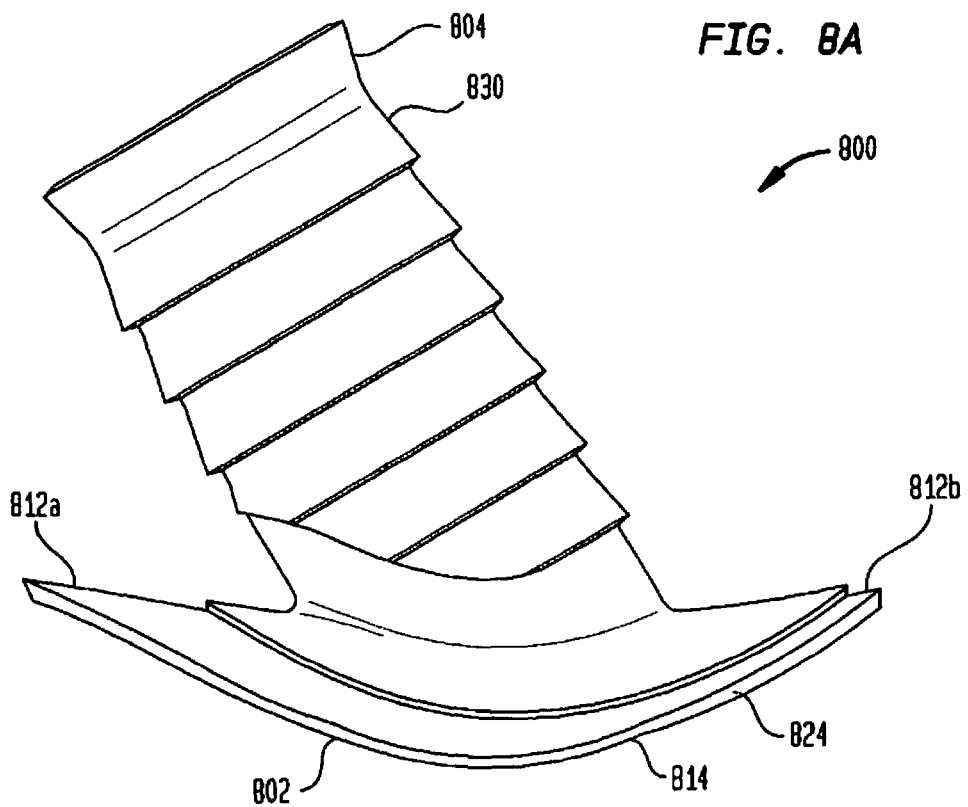
FIG. 8A is a simplified side of another embodiment of the present invention.
Figure 8B:
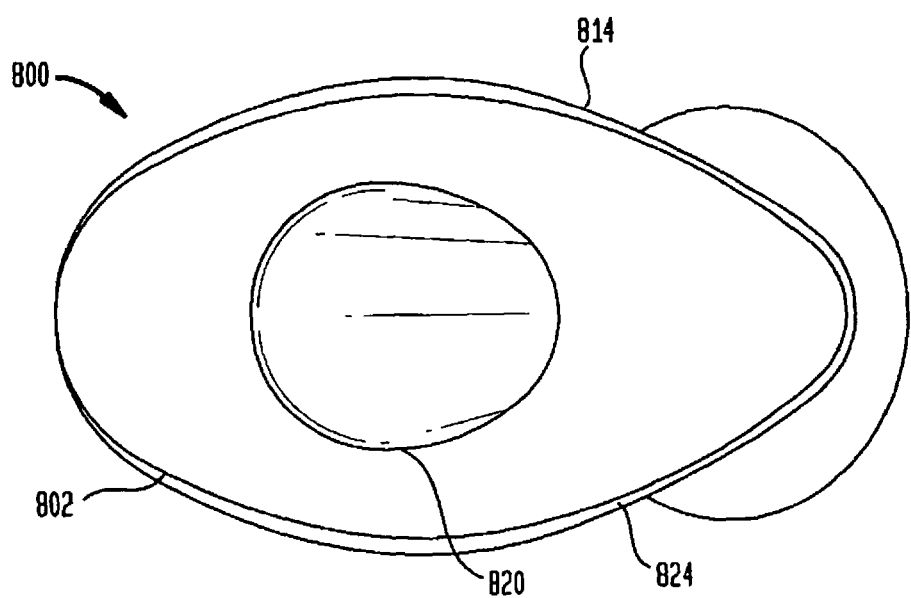
FIG. 8B is a simplified bottom view of another embodiment of the present invention.

Similarly, in the embodiment illustrated in FIGS. 7A and 7B, longitudinal sections 712 are configured substantially identically to one another. As shown, heel sections 712A and toe section 712B are both shorter than in other embodiments shown and described herein. FIG. 7B is a view along cross-section line 7B-7B and shows conduit body 730 as if it were partially removed from flow connector 700. The embodiment of the present invention illustrated in FIGS. 7A and 7B is appropriately configured and dimensioned so as to maintain the compensation for pullout forces by longitudinal and lateral sections 712 and 714, respectively. As noted previously, the thickness of sealing region 116 and reinforcement 118 may of flanges 712, 714 may be increased in order to provide make flanges 712, 714 more rigid. Alternatively, in other embodiments of the present invention, those components may be constructed of a more rigid material. FIGS. 7A and 7B also depicts cutout regions 724 which at least partly promotes flexibility of flanges 712, 714 as one or more of flanges 712, 714 are temporarily brought together during implantation of flow connector into the recipient's source body space, FIGS. 8A and 8B illustrates yet another embodiment of the present invention in which cutout region 824 has zero to little reduction in the material Which comprises the flange 802 of flow connector 800. Flange 802 may be constructed and dimensioned to be readily bendable upon receiving an external force, such as from a pickup tool being operated by a surgeon, despite having a very minimal or no absence of material in the cutout region 824. It should be understood by persons having skill in the art that cutout region 824, and other parts of flange 802 and conduit portion 804 may be modified before or during the implantation procedure, as will be further discussed below. Therefore, cutout region 824, or longitudinal sections 812 and lateral sections 814 may be modified in vivo to accommodate the dimensions of the source body space or the opening through which flange 802 is to be inserted during implantation of flow connector 800.

Figure 9A:
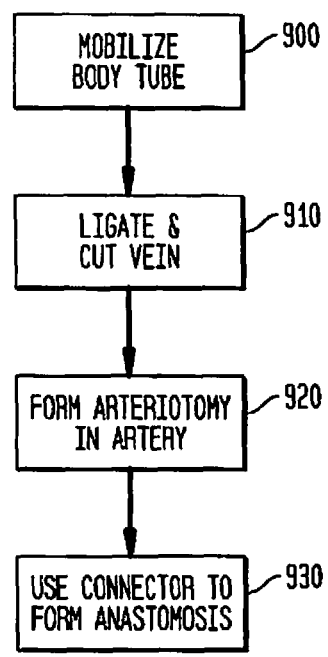
FIG. 9A is a high level flowchart of a method for implanting a flow connector according to one embodiment of the present invention.
Figure 9B:
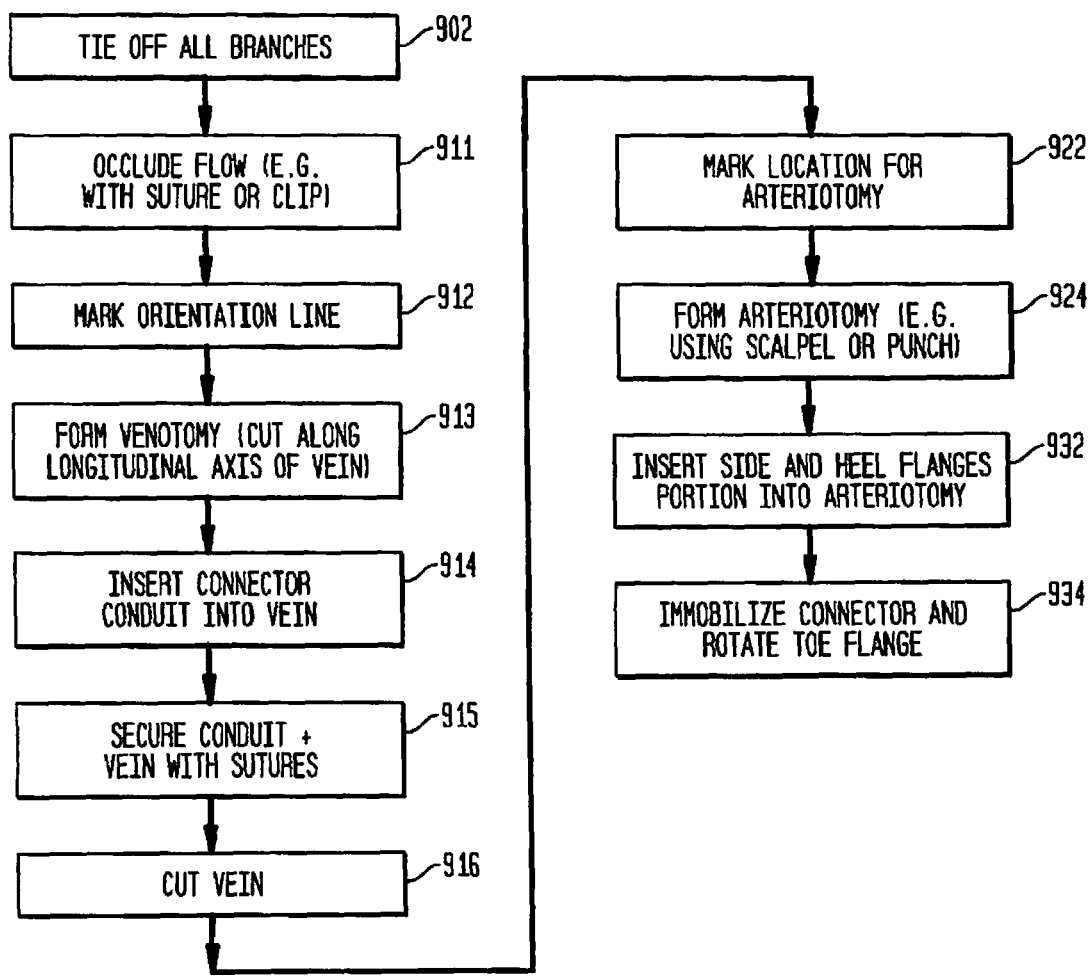
FIG. 9B is a detailed flowchart of one method for implanting the flow connector of the present invention, in accordance with one embodiment of the present invention.

In operation, embodiments of the present invention may be implanted in numerous ways. In one particular method of operation as depicted in FIG. 9A, the source body space is mobilized 900 from other conduits fluidically coupled to the destination body space. The destination body space, for example a vein of a recipient, is ligated and then cut 910 to receive the conduit 104 of flow connector 100. Once the destination body space has conduit 104 fitted therein, an opening is formed 920 in the source body space. Flange 102 of the flow connector, having the destination body space coupled thereto, is inserted through the formed opening in order to join 930 the source and destination body spaces together. In an alternate method, the flow connector is first inserted through the opening into the source body space and then the destination body space is placed over the flow connector.

Figure 10A:
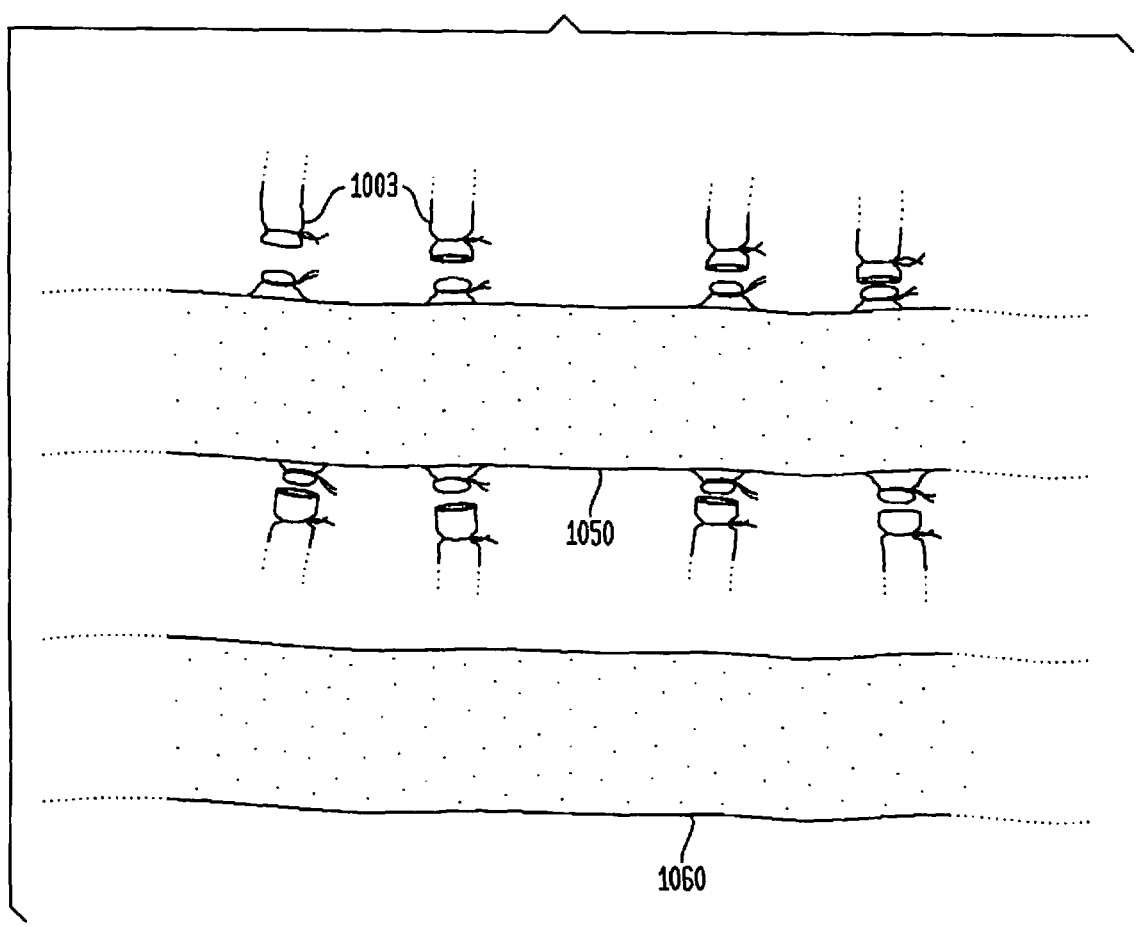
FIG. 10A illustrates tying off all branches from the second tissue-enclosed body space, according to one embodiment of the present invention.
Figure 10B:
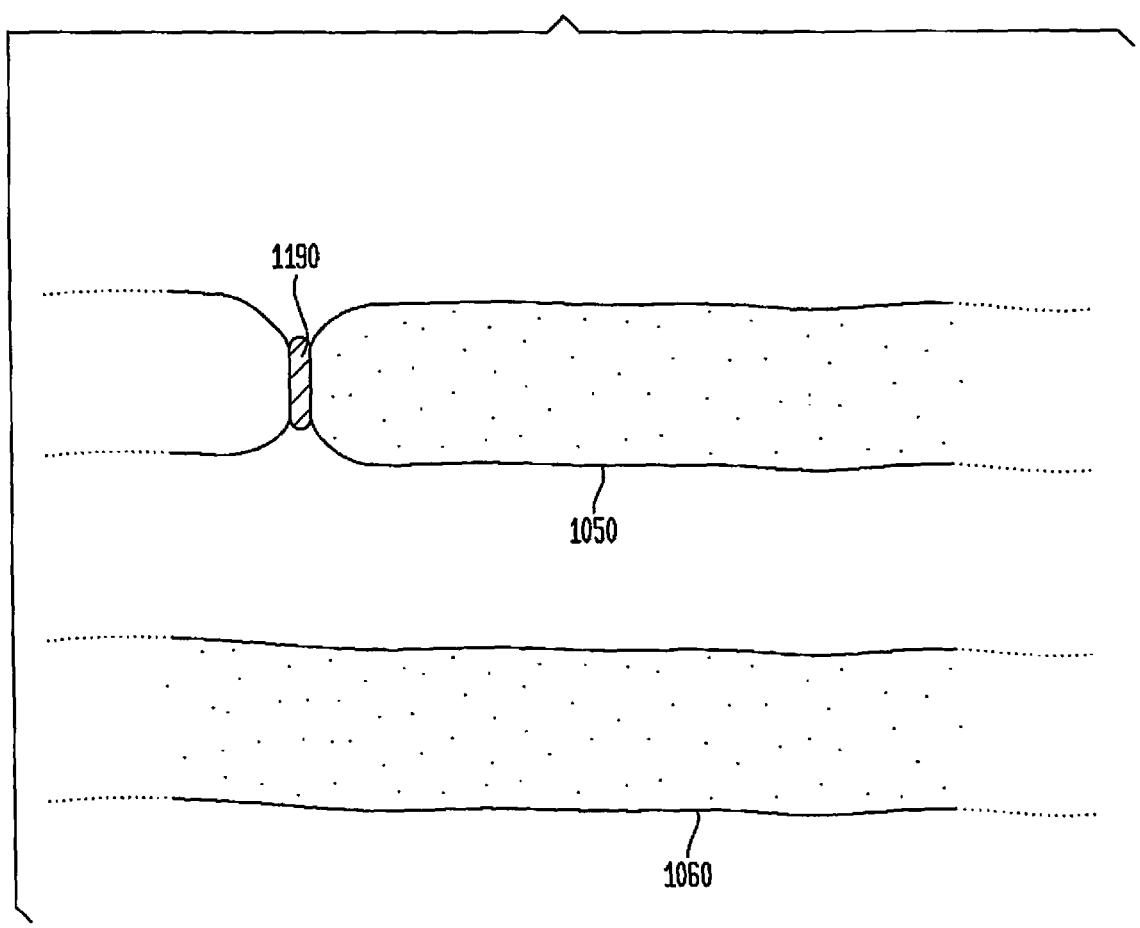
FIG. 10B illustrates occluding flow of liquids within the second tissue-enclosed body space.
Figure 10C:
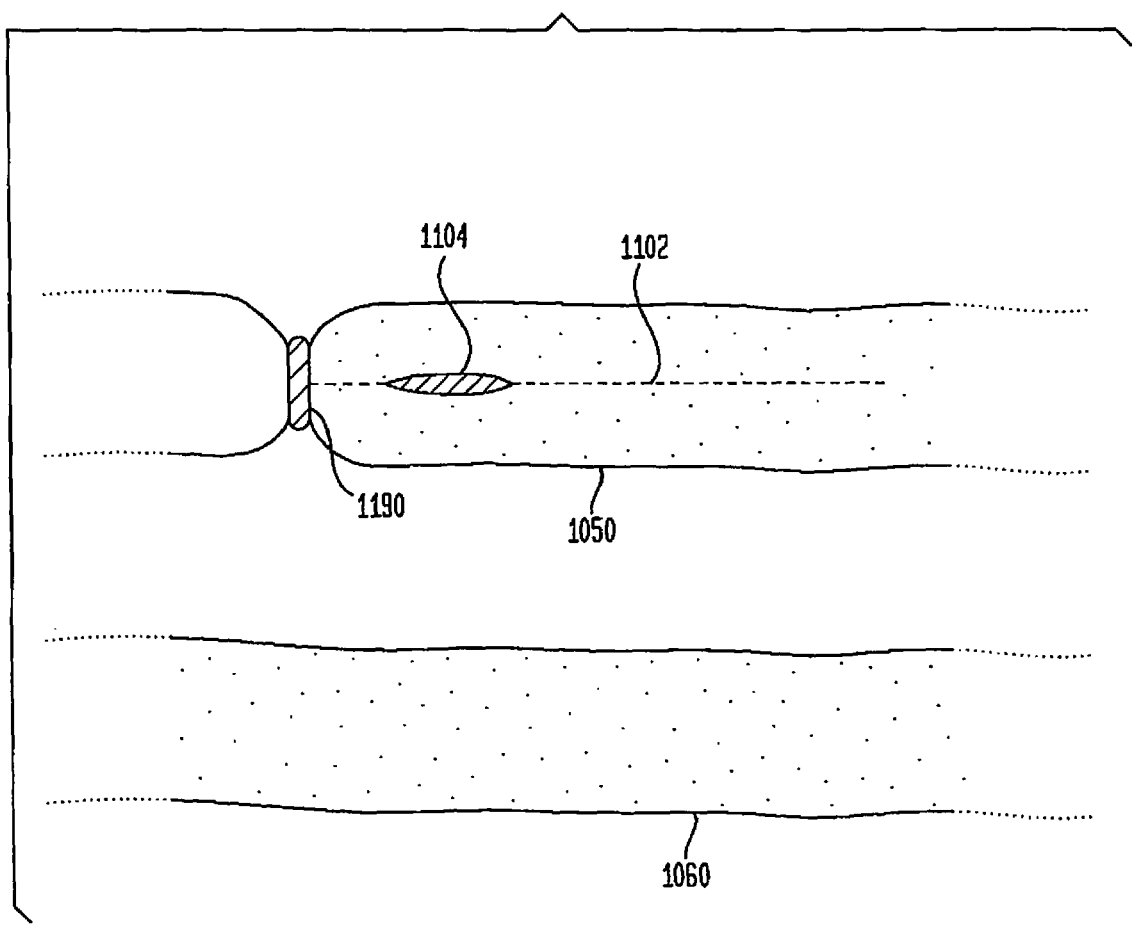
FIG. 10C illustrates marking an orientation line along the second tissue-enclosed body space and also forming an artificial opening on the second tissue-enclosed body space.
Figure 10D:
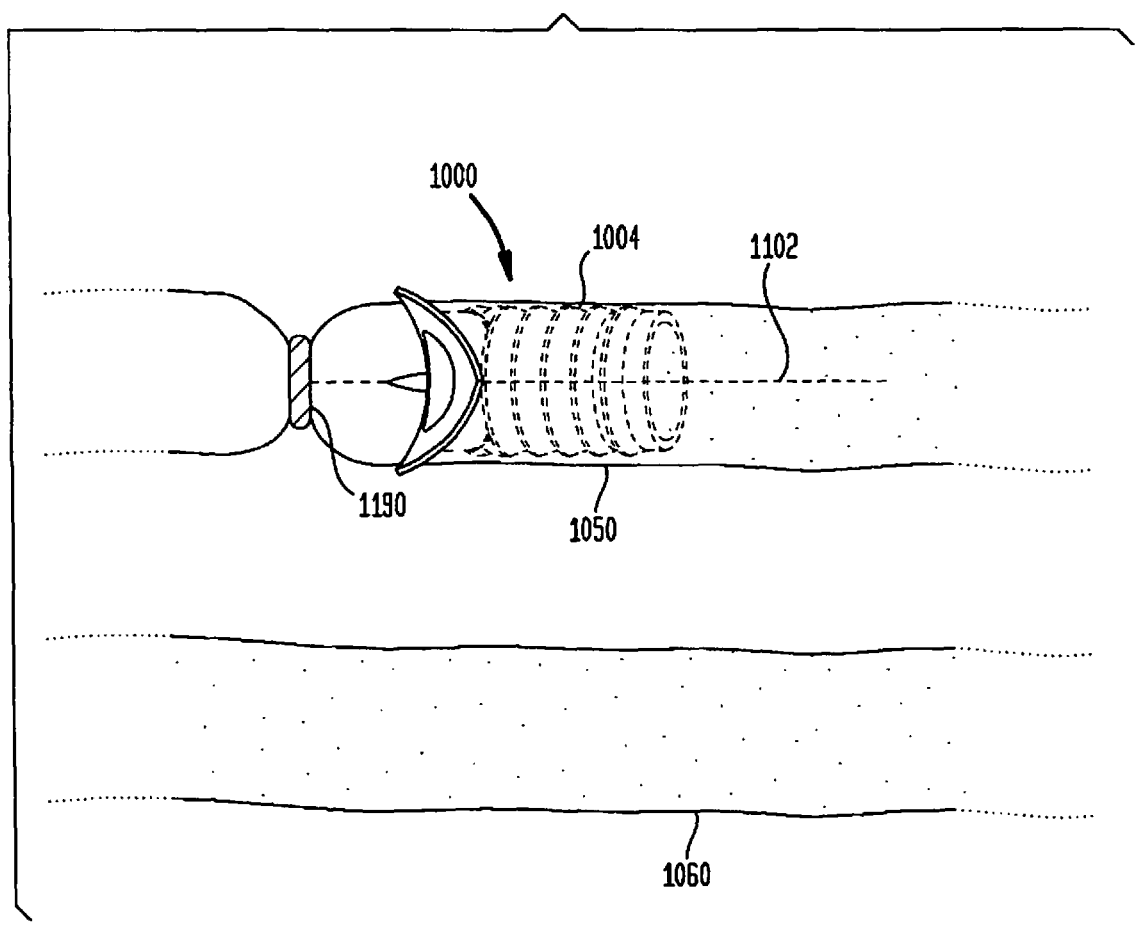
FIG. 10D illustrates inserting a flow connector according to one embodiment of the present invention in the second tissue-enclosed body space.
Figure 10E:
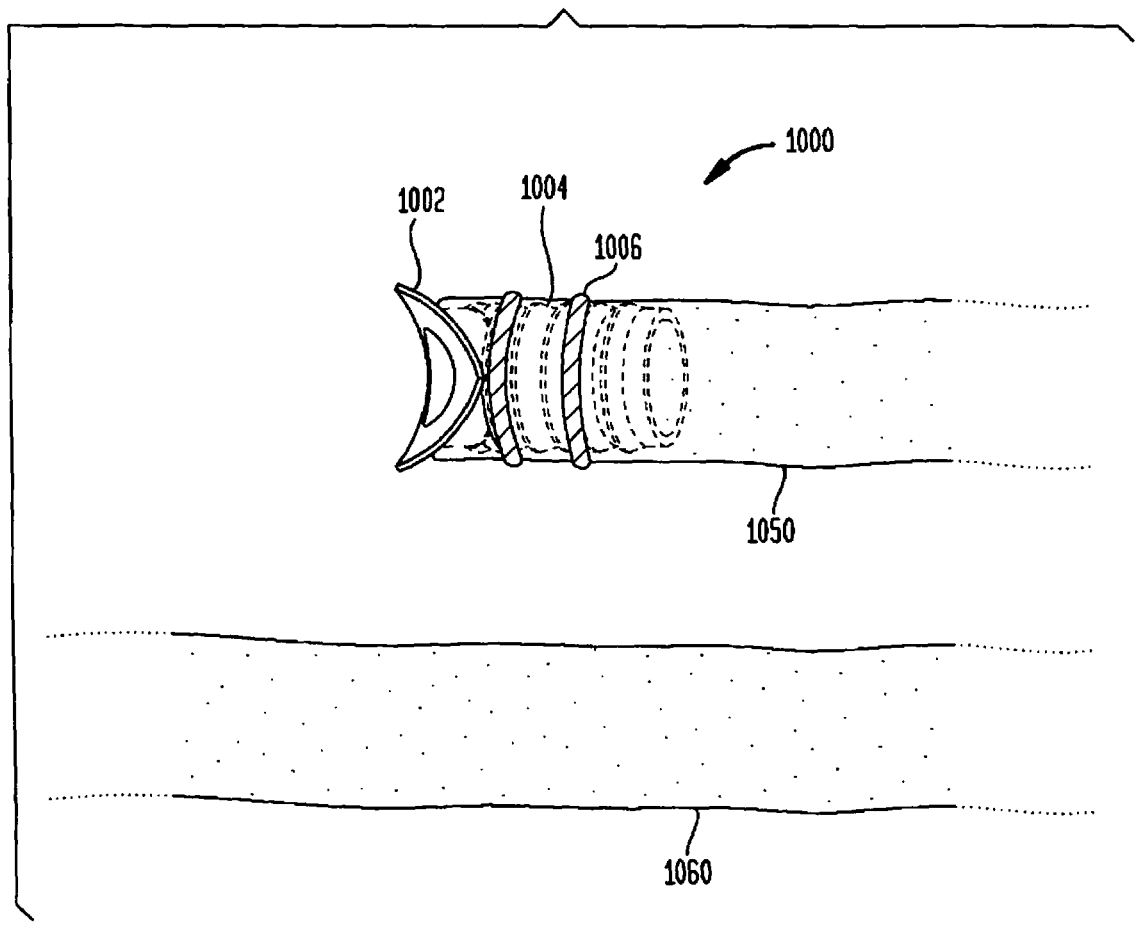
FIG. 10E illustrates a flow connector according to one embodiment of the present invention inserted and secured in a second tissue-enclosed body space with a portion of the second tissue-enclosed body space removed.
Figure 10F:
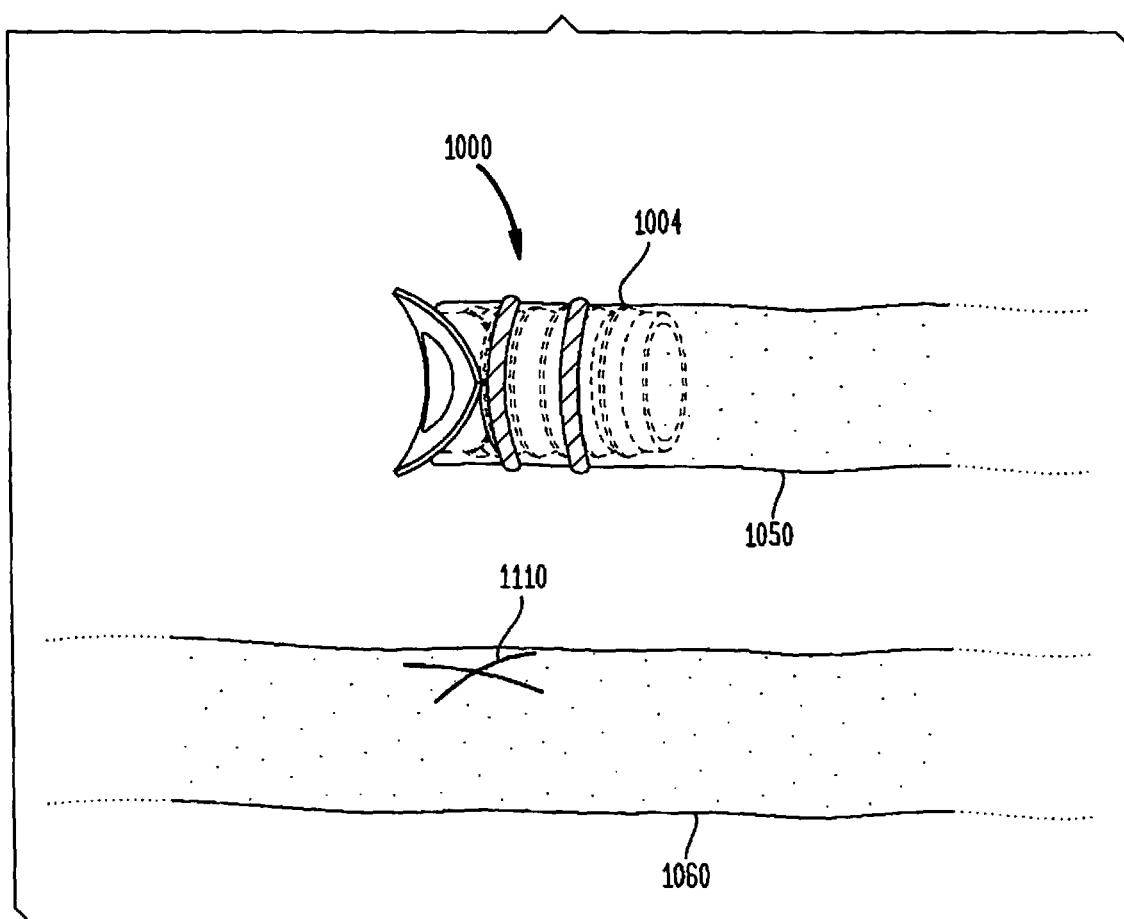
FIG. 10F illustrates marking a position on the first tissue-enclosed body space where an opening will be formed.
Figure 10G:
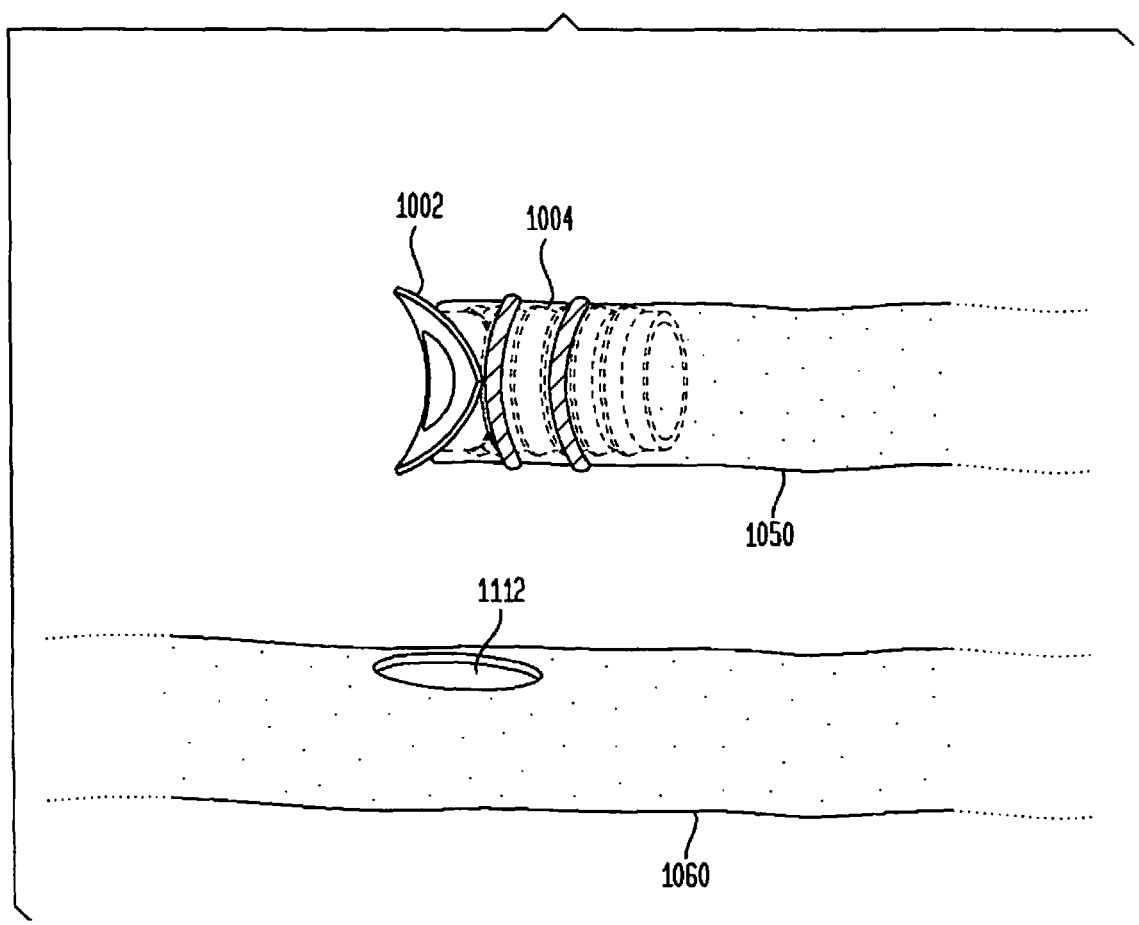
FIG. 10G illustrates a first issue-enclosed body space after an artificial opening is manually formed.

Expanding on the method outlined above and as further shown in FIGS. 9B and FIGS. 10A-10H generally, according one embodiment of the present invention, all branches 1003 of other conduits within the body of the recipient are severed or otherwise fluidically decoupled or tied-off 902 from destination body space 1050, as illustrated in FIG. 10A. As shown in FIG. 10B, destination body space 1050 itself is then tied-off or otherwise occluded 911 using a tie or suture 1100. FIG. 10C shows that an orientation line 1102 line is marked on destination body space 1050, and an opening 1104 is formed along orientation line 1102. As illustrated in FIG. 10D, conduit portion 102 of flow connector 1000 is inserted 914 through opening 1104. FIG. 10E illustrates two sutures 1006 which are secured onto destination body space 1050 prior to the occluded end being cut away 916 from the destination body space portion now having flow connector 1000 secured thereto. In FIG. 10F, a location is identified and marked 922 where an opening in source body space 1060 is to be formed. Once an opening 1112 is formed 924, as shown in FIG. 10G, flange 1002 of flow connector 1000 is inserted through opening 1112 and permitted to be securely retained within the walls of source body space 1060 in cooperation with lateral sections 114 and longitudinal sections 112.

Figure 14:
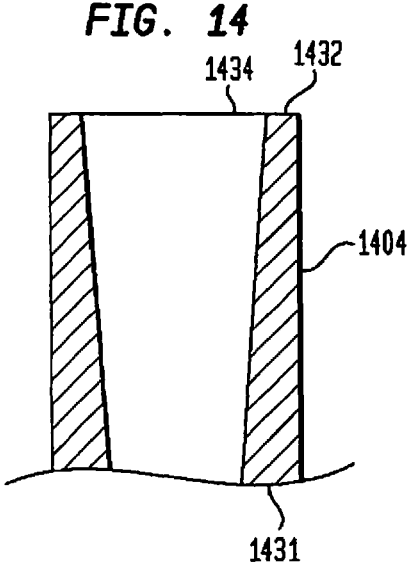
FIG. 14 is a cross-sectional view of a second interface according to yet another embodiment of the present invention in which the outer diameter remains substantially constant while the wall thickness decreases.

A cross-section of a portion of conduit 1404 according to one embodiment of the present invention is illustrated in FIG. 14. In FIG. 14, the portion shown illustrates a ramp configured to improve the flow from proximal end 1431 to distal end 1432 and out conduit orifice 1434 as it enters the destination element (not shown), for example a blood vessel. In FIG. 14, for the portion illustrated, the inside diameter of conduit 1404 gradually increases while the outside diameter of conduit 1404 remains substantially unchanged. By making the inside diameter of conduit 1404 substantially equal to the inside diameter of the destination element, the flow can across the cross-section of orifice 1434 is as uniform or consistent as possible, thus minimizing turbulence and other disturbances in flow which can lead to undesirable biological responses such as intimal hyperplasia. It will be understood that the ramp feature may be provided at either end of conduit 1404, to provide a smooth flow into and/or out of conduit 1404. For example, in one embodiment of the present invention, a ramp feature is disposed at both ends of conduit 1404 and promotes a smooth inflow of fluid into conduit 1404 for a limited length of conduit 1404, followed by a length of conduit 1404 in which the inside diameter remains constant, followed by a final distal length of conduit 1404 wherein a ramp having a gradually increasing inside diameter is provide and facilitates a non-turbulent outflow of the fluid out of conduit orifice 1434.

In other embodiments of the present invention, the outside diameter of conduit 1404 may change from the proximal end 1431 to distal end 1432. For example, in one embodiment, the outside diameter at each end may decrease gradually along its length. In another embodiment of the present invention, the outside diameter may increase gradually along its length. In yet further embodiments, the outside diameter may increase for some length, before decreasing for another length, and vice versa. As one having ordinary skill in the art will recognize, the outside diameter may be adjusted to be constantly or variably changing to meet specific needs or for specific uses.

In certain embodiments of the present invention, the second end of conduit 104 is configured to have an inside diameter approximately equal to the inside diameter of the destination element's lumen, for example the lumen in a blood vessel. As discussed previously, matching the inside diameters of the distal end of conduit 104 and the destination element at the point in each where fluid flow transitions from one to the other significantly reduces eddy current flow and other disturbances in the flow, which in turn reduces the occurrence of clots, thrombus, intimal hyperplasia, and other conditions which are largely undesirable. In other words, these features enable embodiments of the flow connector of the present invention to restore anatomical blood flow; that is, laminar flow, which is the normal condition for blood flow throughout most of the circulatory system. As one of ordinary skill in the art would appreciate, laminar flow is characterized by concentric layers of blood moving in parallel down the length of a blood vessel. In other words, the highest velocity is found in the center of the vessel while the lowest velocity is found along the vessel wall.

Other types of flow disturbances may include, but are not limited to, dead flow areas where a swirling or other types of flow pattern which deviates from a generally linear flow are formed by too steep of a step or diameter change with respect to certain factors such as the rate of flow, the viscosity of the fluid, the inside diameters of conduit 104 and the destination element, among others. In one embodiment of the present invention, conduit 104 has a chamfered distal end 132 or a gradually tapering distal end 132 in which the inside diameter gradually increases approaching the opening of the destination conduit. In another embodiment of the present invention, conduit 104 terminates at orifice 134 proximal the destination conduit at a knife-edge, where the wall thickness immediately proximal to the destination element approaches zero.

As illustrated in FIGS. 1F and 13-15, the inside surface of conduit 104 (also 1304, 1404, 1504), is a substantially frictionless surface configured to allow fluid flow over the surface without undergoing friction. This smooth surface minimizes or eliminates turbulence which might otherwise be generated during the flow through conduit 104.

Figure 10H:
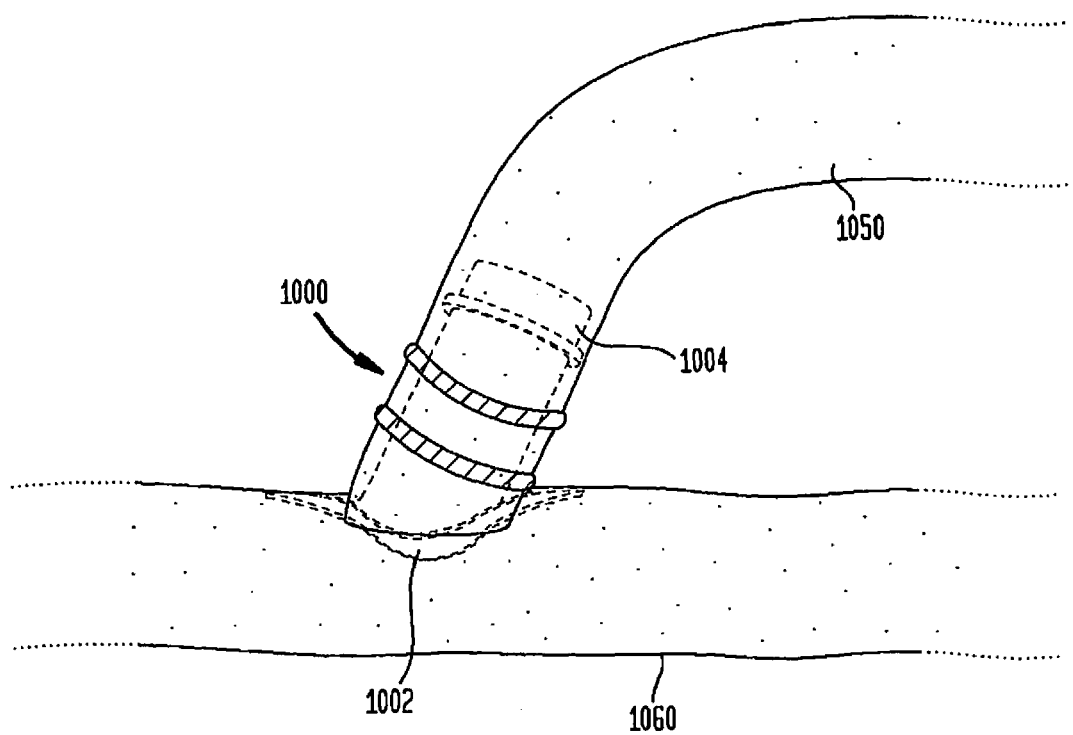
FIG. 10H illustrates a first tissue-enclosed body space connected to a second tissue-enclosed body space via one embodiment of the present invention.
Figure 12A:
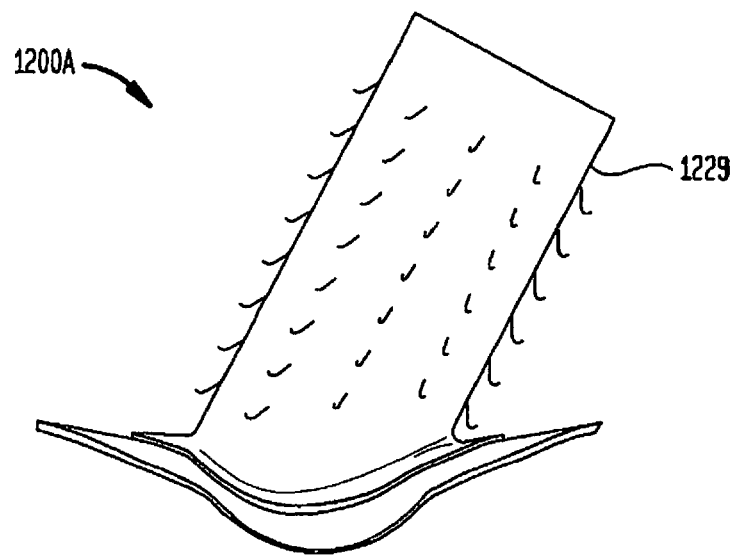
FIG. 12A illustrates another embodiment of the present invention in which the second interface further comprises barbs.
Figure 12B:
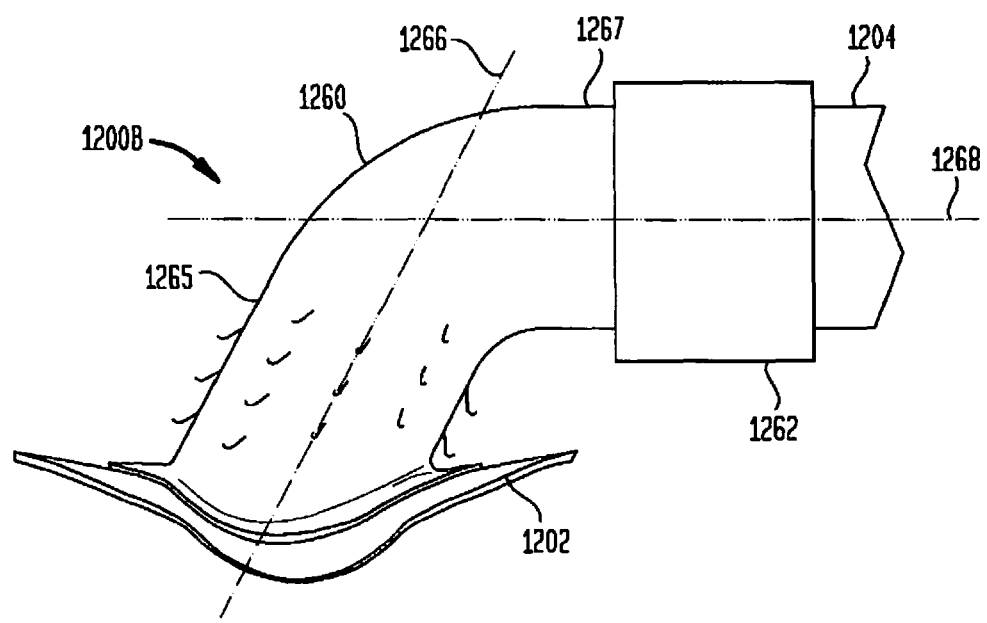
FIG. 12B illustrates yet another embodiment of the present invention in which the second interface comprises an elbow as well as a retention collar.

FIG. 12B illustrates another embodiment of the present invention in which bend 1260 is provided at a point along conduit 1204. The internal surface of bend 1260 in conduit 1204 redirects fluid flowing through conduit 1204, from flange 1202 to the destination elements, for example a blood vessel. In the embodiment illustrated in FIG. 12B, a first pre-bend longitudinal axis 1266 is shown as well as a second post-bend longitudinal axis 1268. In the illustrated embodiment, fluid flowing from flange 1202 through a first pre-bend portion 1265 is redirected by bend 1260 before the fluid enters a second post-bend portion 1267. While the fluid is thus redirected, conduit 1204 at bend 1260 absorbs the force from the fluid flowing towards bend 1260 as it is redirected towards the destination element (not shown), thus avoiding those forces being applied to a body vessel which would otherwise have received the forces. Using embodiments of the present invention having one or more bends 1260 as described, it is possible to provide an improved connection between the source body space and the destination element. For example, where the source body space is a artery and the destination element is a vein, as illustrated according to a different embodiment of the present invention in FIGS. 10A-10H, flow connector 1200B may be utilized to connect body space or vein 1050 with body space or artery 1060 but such that vein 1050 need not be bent as shown in FIG. 10H. Instead, connector 1200B is configured with a bend 1260 which would extend from artery 1060 and then bend towards the opening in vein 1050 such that vein 1050 remains substantially straight.

Figure 15:
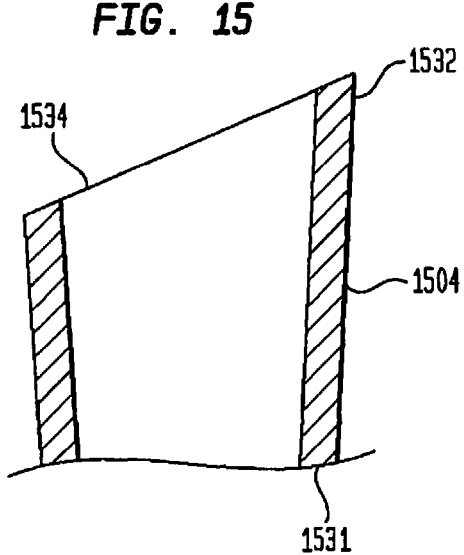
FIG. 15 is a cross-sectional view of a second interface according to yet another embodiment of the present invention in which the distal end of the second interface is uneven.
Figure 16:
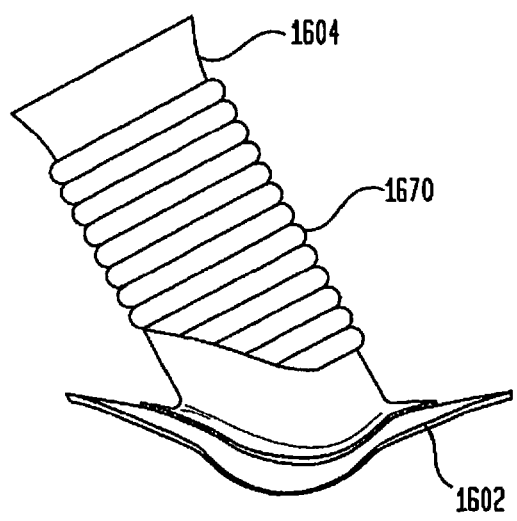
FIG. 16 illustrates an embodiment according to the present invention in which the first interface and second interface are formed separately and then joined together before implantation.

In further embodiments of the present invention, as illustrated in FIG. 15, distal end 1532 of conduit 1504 is beveled such that orifice 1534 at distal end 1532 is not 90° with respect to the longitudinal axis of conduit 1504. In the embodiment illustrated, the beveled distal end 1532 is approximately 30° from a plane orthogonal to the longitudinal axis of conduit 1504. However, a person having ordinary skill in the art will appreciate that the angle may be different depending on the situation in which an embodiment of the present invention is to be used. Beveled distal end 1532 facilitates a better transition of fluid flowing through conduit 1504 and exiting at beveled distal end 1532 into the destination element by accommodating a bend in the destination element by allowing an earlier exit of the fluid flow in the direction of the bend in conduit 1504. For example, the embodiment illustrated in FIG. 15 has a beveled end 1532 such that orifice 1534 is biased towards the left. This left-facing orifice 1534 may be used where the destination element is coupled to and extends up from conduit 1504 and bends towards the left. In addition to permitting an earlier exit from conduit 1504, beveled distal end 1532 also minimizes situations where a bend in the destination element, for example a conduit or blood vessel, causes the inside surface of the vessel to become constricted or reduced.

Figure 13:
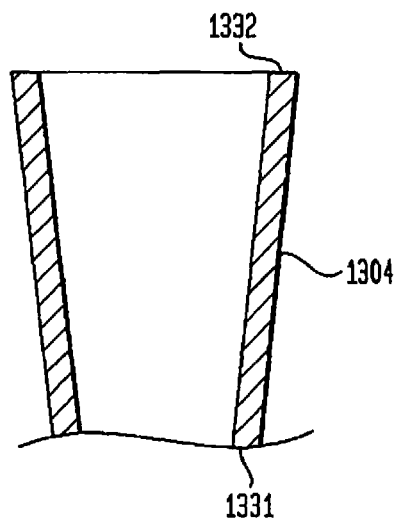
FIG. 13 is a cross-sectional view of a second interface according to one embodiment of the present invention in which the outer diameter increases while the wall thickness of the second interface remains substantially constant.

In yet further embodiments of the present invention, where the source body space and the destination element have different outside diameters, the outside diameters may be configured to accommodate the different outside diameters. As illustrated in FIG. 13, according to one such embodiment of the present invention, the outside diameter of conduit 1304 may vary from its proximal end 1331 to its distal end 1332. As shown, the inside diameter of conduit 1304 may also increase at the same rate as the change in the outside diameter of conduit 1304. However, it is to be understood that in other embodiments of the present invention, the inside diameter may change at a different rate, or not at all, as the change in the outside diameter.

Figure 17A:
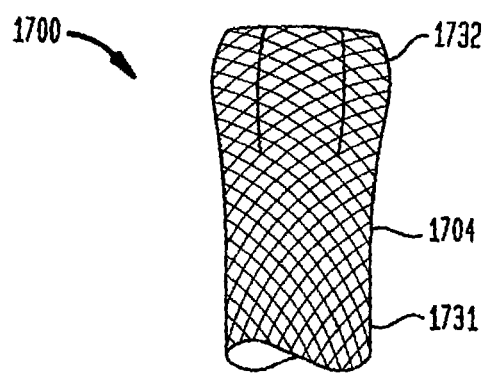
FIG. 17A is a perspective view of the second interface of a flow connector according to one embodiment of the present invention in its naturally collapsed state prior to implantation.
Figure 17B:
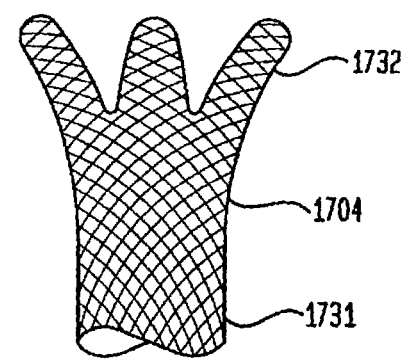
FIG. 17B is a perspective view of the second interface of a flow connector according to one embodiment of the present invention in its expanded state after implantation and forced expansion.

As shown in FIGS. 17A, B, and 18A, B, according to other embodiments of the present invention, flow connector 1700 and 1800 may be configured to be collapsible (FIGS. 17A, B) or expandable (FIG. 18A, B) to further accommodate differences in the inside diameters of the source body space and the destination element. Furthermore, the collapsible and expandable embodiments may be used to assist implantation by implanting conduit 1704, 1804 while having a reduced physical size and then being forced (or being allowed) to take on a larger shape to fit, for example seal and retain, the destination or source body space. Conduits 1704 and 1804 may be composed of a mesh material which has various joints or hinges or other manipulable series of parts which permit the overall shape of conduit 1704 and 1804 to be manipulated. Expandable conduit 1704 may be configured with a small cross-sectional shape, as illustrated in FIG. 17A and later forced to take on and retain an expanded cross-sectional shape, as illustrated in FIG. 17B. In one embodiment of the present invention, expandable conduit 1704 may be expanded with a balloon inserted into implanted conduit 1704 and expanded. In another embodiment of the present invention, expandable conduit 1704 may have a mechanical expanding force applied at a proximal end 1731 which is communicated through the expanding portion of conduit 1704 in order to open conduit 1704 as illustrated in FIG. 17B. In the embodiment illustrated, conduit 1704 comprises finger-like portions which overlap one another as illustrated in FIG. 17A but which expand and separate as illustrated in FIG. 17B. It is to be understood that a portion of the finger-like portions may be used to retain the destination body space while a different portion may be used to provide a seal between conduit 1704 and the destination body space.

Figure 18A:
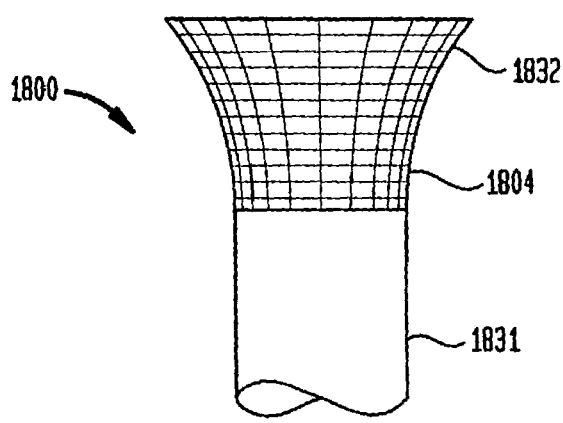
FIG. 18A is a perspective view of the second interface of a flow connector according to yet another embodiment of the present invention in its naturally expanded state prior to implantation.
Figure 18B:
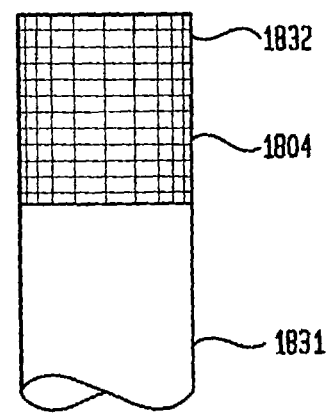
FIG. 18B is a perspective view of the second interface of a flow connector according to yet another embodiment of the present invention in its forced collapsed state, ready for implantation in the recipient.

Similarly, collapsible conduit 1804 may be configured with a shape-memory material, in a mesh or other configuration, which is expanded at rest but can be made to collapse when sufficient force is applied to it. As shown in FIGS. 18A, B, a portion of conduit 1804 may comprise the collapsible portion while another portion may be a non-collapsible portion. In one embodiment of the present invention, collapsible conduit 1804 may be disposed in a delivery tube (not shown) which is configured to receive conduit 1804 in a collapsed position before being inserted and then delivered in a destination body space. In another embodiment of the present invention, delivery tube (not shown) may be made of a resorbable material such that collapsible conduit 1804 may be delivered into the destination body conduit within the resorbable delivery tube. Subsequent to delivery, the resorbable delivery tube begins to be resorbed and cause the collapsible conduit 1804 to be released and permitted to return to its naturally expanded configuration.

Figure 11A:
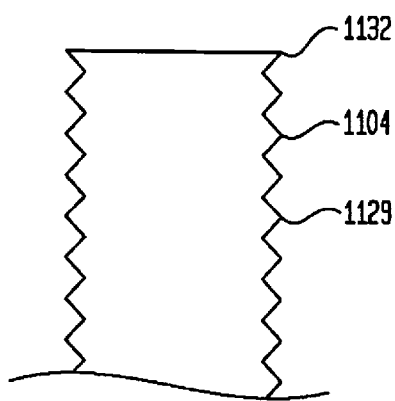
FIG. 11A illustrates a simplified schematic view of a portion of the second interface according to one embodiment of the present invention.
Figure 11B:
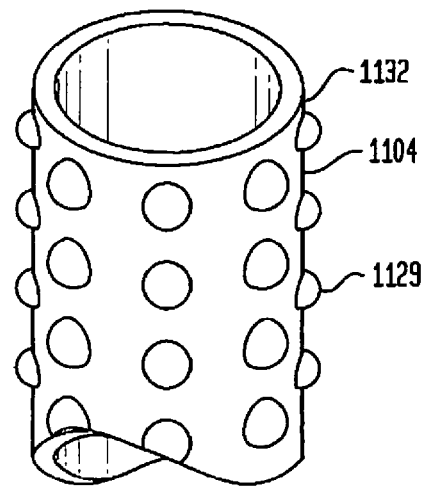
FIG. 11B illustrates a perspective view of a portion of the second interface according to a further embodiment of the present invention.
Figure 11C:
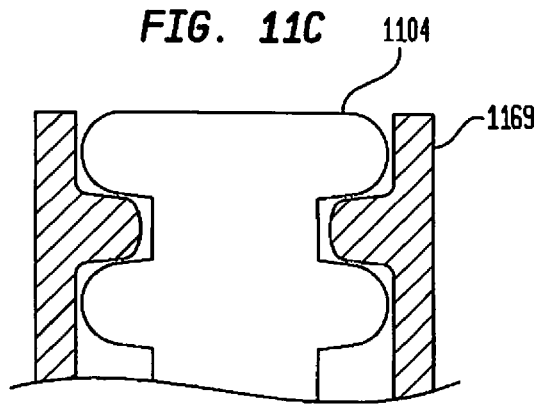
FIG. 11C illustrates a cross-sectional view of a portion of the second interface according to another embodiment of the present invention.
Figure 11D:
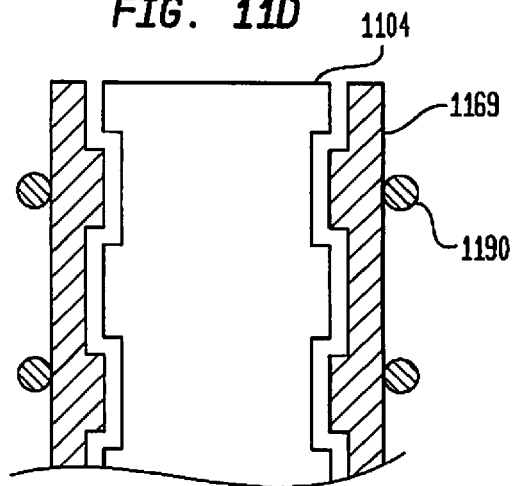
FIG. 11D illustrates a cross-sectional view of a portion of the second interface according to a yet further embodiment of the present invention.
Figure 11E:
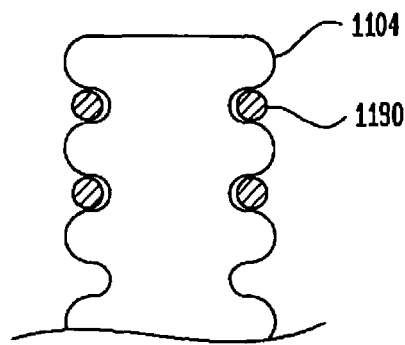
FIG. 11E illustrates a cross-sectional view of a portion of the second interface according to another embodiment of the present invention.
Figure 11F:
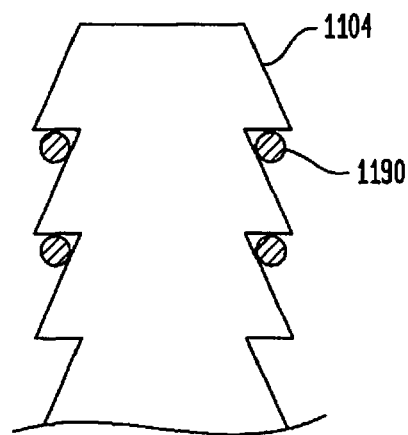
FIG. 11F illustrates a cross-sectional view of a portion of the second interface according to yet another embodiment of the present invention.
Figure 11G:
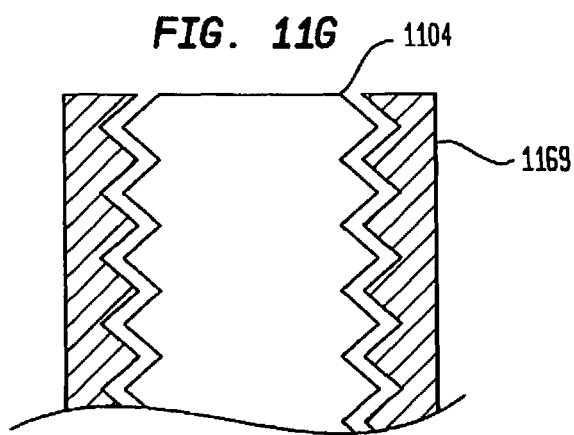
FIG. 11G illustrates a cross-sectional view of a portion of the second interface according to a further embodiment of the present invention.
Figure 11H:
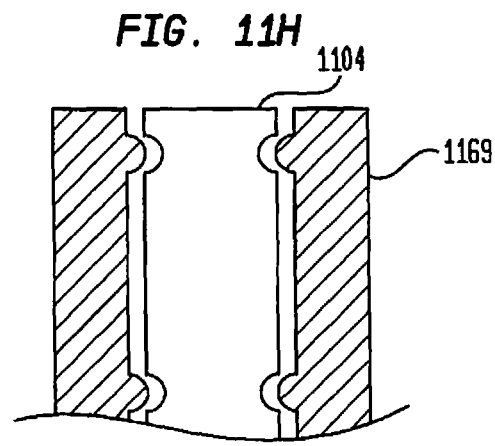
FIG. 11H illustrates a cross-sectional view of a portion of the second interface according to a yet further embodiment of the present invention.
Figure 11I:
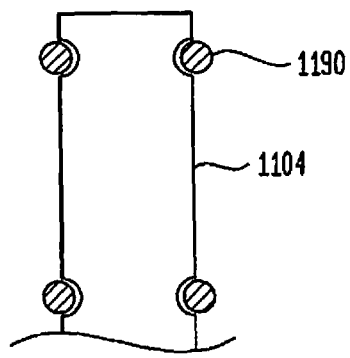
FIG. 11I illustrates a cross-sectional view of a portion of the second interface according to another embodiment of the present invention.
Figure 11J:
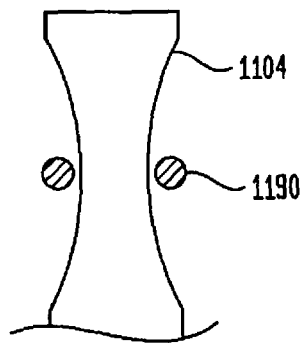
FIG. 11J illustrates a cross-sectional view of a portion of the second interface according to yet another embodiment of the present invention.
Figure 11K:
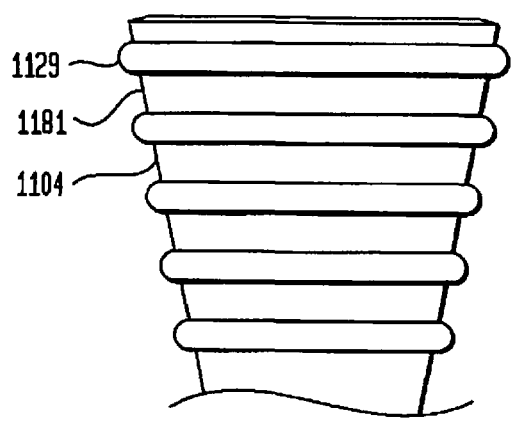
FIG. 11K illustrates a perspective view of a portion of the second interface according to one embodiment of the present invention.
Figure 11L:
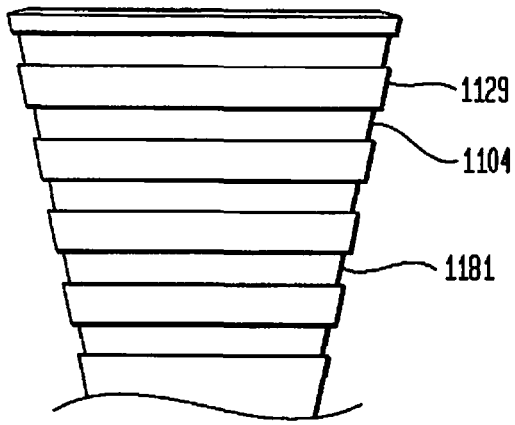
FIG. 11L illustrates a perspective view of a portion of the second interface according to another embodiment of the present invention.

According to embodiments of the present invention, as illustrated in FIGS. 11K and 11L, conduit 1104 may be modified or reduced subsequent to factory manufacturing. For example, according to one embodiment of the present invention, conduit 1104 is configured to allow a surgeon in vivo to evaluate the opening in the destination element, for example a vein, into which the distal end of conduit 1104 is to be inserted. After mentally or physically marking where the conduit 1104 is to be reduced, the surgeon cuts away material from distal end 132 in order to better fit flow connector 100 into the destination element. In other embodiments of the present invention, conduit 1104 may be configured with perforations adjacent one or more recesses 1181 or visual markers such as protrusions 1129 which can aid in the measuring of the portion to be cut or removed. In certain embodiments of the present invention, markers on the outside of conduit 1104 facilitate cutting of conduit 1104 at increments of 0.25 mm, 0.5 mm or 1.0 mm, or variations thereof. In other embodiments of the present invention, perforations along conduit 1104 are provided to facilitate in the cutting or otherwise modifying conduit 1104 at those increments of 0.25 mm, 0.5 mm or 1.0 mm, or variations thereof. Conduit 1104 may be constructed of a material that is resiliently flexible, such as silicone or other materials that are resiliently flexible, as will be appreciated by a person having ordinary skill in the art. Alternatively, conduit 1104 may be constructed of one or more materials so as to be rigid or hard, thus necessitating different tools in order to reduce or otherwise modify it than in embodiments of the present in which conduit 1104 is resiliently flexible.

Additionally, certain embodiments of the present invention may have one or more active elements in conduit 104 or flange 102 which are configured and arranged to provide one or more therapeutic benefits. For example, in one embodiment of the present invention, flow connector 100 is constructed of a material so that one or more portions of flow connector 100 is radiopaque. In other embodiments of the present invention, the active element is one or more drug compounds or pharmaceutical materials configured to be released by flow connector 100 and to act on into the area near the flow connector or systemically throughout the recipient. In certain embodiments of the present invention, the one or more pharmaceutical materials may be configured to require heat or fluid-contact activation in order to begin its being released. In other embodiments of the present invention, the pharmaceutical materials on flow connector 100 is further configured to be time-released such that the compounds therein are released gradually over a period of time at a constant or varying rates of release. In yet further embodiments of the present invention, the active element comprises pharmaceutical materials disposed within a heat or fluid-contact activated dissolving capsule shell.

As shown in FIG. 12B, other embodiments of the present invention may comprise a malleable conduit 1204 configured to take on and hold a different configuration upon receiving sufficient external force. For example, in one embodiment of the present invention, the surgeon may apply a bending force to conduit 1204 in order to accommodate the source and destination body conduits. Upon receiving sufficient bending force from the surgeon, conduit 1204 will retain the bend and direct or channel fluid flowing therethrough according to the shape, specifically the internal surface, of conduit 1204. Malleable conduit 1204 is configured from a mesh or other structure having cooperating elements such as shape memory metals which allow malleable conduit 1204 to retain a shape upon receiving the bending force described.

Figure 11M:
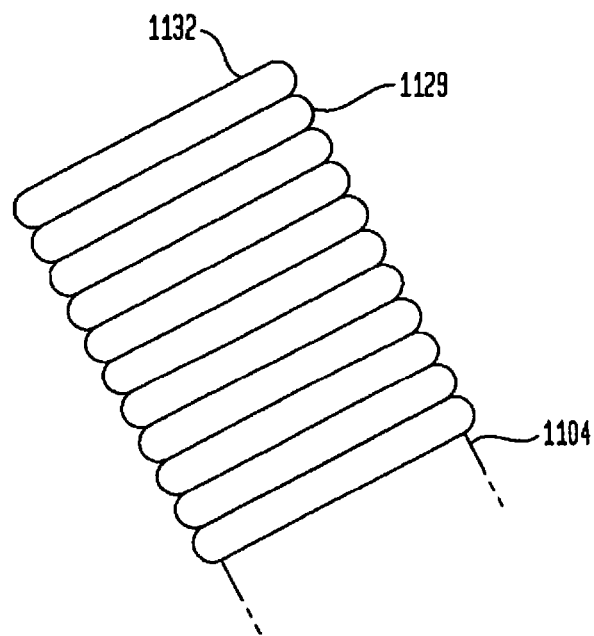
FIG. 11M illustrates a perspective view of a portion of the second interface according to yet another embodiment of the present invention.

Embodiments of the present invention may be configured to aid in the retention of the destination element (not shown) on the distal end 1132 of conduit 1104. In certain embodiments of the present invention, as illustrated in FIGS. 11A and 11B, protrusions 1129 are disposed circumferentially around the exterior surface of conduit 1104. FIG. 11A illustrates conduit 1104 in a simplified profile view, and shows the silhouette of radial protrusions 1129 which are disposed around conduit 1104. FIG. 11B illustrates a plurality of extrusions or projections which are disposed on, or extend from, the exterior of conduit 1104. As shown in FIG. 11M, according to another embodiment of the present invention, a plurality of radial protrusions 1129 on conduit 1104 may be provided along the substantial length of conduit 1104, or at least along a section, for example distal end section 1132. According to another embodiment of the present invention, protrusions 1129 may be disposed on a separate collar and positioned on conduit 1104 prior to implantation of flow connector 1100. As illustrated in FIGS. 11P and 11Q, the retention protrusions 1129 need not be uniform or simple. A matrix protrusion configuration 1129 is illustrated in FIG. 11P, according to another embodiment of the present invention. In a yet further embodiment of the present invention, sinusoidal protrusions 1129 are illustrated in FIG. 11Q.

In other embodiments of the present invention, the retention feature provided on the surface of conduit 1104 may be surface treatments. In an exemplary embodiment of the present invention illustrated in FIG. 11O, the exterior surface of conduit 1104 may be dimpled or dented such that the treated exterior surface provides retention. Depending on the size of the dimpling or denting surface treatment, the exterior surface can be configured to provide a friction fit on the interior surface of the destination element, for example a blood vessel. Other retention features may be provided on the exterior of conduit 1104. For example, in another embodiment of the present invention, a plurality of barbs 1229 or other sharp projections are disposed on the exterior of conduit 1204. Barbs 1229 are configured such that they at least partially pierce the wall of the destination element, for example a blood vessel, in order to retainingly secure the element on conduit 1204. In other embodiments of the present invention, barbs 1229 pierces through the destination element while retainingly securing the destination element on conduit 1204.

Flow connector 100, 200 further comprises a rest surface 136, 236 on conduit 104 adjacent the joint region 106, as illustrated in FIGS. 1D and 2B according to yet further embodiments of the present invention. In the embodiment illustrated in FIG. 1D, rest surface 136 is a recess in the body of conduit 104 configured to receive a wall of the source body space around rest surface 136 once flange 102 is implanted therein. In the embodiment illustrated, rest surface 136 is substantially smooth and free of protrusions 129 described above which are configured to retain the destination element once the destination element is positioned over protrusions 129. In the embodiment illustrated in FIGS. 1D and 2B, rest surface 136 is shaped with a curve, and source body space 227 is shown in FIG. 2B as conforming to the curved shape of rest surface 136. However, the degree to which body space 227 is shown to curve in FIG. 2B is exaggerated for illustrative purposes and may not always take the degree of curvature depicted.

Figure 11N:
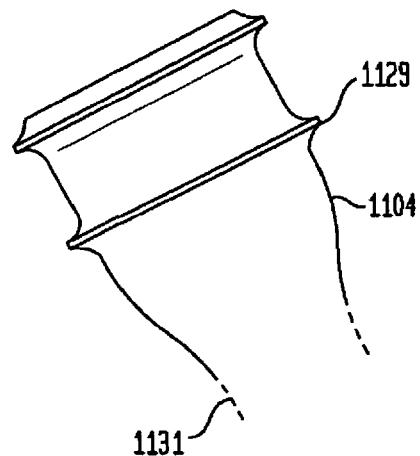
FIG. 11N illustrates a perspective view of a portion of the second interface according to a yet further embodiment of the present invention.
Figure 11O:
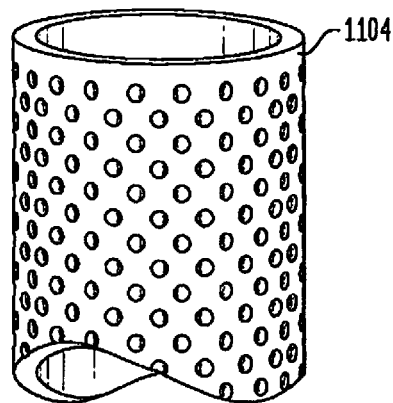
FIG. 11O illustrates a perspective view of a portion of the second interface according to another embodiment of the present invention.
Figure 11P:
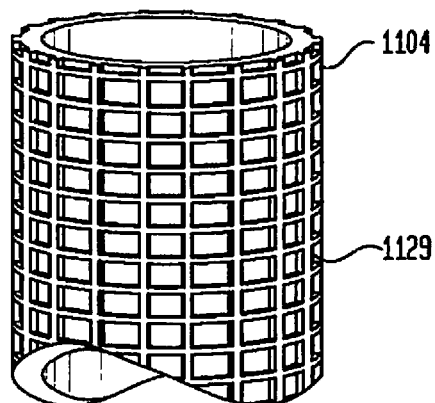
FIG. 11P illustrates a perspective view of a portion of the second interface according to yet another embodiment of the present invention.
Figure 11Q:
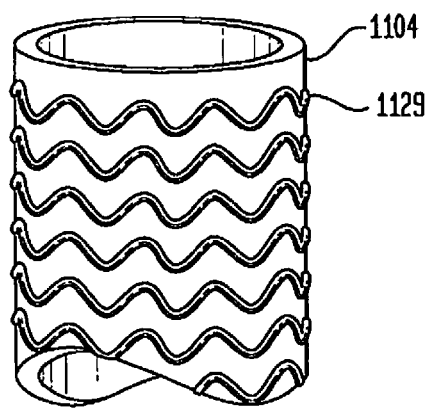
FIG. 11Q illustrates a perspective view of a portion of the second interface according to a further embodiment of the present invention.

In addition to the protrusions described above being used to retain the destination element upon being fit on the protrusions, the protrusions may also be used to receive one or more retaining elements such as sutures or a securing collar, or combinations thereof, as in embodiments illustrated in FIGS. 10E, 11A-11N. FIG. 10E illustrates one embodiment of the present invention in which two sutures are placed on the destination element, in this case a vein, in order to compress the vein towards recesses disposed along the exterior surface of conduit 1004. FIG. 11A illustrates one embodiment in which the plurality of adjacent protrusions 1129 cooperatively form angled recess therebetween into which retaining elements such as sutures 1190, as illustrated in FIGS. 11E, 11F, 11I, 11J, can compress the destination element at least partly into. In the embodiment illustrated in FIG. 11B, the retaining elements can compress the destination element, such as the tissue wall of a vein, in between the spaces between protrusions 1129. In the embodiments of the present invention illustrated in FIGS. 11C, 11D, 11G, 11H, a securing collar 1169 may be used with a portion of the destination element, for example the tissue wall of a vein, disposed between securing collar 1169 and conduit 1104 to secure the destination element on conduit 1104. In certain embodiments of the present invention, the destination element portion may be compressed by securing collar 1169 against the exterior surface of conduit 1104. In other embodiments of the present invention, securing collar 1169 may press the destination element portion into correspondingly shaped recesses along the exterior surface of conduit 1104 such that an interference fit between the recesses and securing collar 1169 will retain the destination element portion on conduit 1104. Although a plurality of protrusions 1129 may be disposed along a length of conduit 1104 according to certain embodiments of the present invention, such that a surgeon may have a wide variety of choices of protrusions 1129 to use in order to secure the destination element on conduit 1104, protrusions 1129 may also be provided at distinct locations in order to simplify conduit 1104, where the surgeon is provided with a reduced number of protrusions 1129, for example two as shown in FIG. 11N according to one embodiment of the present invention. As shown in FIG. 11N, protrusions 1129 may flare out from a smooth exterior surface of conduit 1104 such that a securing element such as sutures 1190, configured with a smaller diameter than protrusions 1129, may be placed nearer the proximal end 1131 of conduit 1104 such that an interference fit is formed between sutures 1190 and protrusions 1129. In such embodiments, in addition to the one or more sutures acting to retain the destination element on conduit 1104, the flare at the distal end of conduit 1104 itself may be sufficient to provide a compression fit to also retain the destination element on conduit 1104. Such a compression fit also acts to provide a seal to prevent leakage flowing through conduit 1104 into the destination element. In alternative embodiments of the invention, flare portions 1129 (referred to previously as protrusions 1129) may be constructed as a separate component from conduit 1104 such that conduit 1104 can rotate 360° about a longitudinal axis of flare portion 1129 while flare portion 1129 remains stationary and secure to the destination element.

It is to be understood that embodiments of the present invention may be used to connect flow connector described herein with an artificial conduit 1999, as illustrated in FIG. 19. As shown, a first flow connector 1900 is configured to be coupled to artificial conduit 1999 and retained by securing collar parts 1269A, B. Securing collar parts 1269A, B combine to form securing collar 1269. Securing collar parts 1269A, B each may be configured with a retention feature such as the recess shown for fitting around a correspondingly configured protrusion on the exterior of conduit. In the embodiment illustrated in FIG. 19, each end of artificial conduit 1999 is positioned between each of the conduits 1904 and retaining collars 1269, wherein each of the flanges 1902 of the flow connectors are implanted without the same or different body spaces, such that the flow connectors 1900 become fluidically coupled. In this manner, flow connectors 1900 may be used in bypass or other procedures which can benefit from one or more flanges which provide fluidic coupling as well as self-sealing and self-supporting features, among others.

Alternate embodiments to aid retention of the first and second body spaces on the flow connector and to hold the flow connector in the body spaces to keep the flow connector from migrating are illustrated in FIGS. 20-55. These retention devices are described herein as used with vessels, e.g. connecting a vein and artery, but can also be used with grafts, other body conduits, etc. as described above. Therefore, although the terms first and second body spaces (or "spaces within the body") are used herein, each body space can encompass a vessel, graft, conduit or other natural or artificially implanted enclosed element as described above. Further, although in the methods and devices described herein the first body space can be an artery and the second body space a vein, this is by way of example only since the first body space can be a vein and the second body space can be an artery, or can be grafts, body conduits, etc, described herein.

In one approach, illustrated in the embodiments of FIGS. 20-31 and 47-51, the securement/retention (or stability) device is placed within the vessel and external of the flow connector so the retention device is positioned between the external wall of the flow connector and the internal wall of the vessel. The flow connector asserts a radial outward force against the retention device which engages the vessel(s) as the outer diameter of the flow connector is slightly greater than the internal diameter of the retention devices. In another approach, illustrated in the embodiments of FIGS. 32-41 and 52-55, the securement/retention (or stability) device is placed outside the vessel (or graft or body conduit) so the vessel is positioned between the internal wall of the securement/retention device and the external wall of the flow connector and the retention device applies a radial inward clamping force against the vessel and flow connector as the inner diameter of the retention device is slightly smaller than the outer diameter of the flow connector and/of vessel. Further, in some embodiments, the retention devices are one piece units which lockingly engage with both the first and second body spaces; in other embodiments the retention devices are two pieces with one piece engaging the first body space and the other piece engaging the second body space and then the two retention devices are connected or interlocked.

The retention devices of FIGS. 20-51 provide a sutureless connection of the first and second body spaces and sutureless connection of the flow connector to the body spaces which facilitates and simplifies the procedures and improves the consistency of the anastomosis since reliance on the suturing technique of the surgeon is avoided. However, a surgeon would not be precluded from applying a suture(s) if desired. The retention device of FIGS. 52-55 enables a sutureless connection to the second body space, e.g., destination element such as a vein, but, has tabs for sutures for securement to the first body space, e.g., a source element such as an artery. Each of these retention devices are described below.

Turning first to FIGS. 20-30, which illustrates one embodiment of an internal retention device, retention device is designated generally by reference numeral 2010. Retention device 2010 has a proximal end 2012 and a distal end 2014, the distal end defined herein in the direction of blood flow—flowing in a distal direction. The device 2010 is preferably composed of a metallic material with sufficient springiness so that it can be compressed (collapsed) to a reduced profile position during delivery and return to its original position once delivered. In some embodiments, the device 2010 can be composed of a shape memory material such as Nitinol. Other materials are also contemplated.

The device 2010 is preferably formed from a tube having cutouts therein forming a series of struts. The cutouts can be formed from laser cutting or other methods. The struts form a pattern to create substantially diamond shaped openings 2016, shown in FIGS. 20 and 22. The strut pattern and diamond shaped openings enable collapse of the device 2010 for delivery. The strut pattern includes a first (distal) set of connected V-shaped struts 2020 and a second (proximal) set of connected V-shaped struts 2022, each set 2020 and 2022 extending around 360 degrees to form a closed ring. The proximal vertices 2025 of the first set of struts 2020 is joined to the distal vertices 2023 of the second set of struts 2022, designated as region 2024. For clarity, not all of the struts and vertices are labeled in the drawings as not all identical parts are labeled.

At the proximal end 2012 of device 2010, the strut pattern includes an elongated longitudinally extending strut 2026, extending from the proximal vertex 2027 of the proximal struts 2022, and each terminating in a hook 2028. Each hook 2028 curves radially outwardly from the longitudinally extending strut 2026 and curves in a 180 degree arc so that the penetrating (sharpened) tip 2036 which engages and penetrates the first body space points toward the distal end 2014 of the device 2010. Other hook configurations and angles are also contemplated to achieve the purpose of engaging and penetrating the wall of the body space for the reasons described below. An example of such alternate configuration is described below and illustrated in FIG. 31. Additionally a fewer number of hooks can be provided. Although six V-shaped struts 2020 and 2022 are shown, it is also contemplated that a fewer or greater number of V-shaped struts could be provided.

At the distal end 2014 of the device 2010 are a series of tines 2030. The tines 2030 extend from the distal vertex 2029 of the distal struts 2020. In the illustrated embodiment, the tines 2030 extend from every other distal vertex 2029 of the distal strut 2020, however, it is also contemplated that a greater number of tines 2030 could be provided, e.g., extending from each vertex 2029, or alternatively a fewer number of tines 2030 could be provided. The tines 2030 extend proximally from the distal vertex 2025, extend radially outwardly, and terminate in sharpened penetrating tips 2032. Other tine configurations and angles are also contemplated to achieve the purpose of engaging and penetrating the wall of the body space for the reasons described below in conjunction with the method of use.

The device 2010, as well as the other retention devices of FIGS. 31-55 described hereinbelow, is preferably formed from a cut tube so the struts are integral, however, in alternate embodiments, the struts are formed by separate elements, e.g., wires, strips, etc., that are bonded or welded together to form the strut pattern of FIG. 20.

In the normal position of the device 2010, the device 2010 by way of example can have an inner diameter of about 2 mm to about 8 mm, and preferably about 4 mm, and an outer diameter of about 2.2 mm to about 9 mm, and preferably about 4.4 mm. The device 2010 can be compressed to an outer diameter of about 1 mm to about 4 mm, and preferably about 2 mm for delivery and then allowed to expand to its original position. Other diameters are also contemplated.

The conduit portion of the flow connector can, by way of example, have an inner diameter of about 1.5 mm to about 7.5 mm, and preferably about 3.5 mm, and an outer diameter of about 2 mm to about 8 mm, and preferably about 4.0 mm.

Figure 31:
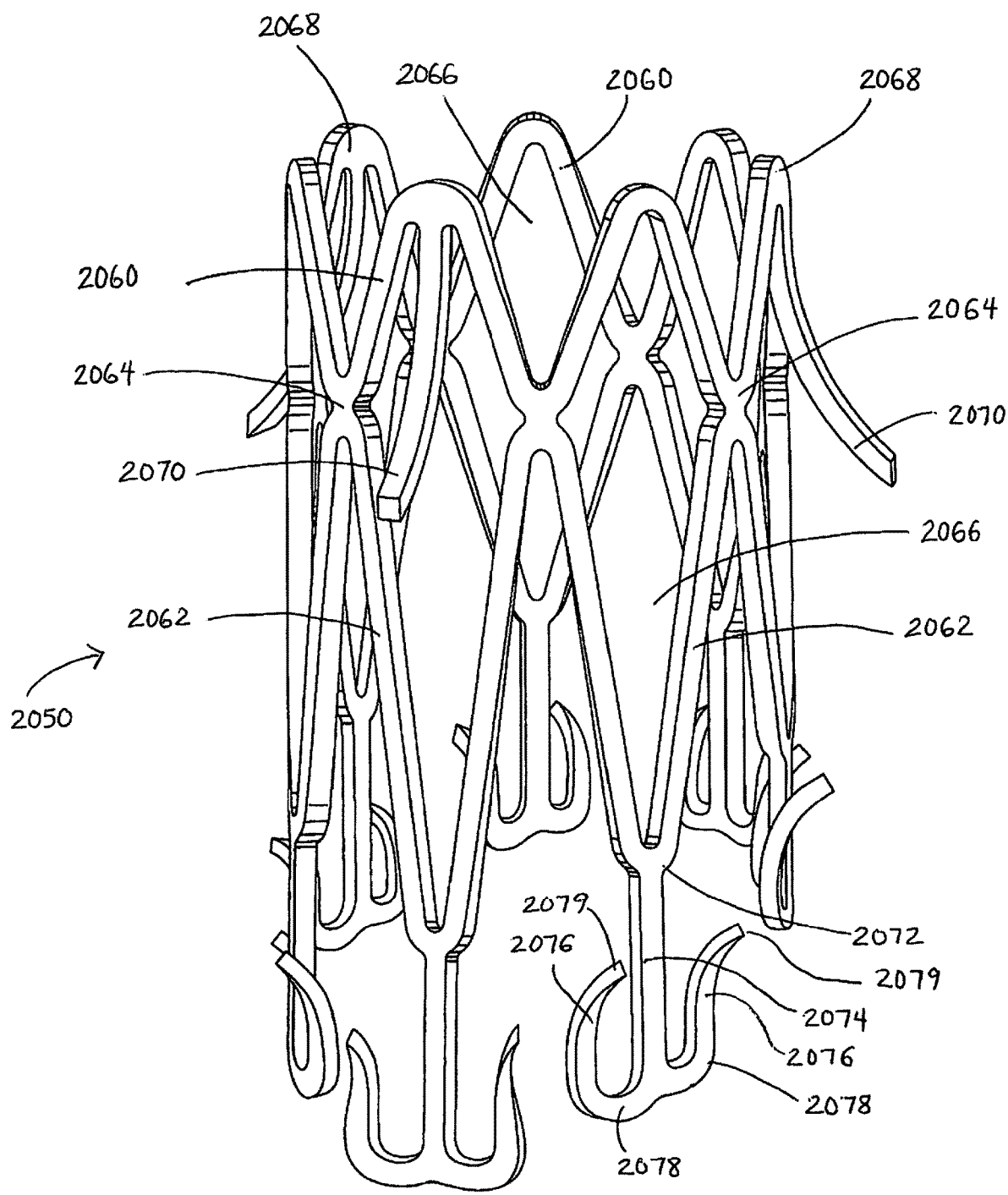
FIG. 31 is a perspective view of an alternate embodiment of the retention device of the present invention.

An alternate embodiment of the hook configuration is illustrated in FIG. 31. The securement/retention device is designated generally by reference numeral 2050 and is identical to device 2010 except for the hook configuration. Therefore, the retention device 2050 has a first (distal) set of V-shaped struts 2060 and a second (proximal) set of V-shaped struts 2062, each set 2060 and 2062 extends around 360 degrees to form a closed ring as in device 2010. The sets 2060 and 2062 are joined at their vertices, designated as region 2064 and form substantially diamond shaped openings 2066. The device 2060 also has a series of tines 2070 identical to tines 2030 of FIG. 20 which extend from distal vertices 2068 of distal struts 2060. Further details of the device 2060, other than the hooks 2070 will not be further described herein, since device 2060 and 2010 differ only in the hook design.

A longitudinally proximally extending strut 2074 extends from the proximal vertices 2072 of the proximal set of struts 2062. The proximal end of the elongated strut 2074 branches outwardly into opposing directions, forming barb shaped hooks 2076, rather than the U-shaped hooks of FIG. 20. More specifically, each branch 2078 extends outwardly from strut 2074 and then curves distally so the hooks 2076 point in a distal direction. The hooks 2076 terminate in penetrating (sharpened) tips 2079. Although a hook 2076 extends from each proximal strut 2062, it is also contemplated that a fewer number of hooks 2076 could be provided.

The method of insertion of the flow connector and retention device of FIG. 20 will now be described with reference to FIGS. 23-29. Note the method is described for attaching a vein to an artery, however, connection of spaces within the body including, grafts, other conduits, etc. are also contemplated. The device of FIG. 31 would be inserted in an identical manner.

First, as shown in FIG. 23, after an opening A is made in the arterial wall B of the artery, the retention device 2010, contained in a compressed (collapsed) position within a cannula C to reduce its profile for insertion, is moved toward the vessel opening A. Note in some embodiments, depending on the internal diameter of the cannula and/or the outward extension of the tines 2030, the tines 2030 are compressed by the cannula wall to a more straightened position. Note also in the compressed position the hooks 2028 maintain their curved configuration. However, it is also contemplated that the hooks in the compressed configuration could be maintained in a more straightened position and return to their curved position when released from the cannula C. Materials such as shape memory Nitinol could be used to achieve this.

The cannula C is placed adjacent, in abutment with or slightly into the opening A and a pusher D is advanced distally to advance the device 2010 through the opening A and into the artery lumen as shown in FIG. 24. In a preferred method, however, the cannula C would be inserted through the opening A and into the lumen of the artery with the retention device 2010 contained inside and then the pusher D advanced to move the retention device 2010 out of the confines of the cannula. In either case, after the proximal portion of the retention device 2010, with the hooks 2028, is positioned within the vessel lumen, the cannula C is removed and the retention device 2010 returns (expands) to its original, non-compressed position as shown in FIG. 25. The retention device 2010 preferably applies a radial force around the opening A of the artery to facilitate insertion of the flow connector delivery sheath.

With the hooks 2028 within the vessel lumen, the flow connector 100A is inserted through the axial opening 2031 in retention device 2020 as shown in FIG. 26. In the illustrated method, the flow connector 100A is inserted through the retention device 2010 before the retention device 2010 is pulled away (retracted) for the hooks 2028 to penetrate the vessel wall B. However, it is also contemplated in an alternate insertion method, that the retention device 2010 is first retracted so the hooks 2028 penetrate the vessel wall B prior to insertion of the flow connector 100A. In this version, cannula C is moved proximally with proximal portions of the retention device 2010 contained therein to move the hooks 2028 distally to penetrate the vessel wall (as in the hook position of FIG. 28) prior to insertion of the flow connector 100A.

Figure 28:
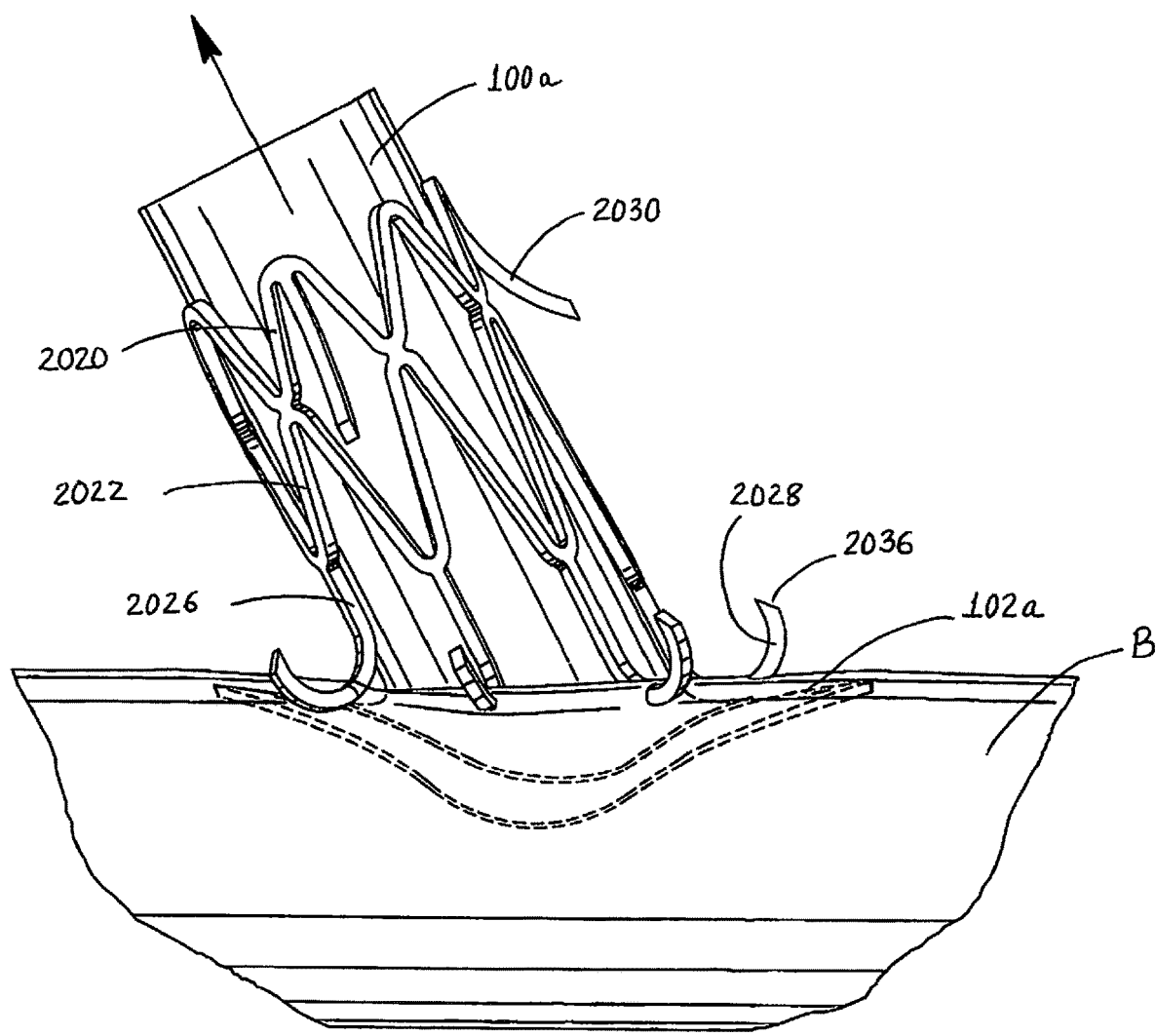
FIG. 28 is a view similar to FIG. 27 showing proximal movement of the flow connector and retention device so the hooks of the retention device penetrate the wall of the artery adjacent the opening in the artery.

Returning to FIG. 26, the flow connector 100A is contained in a folded or collapsed low profile insertion position within a delivery sheath F. Note that the flange 102A of the flow connector 100A is positioned within the vessel lumen, extending distally beyond the hooks 2028 of retention device 2010. The flow connector 100A, when released from the delivery sheath F by advancement of pusher G, expands toward its original diameter such that the outer diameter is slightly greater than the inner diameter of the retention device 2010 to provide a slight radial outward force against the retention device 2010 to provide an interference fit to hold the two together as shown in FIG. 27. In an exemplary embodiment, the outer diameter of the flow connector could be between about 2 mm and about 8 mm, and preferably about 4 mm. With the flow connector 100A and retention device 2010 held together, the unit is pulled away as shown in FIG. 28 so the hooks 2028 engage and penetrate the vessel wall adjacent the vessel opening A. As shown, the hooks 2028 surround the opening and extend 360 degrees around the opening. Note in this position, the elongated struts 2026 are positioned external of the vessel B. As noted above, it an alternate embodiment, the hooks would already be in position prior to insertion of the flow connector 100A.

Figure 29:
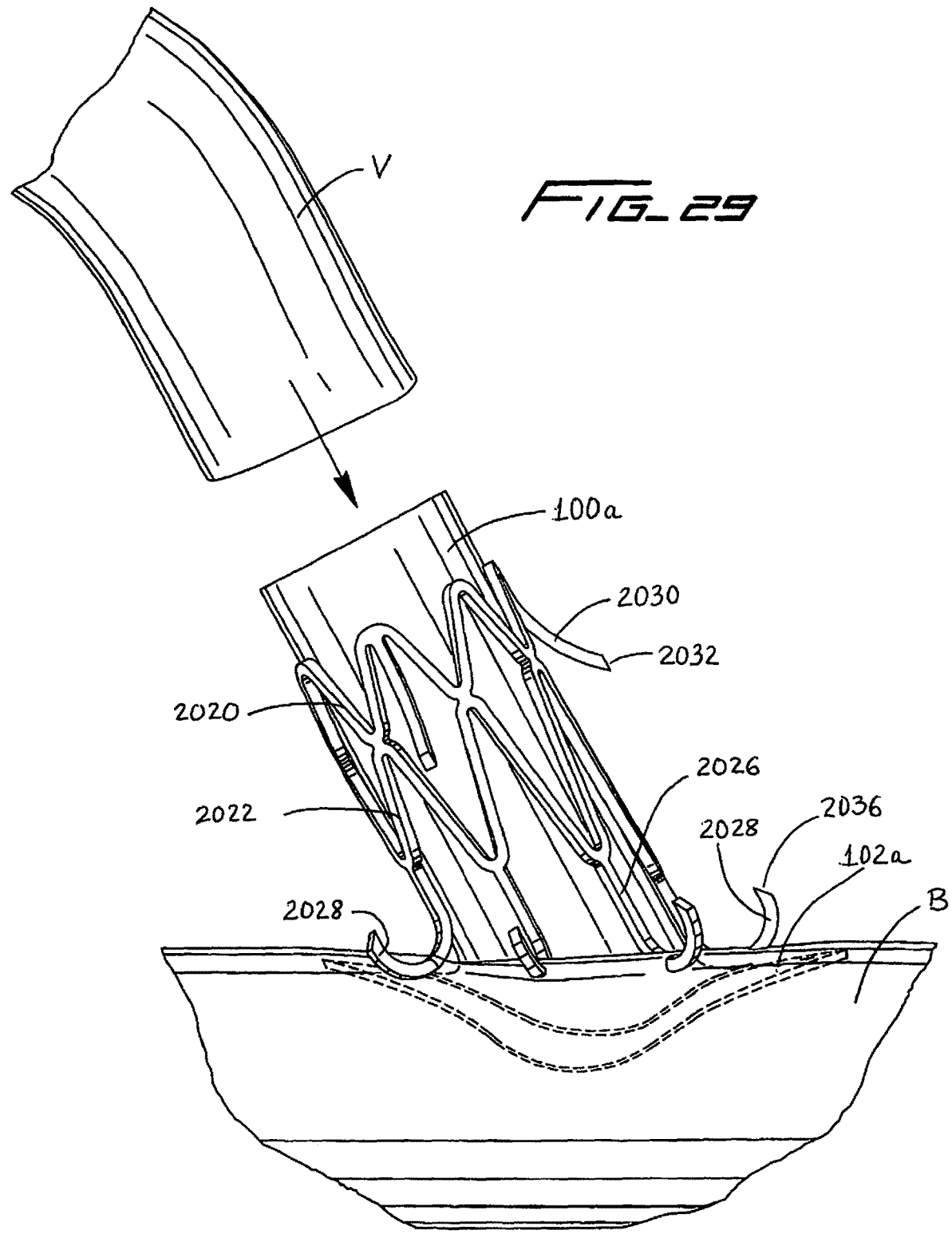
FIG. 29 is a view similar to FIG. 28 showing the second body space, e.g. a vein, prior to placement over the retention device of FIG. 20.
Figure 30:
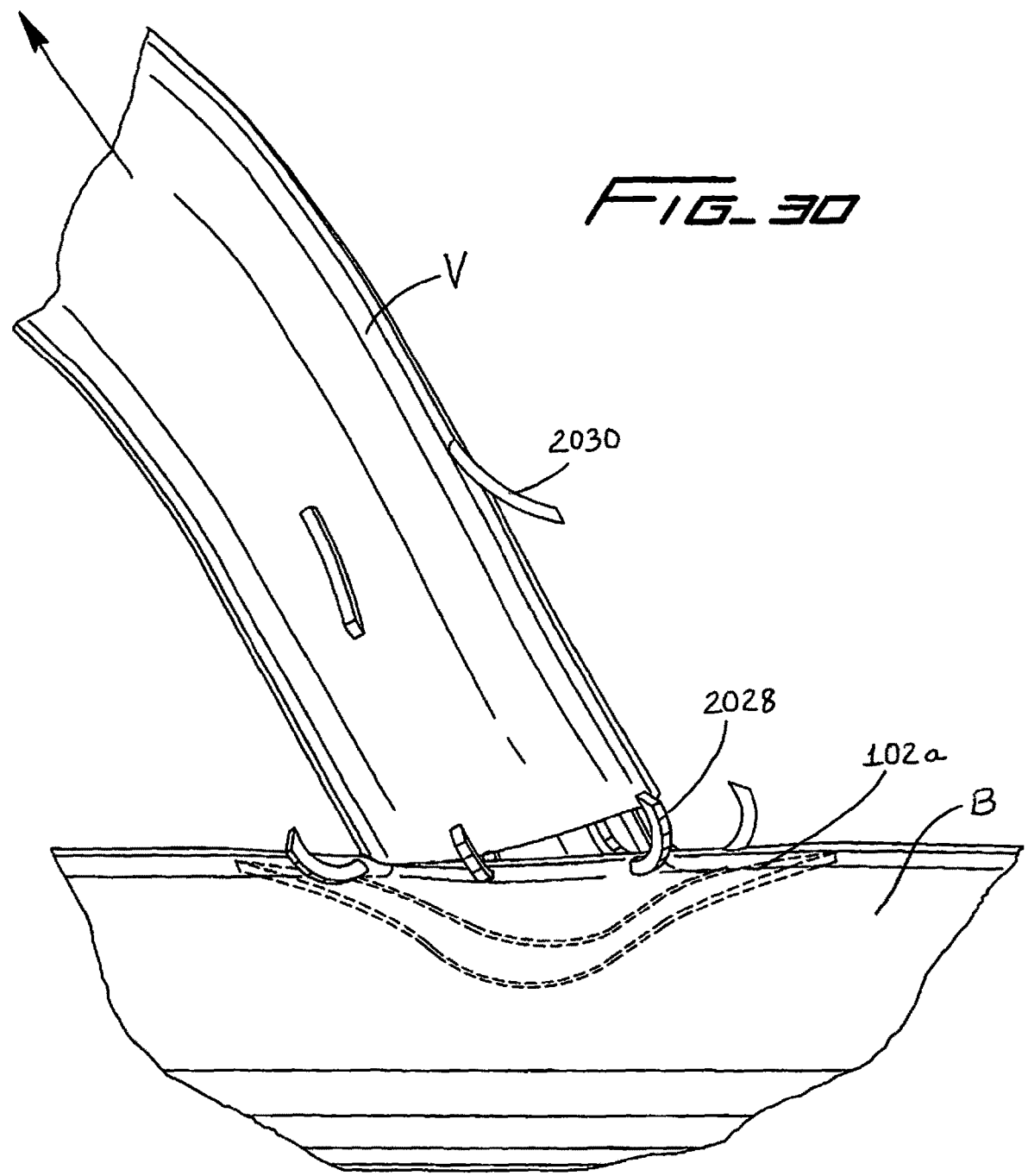
FIG. 30 illustrates the vein of FIG. 29 being placed over the retention device, with the tines of the retention device penetrating through the wall of the vein.

Next the vein V which is intended to be connected to the artery B to provide a fluid connection (communication) is placed over the outer wall of the retention device 2010 as shown in FIGS. 29 and 30. That is, the proximal end of the vein V is placed over the retention device 2010, and pulled (stretched) over the retention device 2010. Note the tines 2030 can be flexed inwardly by the vein V until in the desired position. Once fully positioned over the retention device 2010, the penetrating ends 2032 of the tines 2030 penetrate the wall of the vein V to retain the vein V thereon. Thus, the tines 2030 secure the vein V to the retention device 2010 which is secured to the artery B via hooks 2028. Fluid flow is then allowed between the two vessels, which are now connected to form an end to side anastomosis. Note that the retention device 2020, by holding the vessels B and V in place also helps to maintain the flow connector 100 in place so the flow connector 100 can maintain the fluid tight seal between the flange 100A of the implantable flow connector 100 and the wall of the artery B. This seal is described in detail above with respect to the discussion of the flow connector flange.

Note that the flow connectors 100a illustrated and described herein are substantially identical to the flow connector 100 of FIG. 1A in that it has a conduit 104a and a flange 102a, identical to conduit 104 and flange 102, except since it does not require suture attachment, it need not be provided with protrusions as shown in FIG. 1C.

FIGS. 47-51 illustrate an alternate embodiment of an internal retention/securement device. In this embodiment, instead of a one piece retention device placed internally, two pieces, one attached to the first space within the body, e.g. the artery (source element), and the other attached to the second space within the body, e.g., the vein (destination element), are provided and are connected in situ. It should be appreciated that if other body spaces are being connected, e.g., artificial grafts or other body conduits, one piece would be attached to one body space and the other piece to the other body space to join the two body spaces.

More particularly, the retention device of FIGS. 47-51 is designated generally by reference numeral 4010. Retention device 4010 has a first proximal component or member 4012 for attachment to the first body space, e.g., an artery, and a second distal component or member 4040 for attachment to the second body space, e.g., the vein. Proximal component 4012 has a distal end 4018 and a proximal end 4016. The proximal component 4012 is substantially identical to retention device 2010, except for the tines 4030, and has a strut pattern forming a first (distal) set of joined V-shaped struts 4020, a second (proximal) set of V-shaped struts 4022, substantially diamond shaped openings 4036, regions 4037 where the distal vertex of proximal struts 4022 are joined with the proximal vertex of distal struts 4020, an elongated strut 4026 extending from the proximal vertex 4027 of the proximal struts 4022, and hooks 4028 with penetrating tips 4029 extending from elongated struts 4026. Since these components are identical to those of FIG. 20, further discussion of these components is not necessary since their configuration, structure and function can be understood by reference to the description of the retention device 2010 of FIG. 20. Also note as in the discussion of the other embodiments herein, for clarity, not all identical parts are labeled.

Locking members 4030 extend from alternating distal vertices 4031 of the distal struts 4020 and perform a different function than tines 2030 of retention device 2010. More specifically, locking members 4030, which extend radially outwardly from device 4010, are configured to engage slots formed in the distal component 4040 as described below. Note the locking members 4030 can also be configured of sufficient length and have penetrating tips to engage and penetrate the second body space to provide supplemental retention of the second body space. In this configuration, the locking members would then also function as wall penetrating tines and would be similar to tines 2030 of retention device 2010.

The distal component 4040, like the proximal component 4012, is formed from a cut tube, preferably laser cut, although other cutting methods are contemplated. Distal component 4040 has a distal end 4042 and a proximal end 4044. A series of solid wall portions 4045 connected by a web 4046. The solid wall portions 4045 have substantially triangular regions and substantially rectangular regions. More particularly, the more distal regions are somewhat triangular with sides 4048a, 4048b extending proximally from vertex 4049. After angling outwardly in triangular-like form, the sides 4048a, 4048b each extend proximally in substantially linear sides 4050a 4050b, forming a substantially rectangular region. Elongated axial slots 4060 extend distally from the proximal edges and terminate in radial slot 4062 to receive locking members 4030 of proximal component 4012 as described below. Alternatively, upper (distal) slot 4064 can receive locking members 4030 of component 4012, also described below. Structure can also be provided so that the proximal component 4012 interlocks with structure at vertex 4046 of distal component 4040 or with other regions of distal component 4040.

Note that that the components 4012, 4040 can be moved in the opposite direction, e.g., distal component 4040 moved distally with respect to proximal component 4012, to disengage the locking members 4030 to release the components 4012, 4040 from the interlocked position to allow removal of the flow connector if desired.

A series of interconnecting V-shaped struts 4052, at distal end 4042, have distal vertices 4054 and proximal vertices 4056. Extending proximally and radially outwardly from each of the distal vertices 4054 is a tine 4058 with a penetrating tip 4059, substantially identical to tines 2030 of retention device 2012 and configured to engage and penetrate the wall of the second body space placed thereover.

In use, with reference to FIGS. 49-51, proximal component 4012 is inserted through an opening in the first body space, e.g., artery B, in the same manner as described above with respect to FIGS. 24 and 25, i.e., inserted through a cannula, like cannula C, so the hooks 4028 are positioned in the lumen of the artery B. The cannula C is then withdrawn in the same manner as described above with respect to FIG. 25, and the flow connector 100a is inserted through the axial opening in the proximal component 4012 in the same manner as described above in conjunction with FIG. 26 above, i.e., inserted in a folded or collapsed position through a delivery sheath like delivery sheath F, and then the delivery sheath is withdrawn, leaving the flange 102a of the flow connector 100a positioned in the lumen of the artery B in the same manner as in FIG. 27. This positioning of the flow connector and distal component is shown in FIG. 49.

A second body space, e.g., a vein V, is placed over the distal component 4040 as in FIG. 49, and together placed over the proximal component 4012 as shown in FIG. 50. (Note it is also contemplated that the vein V is placed over component 4040 before component 4012 is placed in the artery). The distal and proximal components 4040 and 4012 interlock, preferably releasably interlock, as the locking members 4030 extend through upper (distal) slots 4064 and are held within the widened slot area 4064a due to the narrowing of the slot (slot area 4064b) above the widened area 4064a. That is, as the two components are moved together, the locking members 4030 are forced through the narrowed slot area 4064b into the widened slot area 4064a (see FIG. 50). It should also be appreciated, that in an alternate embodiment, the locking members 4030 could engage the lower (proximal) slots 4062 and held therein by the proximal wall 4062a and narrowed slot 4060. With the two components 4012 and 4040 interlocked as shown, and with the flow connector 100a applying an outward radial force on the retention device 4010, the device 4010 and flow connector 100a are retracted so that penetrating hooks 4029 of hooks 4028 penetrate the wall of the artery B as shown in FIG. 51. Note that alternatively, the proximal component 4012 and flow connector 100a positioned therein can be retracted first so the hooks penetrate the artery wall, and then the distal component 4040 (with attached vein V) can be interlocked with the proximal component 4012. In either case, the interlocking of the components 4040 and 4012 retains the flow connector 100a and artery B and vein V in position to achieve an end to side anastomosis which fluidly connects the artery B and vein V and maintains the above described fluid tight seal.

FIGS. 42-46 illustrate an alternate embodiment of a retention device. In this embodiment, a one piece retention device is provided, however, the flow connector and retention device are provided as a single unit. That is, instead of the user having to place the flow connector through the retention device in a separate step, the flow connector and retention device are already attached so the user can insert the flow connector and retention device together through the vessel opening. In this embodiment, the retention device is encapsulated in a polymer material of the fluid connector so there is no need for a separate retention device or the need for the additional steps of pre-inserting a retention device or of attaching a retention device.

The device, or implant, of this embodiment is designated generally by reference numeral 5010 and has an integrated flow connector and retention device. Stated another way, the flow connector 100b includes a conduit 104b similar to the conduit 104 of FIG. 1A, a flange 102b similar to the flange 102 of FIG. 1A, and a retention portion 5012 having a strut pattern embedded between the inner and outer walls 107b, 109b of the conduit 104b. The flow connector 100b is similar to the flow connector 100 of FIG. 1A in that it has a conduit 104b and a flange 102b, identical to conduit 104 and flange 102, except as in the other embodiments herein that do not require suture attachment, it need not be provided with protrusions as shown in FIG. 1C. The device 5010 as noted above provides the flow connector 100b formed integrally with the retention device 5012. Such integration can be achieved by various methods such as overmolding, dip forming, etc. Additional details of the flow connector 100b are not discussed herein as they are substantially identical to that of flow connector 100.

The retention portion 5012 has a distal end 5014 and a proximal end 5024. Retention device 5012 is formed from a series of struts forming two rings of substantially diamond shaped openings—substantially diamond shaped openings 5020 being in the distal ring and substantially diamond shaped openings 5022 being in the proximal ring. These openings 5020, 5022 are formed by the strut pattern shown in FIG. 42 which has a first (distal) set of interconnected V-shaped struts 5026, a second (proximal) set of interconnected V-shaped struts 5028 oriented in the same direction as the distal struts 5026 and an intermediate set of interconnecting V-shaped struts 5030 oriented in the opposite direction of the proximal and distal struts 5028, 5026. The proximal vertices 5032 of the distal struts 5026 are joined to the distal vertices 5034 of intermediate struts 5030 and the distal vertices 5036 of proximal struts 5028 are joined to the proximal vertices 5038 of intermediate struts 5030. An elongated strut 5040 extends from the proximal vertex 5042 of the proximal struts 5028, terminating in vessel penetrating hooks 5044 with penetrating tips 5046 similar to hooks 2028 of FIG. 20. A set of tines 5048 with penetrating tips 5049 extend radially outwardly and proximally from the distal vertices 5035 of distal struts 5026. The strut pattern can be formed by cutting, e.g., laser cutting, a tube. Note for clarity, not all identical parts are labeled in the drawings.

Figure 45:
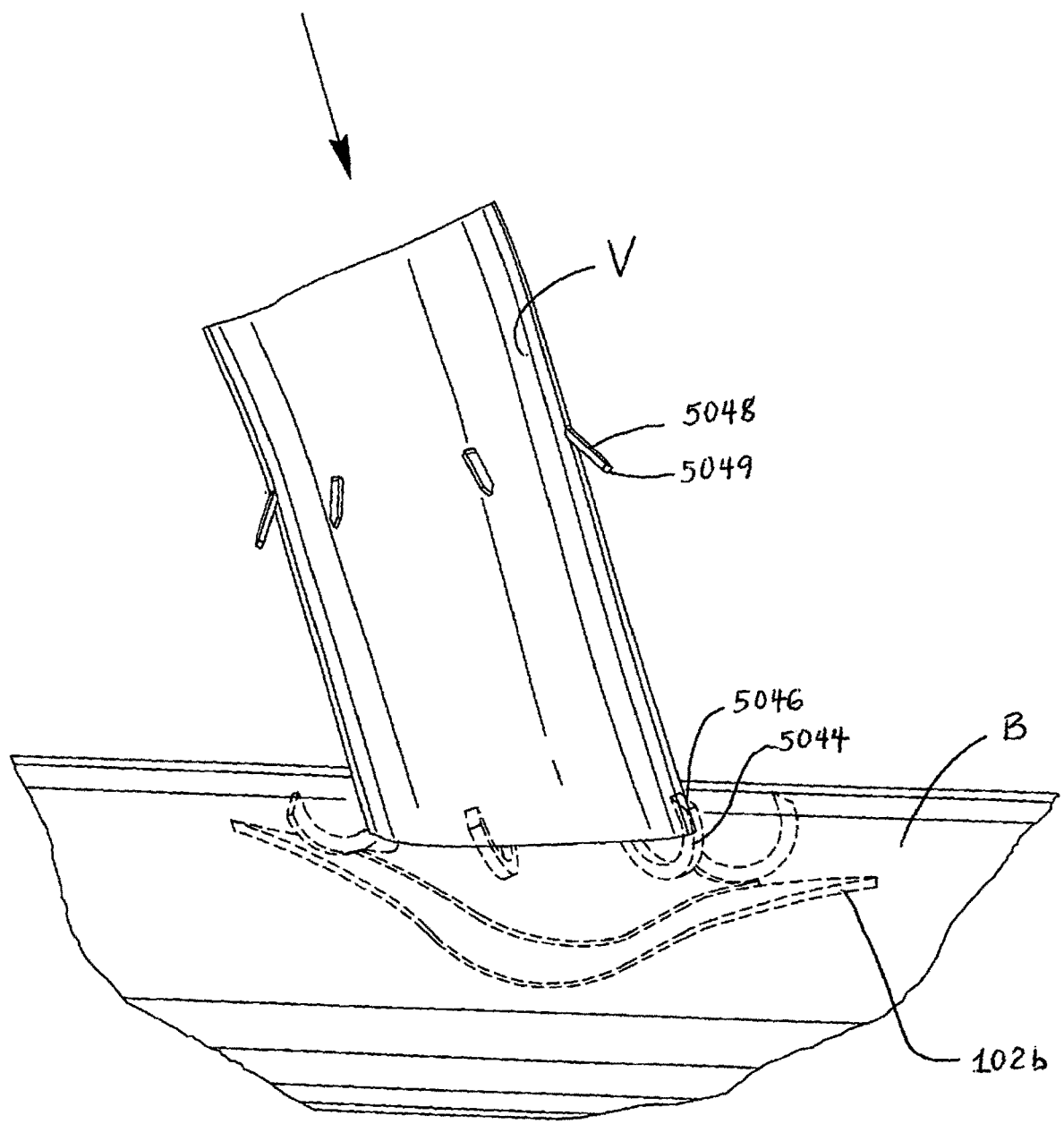
FIG. 45 illustrates the distal portion of the retention device of FIG. 42 placed within a first body space, e.g., an artery, and further showing a vein placed over the retention device with the tines of the retention device penetrating the wall of the vein.
Figure 46:
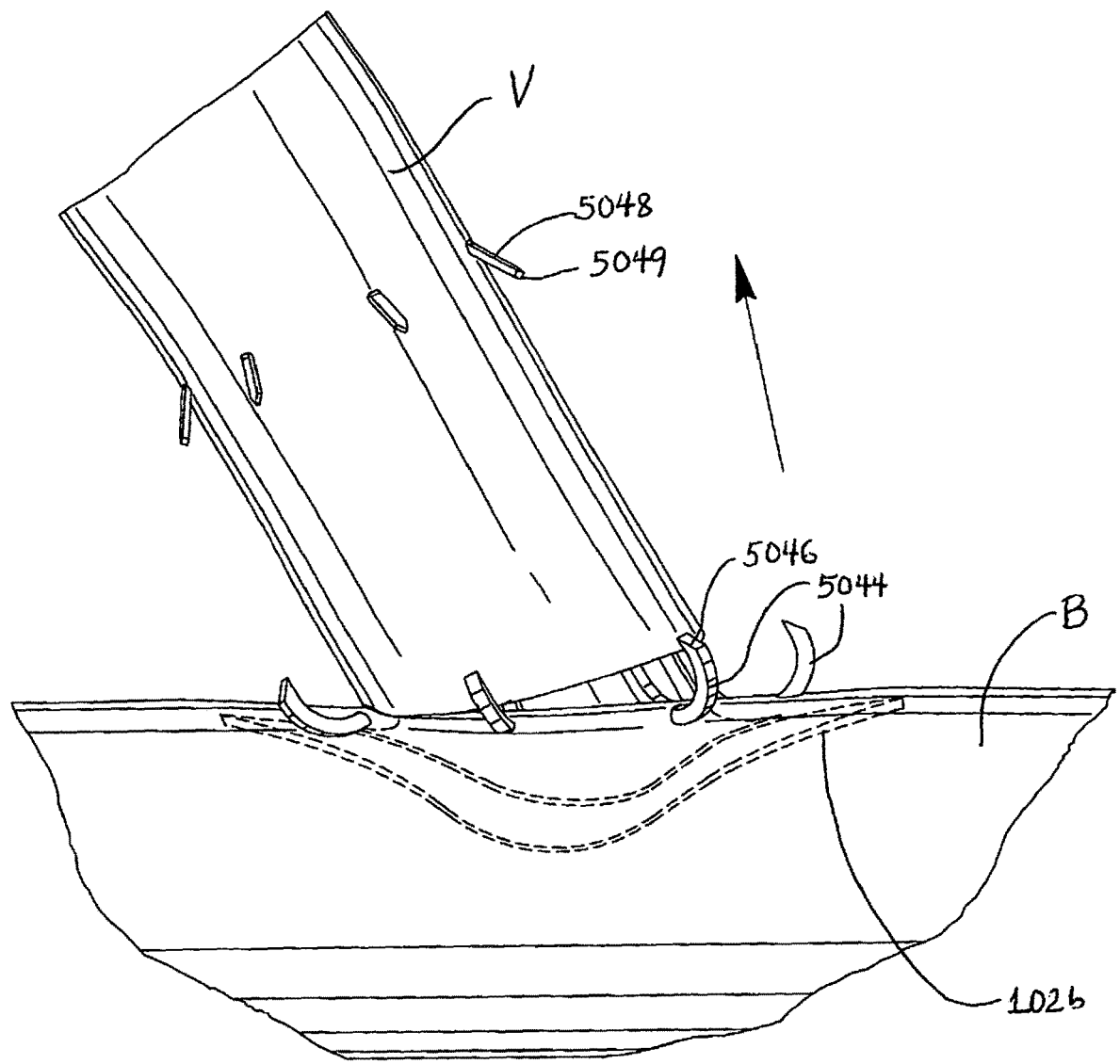
FIG. 46 is a view similar to FIG. 45 illustrating the retention device of FIG. 42 pulled proximally so the hooks of the retention device penetrate the wall of the artery around the opening.
Figure 47:
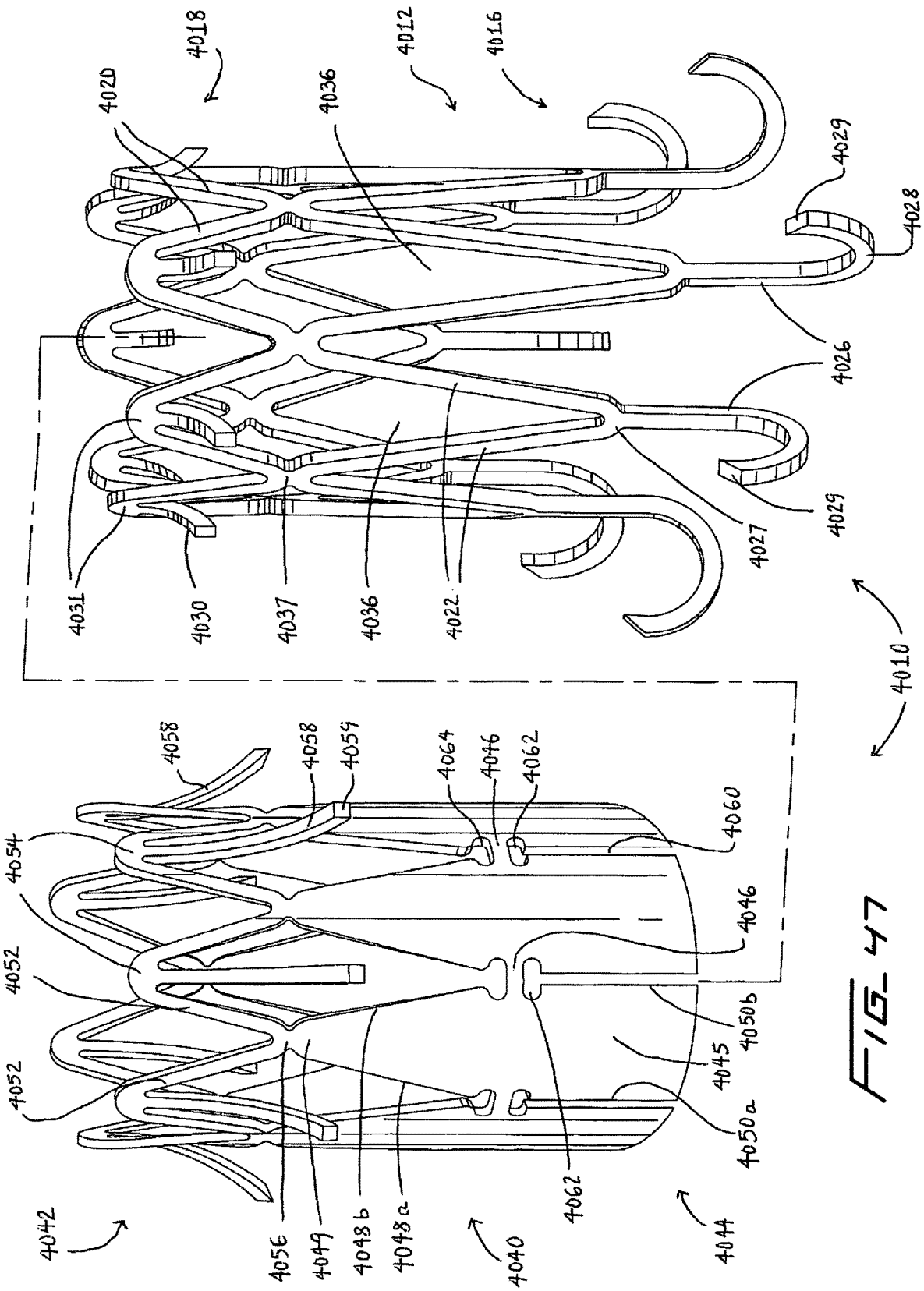
FIG. 47 is a perspective view of an alternate embodiment of the retention device of the present invention illustrating the proximal and distal connectors separated.
Figure 48:
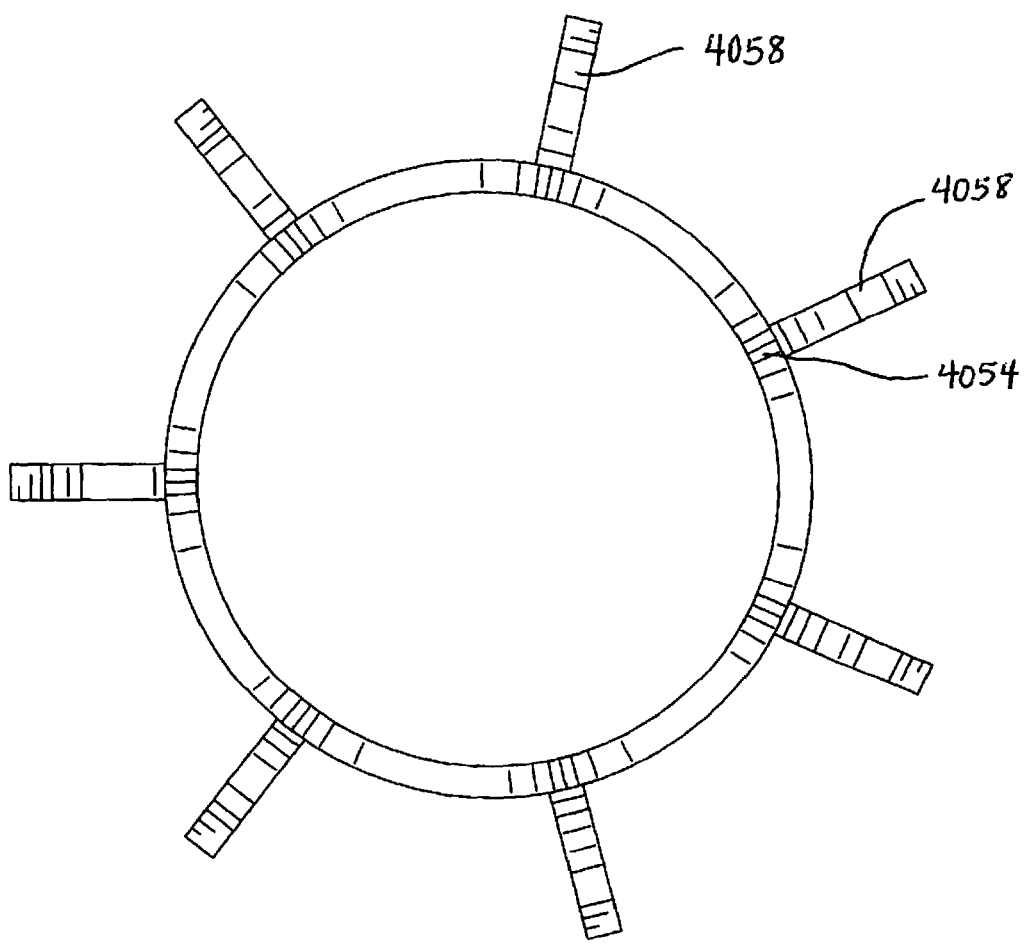
FIG. 48 is a top view of the distal connector of FIG. 47.

In use, the device (implant) or implantable flow connector 5010 is inserted into the first space within the body, e.g., artery B, through a delivery sheath, such as delivery sheath F of FIG. 26. When delivery sheath F is withdrawn as in the manner described above with respect to the embodiment of FIGS. 20-31, the device 5010 moves from its reduced profile insertion position to its original position. With the flange 102b positioned in the lumen of the artery B, a second body space, e.g., vein V, is positioned over the device as shown in FIG. 45, with the tines 5048 penetrating the wall of the vein V when the vein V is in position. The device 5010 is then pulled proximally as shown in FIG. 46, with the hooks 5044 penetrating the wall of the artery B around the opening, e.g., circumferentially around the opening as in the other embodiments described herein, thereby securing together and fluidly coupling the vein V and artery B forming a seal tight end to side anastomosis as with the other embodiments described below. Note that the method also contemplates that the device 5010 is first retracted so the hooks 5044 penetrate the artery wall B, and then the vein V is placed over the device 5010.

Figure 32:
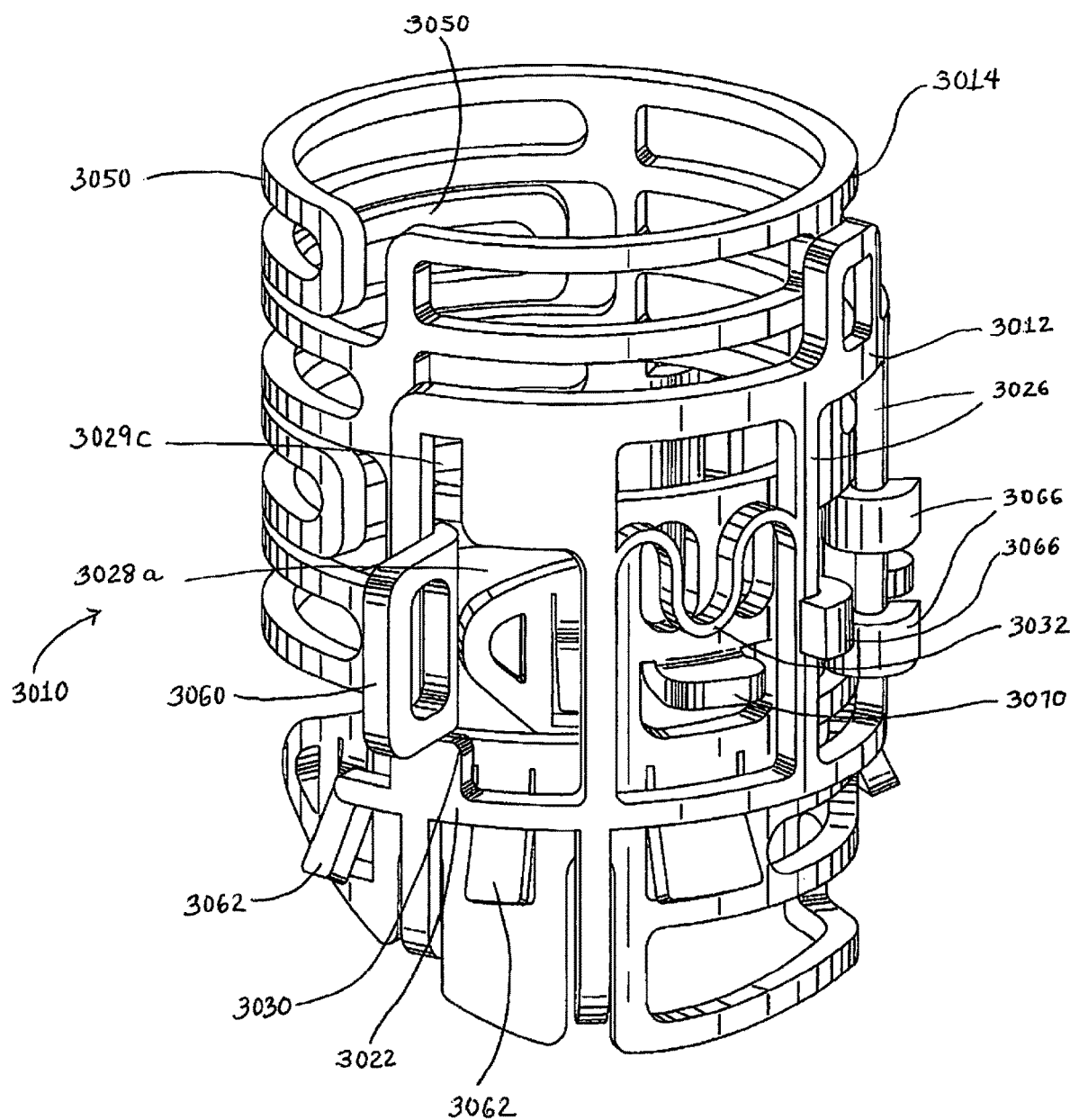
FIG. 32 is a perspective view of another alternate embodiment of the retention device of the present invention showing both the inner and outer member.
Figure 33:
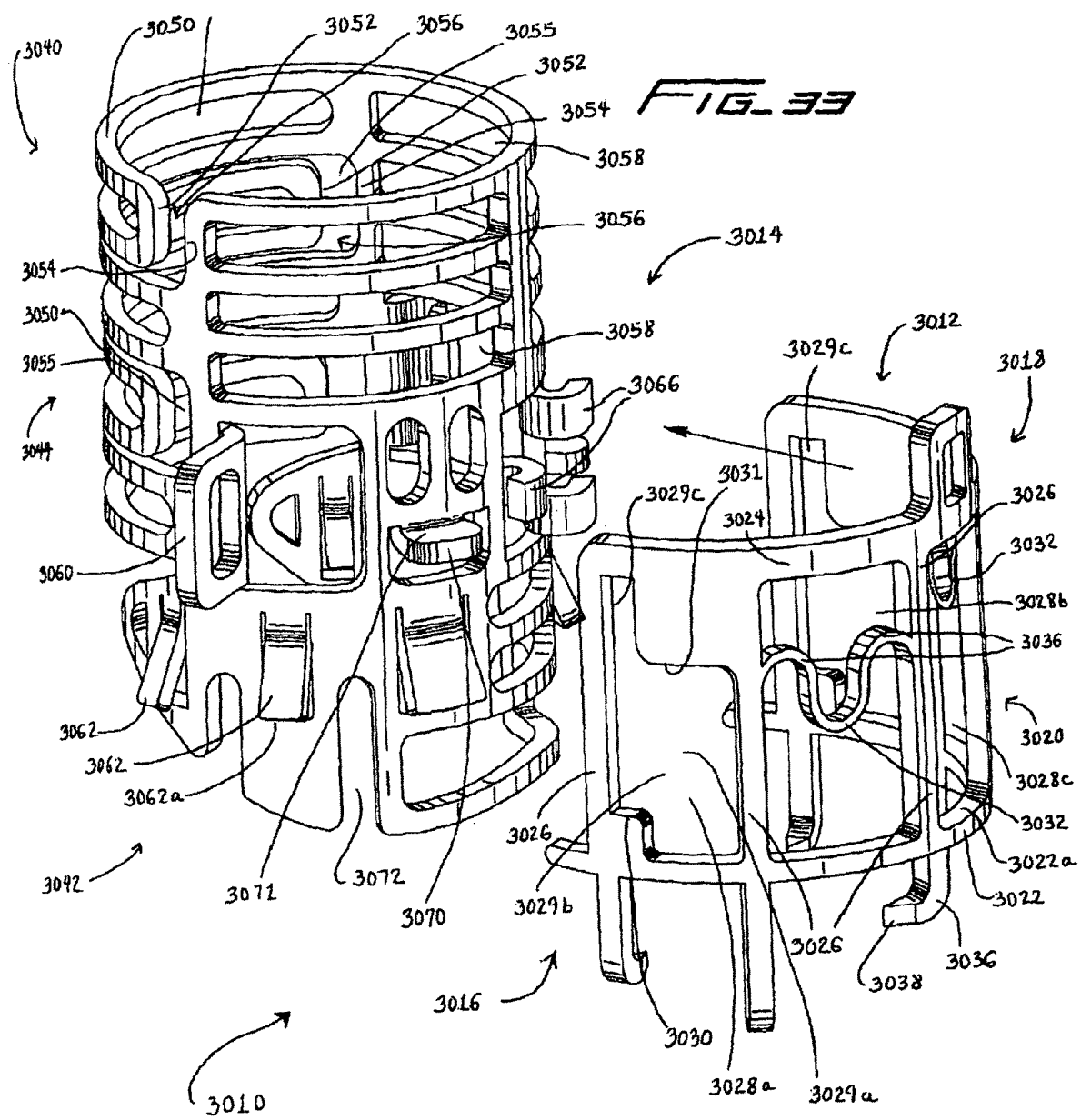
FIG. 33 is a perspective view of the retention device of FIG. 32 with the outer member shown separated from the inner member.
Figure 34:
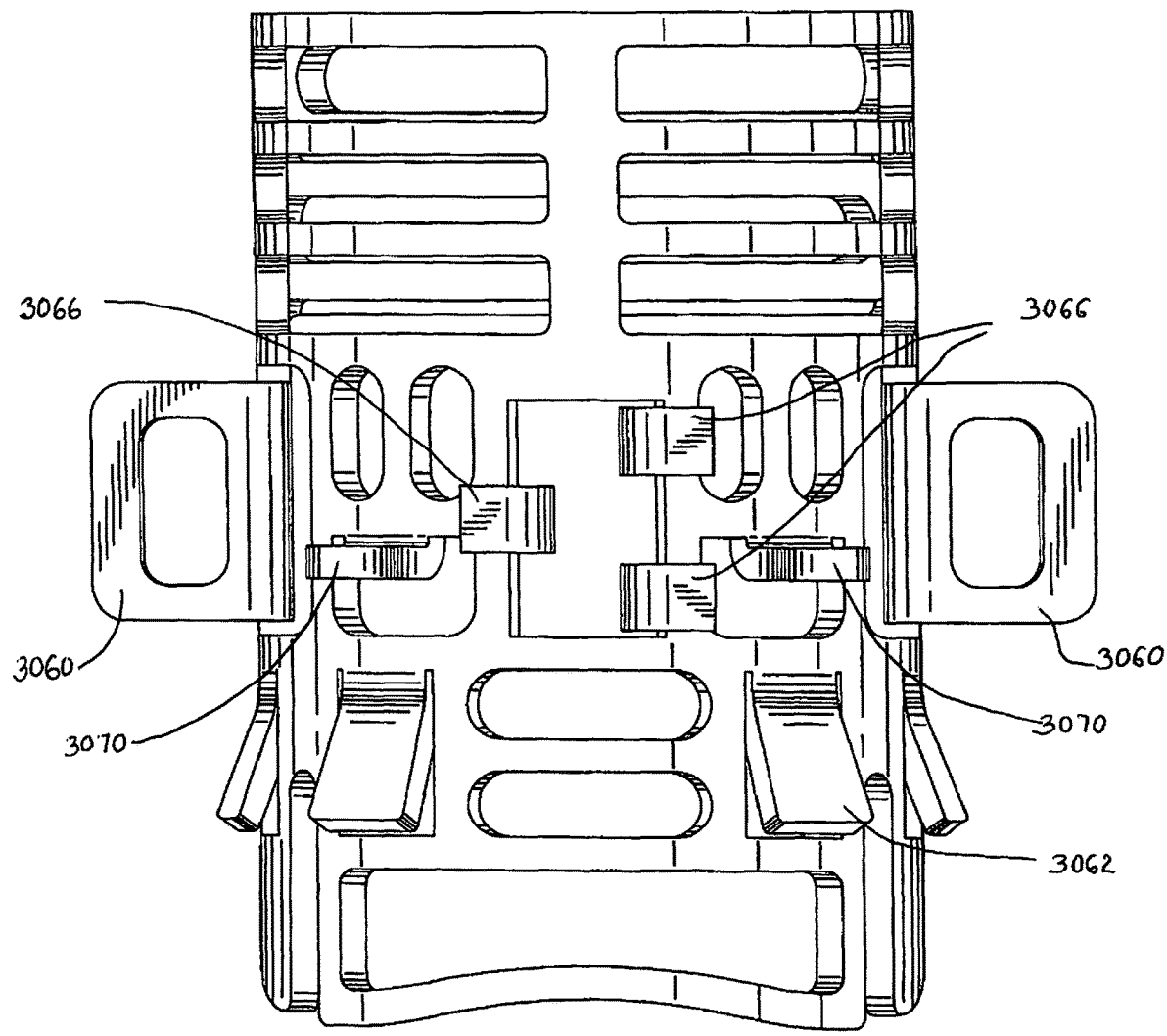
FIG. 34 is a front view of the inner member of the retention device of FIG. 32.
Figure 35:
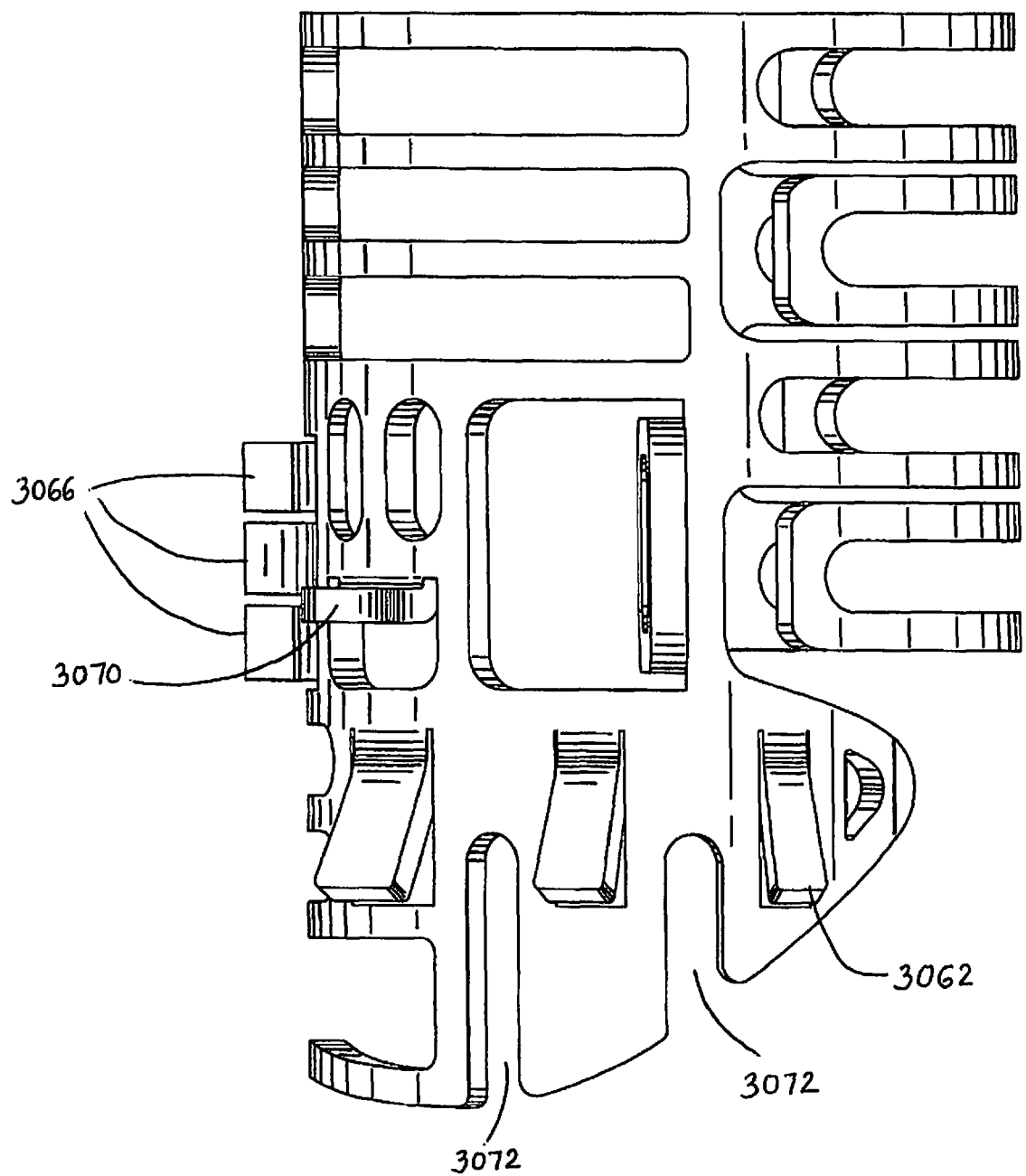
FIG. 35 is a side view of the inner member of the retention device of FIG. 32.
Figure 44:
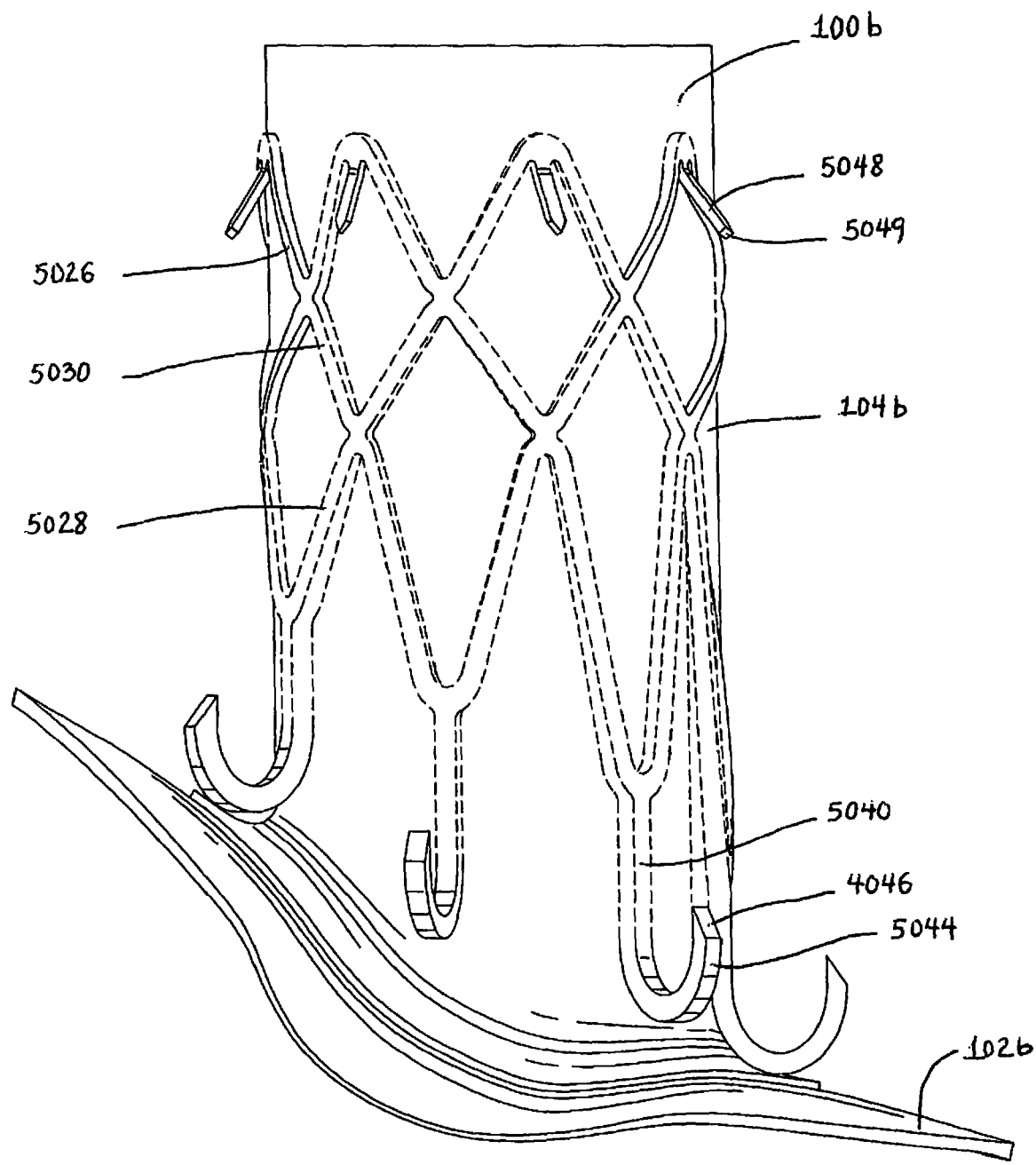
FIG. 44 is front view of the retention device of FIG. 42.

Turning now to the embodiments wherein the securement/retention devices are placed external of the body space rather than internal of the body space as in the embodiments described above, reference is initially made to the embodiment of FIGS. 32-41. With reference to FIGS. 32 and 33, retention device 3010 includes a first outer body member or component 3012 and a second inner body member or component 3014 which are connectable or lockable together as described below. In use, the retention device 3010 is placed on the outer surface of the second body space, e.g., vein, rather than internal of the vein as in the embodiments of FIGS. 20-31. The inner body member 3014 receives within its axial opening the second body space which is positioned over the flow connector, and the outer body member 3012 engages the first body space, e.g., the artery, and is slidable along the outer surface of the inner body member 3012 to lockingly engage the inner body member 3012, thereby securing the flow connector and retaining the first and second body spaces, e.g., the artery and vein, so the flow connector can sealingly fluidly couple the body spaces. The inner and outer members 3012, 3014 can be packaged pre-assembled or alternatively assembled by the user.

With reference to FIGS. 32-36, outer body member 3012 has a proximal portion 3016, a distal portion 3018 and an intermediate portion 3020. The outer body member 3012 is substantially C-shaped, extending in an arc of about 180 degrees (although arcs of other degrees are contemplated) and slides along the outer surface of the inner body member 3014. Outer body member 3012 is preferably formed from a tube, cut to form the illustrated strut pattern, such as by laser cutting or other methods. The strut pattern includes first and second (proximal and distal) radial struts 3022, 3024, separated by axial struts or walls 3026, forming five closed geometric shapes or windows—two outer windows 3028a, two inner windows 3028b and an intermediate window 3028c between the two inner windows 3028b. Outer windows 3028a include inner region 3029a and outer region 3029b, with outer region 3029b raised with respect to inner region 3029a to form a ledge 3030. Outer region 3029b extends distal of wall 3031 of inner region 3029a to form an elongated slot region 3029c. The configuration of the windows 3028a-c provides for sliding movement of the outer component 3012 with respect to the inner component 3014 in the manner described below. Note the edges of the windows 3028a-3028c are substantially linear. However, alternatively, one or more of the edges could be radiused.

Each of the two inner windows 3028b has a compression member, illustratively in the form of a U-shaped spring 3032, positioned therein, with the base of the U extending proximally and the arms 3036 of the U curving in a somewhat S-shape into the axial struts 3026. The springs 3032 deflect when the inner and outer components 3014. 3012 are interlocked in the manner described below.

Proximal radial struts 3022 have a distal wall 3022a which is configured to engage a portion of the inner body 3014 to limit relative movement of the components as described below.

The axial struts 3026 extend proximally beyond the proximal radial strut 3022 and terminate in a hook or spike 3036, extending radially inwardly to engage the first body space, e.g., the artery, as described below. The hook 3036 terminates in a penetrating (sharpened) tip 3038 configured to penetrate the artery wall from the outside in (in contrast to the hooks 2028 of FIG. 20 which penetrate the artery from the inside out). Although each axial strut 3026 is shown terminating in a hook 3036, it is also contemplated that alternatively a fewer number of hooks could be provided such that not all axial struts terminate in hooks.

Turning now to the inner body member 3014, this component has a distal portion 3040, a proximal portion 3042 and an intermediate portion 3044. Inner body member 3014 is preferably formed from a tube, cut to form the illustrated strut pattern, such as by laser cutting or other methods. The strut pattern forms a series axially stacked interleaved radially extending fingers 3050. These interleaved fingers 3050 are positioned in radial openings 3055 formed in inner member 3014 and are positioned in an axial row. Note that the fingers 350 extend in alternating opposite directions so that the first (distalmost) and third fingers extend radially in a first direction and the second and fourth (proximalmost) fingers extend in an opposite second direction. Each of the fingers 3050 terminates in end region 3052 which as shown is spaced from the wall 3054 to form a gap 3056. Each of the fingers 3050 has a series of elongated axially extending openings 3058 formed therein to reduce the mass of the inner body member 3014 and increase flexibility. Note that for clarity, not all identical features of the components have been labeled in the drawings.

The intermediate portion 3044 includes a pair of tool engagement tabs 3060, located on opposite ends of the inner member 3014, preferably spaced about 180 degrees apart. The engagement tabs 3060 extend radially outwardly from the inner body member 3014 and are configured to be engaged by a tool to move the inner body member 3014 from its normal position as shown in FIG. 37 to an open (spread) position shown in FIG. 39, thereby opening the inner body member 3014 into a substantially C-shape configuration to provide an opening to receive therein a second body space, e.g., a vein, and attached flow connector as described below in the discussion of the method of use. Note when the inner body member 3014 is moved out of its 360 degree substantially cylindrical configuration, expanded to the position of FIG. 39, fingers 3050 move away from walls 3054 (see also FIG. 38), and out of the radial opening 3055 to open the inner body member 3014. Note the inner body member 3014 is made of material that enables it to return to its normal substantially cylindrical position after it is opened so it can clamp around the circumference of the second body space. One material that can be used is shape memory material, although other materials are also contemplated.

A series of ramps 3062 are positioned in the proximal portion 3042 of inner body member 3014. The ramps 3062 extend radially outwardly from the inner body member 3014 and are spaced apart about the proximal portion. The ramps 3062 include a lower (proximal) edge 3062a to engage the distal wall 3022a of proximal radial strut 3022. Note the proximal portion 3042 of inner body member 3014 preferably does not extend about the full 360 degrees as does the intermediate and distal portions 3044 and 3040. This enables it to better accommodate the connection between the first and second body spaces since the second body space (and flow connector) is preferably connected at an angle to the first body space (see e.g., FIGS. 40 and 41). Inner body member 3014 further includes a series of reliefs 3072 formed in the proximal portion 3042. These reliefs 3072 shield the hooks 3036 of the outer body member 3012 during delivery and deployment. Bent guide hooks 3066 of inner body member 3014 extend from the intermediate portion 3044 and engage axial struts 3026 of outer body member 3012 to provide guides for the outer body member 3012 as it slides along the inner body member 3014. A pair of locking tabs 3070, with a substantially planar upper surface 3071, extend radially from the intermediate portion 4044 of the inner body member 3014 and engage the proximal surface of the spring 3032 of outer body member 3012 to lockingly engage the inner and outer body members 3014 and 3012 in the manner described below.

As shown in FIG. 32, in the initial position of the outer body member 3012 with respect to the inner body member 3014, the proximal radial strut 3022 is blocked from proximal movement by the radially extending ramps 3060. Also note in this position, the engagement tabs 3060 are in abutment with the ledges 3030 of outer windows 3028a and radially extending locking tabs 3070 of inner body member 3014 are positioned proximally of and out of contact with the U-shaped springs 3032. Note also in this position, the hooks 3066 of outer body member 3012 are shielded within the reliefs 3072 of inner body member 3014. Two of the axial struts 3026 are received in the opening formed in bent guide hooks 3066 so that the hooks 3066 serve as guides for the struts 3026 to help maintain alignment of the outer body member 3012 and facilitate its sliding movement with respect to the inner body member 3014.

A series of other cutouts in the body of inner body member 3014 reduce the overall mass of the component and increase its flexibility.

Turning now to the method of insertion utilizing the retention device 3010 and with reference to FIGS. 40 and 41, the flow connector 100a is inserted through an opening in the first body space, e.g., an artery, through a cannula (not shown). The cannula is similar to the cannula C described above in FIG. 26 and retains the flow connector 100a in the collapsed or reduced profile position. Note the insertion of the flow connector 100a differs from that of FIG. 26 since in this embodiment it is being placed in the artery as in FIGS. 3-5, and does not pass through a retention device as in FIG. 26. Once placed in the artery and positioned so that flange 102a engages the internal wall of the artery B, the second body space, e.g., the vein V, is placed over the conduit portion of the flow connector 100a. Note that it is also contemplated that alternately the vein V is first placed over the flow connector 100a and then the flow connector is inserted into the artery B.

Once the flow connector 100a and vein V are positioned as shown in FIG. 40, retention device 3010 is moved to its open C-shaped position (see FIG. 39) by a tool applying a force to engagement tabs 3060 and then placed about the outer wall of the vein V. The force on the tabs 3060 are then released, allowing the retention device 3010 to return to its normal closed position to clamp about the vein V. (Preferably the inner diameter of the retention device 3010 is slightly smaller than the outer diameter of the vein to provide an interference fit). Consequently, the vein V is positioned between an internal wall of the inner member 3014 and an external wall of the flow connector. (In contrast to the inner retention devices of FIGS. 20 and 47 which are positioned so that the devices are between the external wall of the flow connector and the internal wall of the vein).

Once the retention device 3010 is positioned about the vein V to surround the circumference in a 360 degree arc, the outer body member 3012 is slid distally with respect to the inner member 3014 to lockingly engage the inner body member 3014 to prevent further movement. More specifically, as a force is applied to the outer body member 3012 to slide it proximally, proximal radial strut 3022 is forced over the inclined surface of ramps 3062, forcing the ramps 3062 radially inwardly, and the axial struts 3076 are maintained in axial alignment by the guide hooks 3066 of inner member 3014. The outer member 3012 is advanced sufficiently to advance radial strut 3022 past the ramps 3062. Once passed the ramps, the ramps 3062 return to their initial position and the distal wall 3022a of radial strut 3022 engages the proximal surface 3062a of ramp 3062. By this engagement, in this position, distal movement of the outer body member 3012 is prevented. Also, in this position, the U-shape spring 3032 of outer member 3012 and the tabs 3070 of inner member 3014 are engaged, with the tabs 3070 deflecting he springs 3032, and the springs applying a force to return to their original shape. With this spring/tab and rail/ramp interaction, the outer and inner members 3014, 3012 are lockingly, and preferably releasingly lockingly, engaged. Note further that the hooks 3036 of the outer body member 3012 engage and penetrate the wall of the artery, extending through the artery wall from the outside into the inside. Consequently, with the inner and outer components 3014, 3012 lockingly engaged, the hooks of the outer component 2012 engaging the arterial wall, and the inner member 3014 clampingly engaging the vein V which is fit over the flow connector, the vein and artery are fluidly and sealingly connected forming a secure end to side anastomosis.

Note that the components 3014, 3012 can be moved in the opposite direction, e.g., the ramps 3062 pressed inwardly and the outer body member 3012 slid proximally to disengage from the interlocked position to allow removal of the flow connector if desired.

FIGS. 52-55 illustrate an alternate embodiment of an external retention device. This device differs from the retention devices of FIG. 20-51 in that it is configured to receive a suture wherein the embodiments of of FIGS. 20-51 as noted above, can provide a sutureless system if desired. The external securement/retention device of FIG. 52 is designated generally by reference numeral 6010 and has a distal portion 6012, a proximal portion 6014 and an intermediate portion 6016. Retention device 6016 is somewhat similar to the inner body member 3014 of retention device 3010 of FIG. 32 in that it has a series of radially extending interleaved fingers 6020, except it differs from retention device 3010 in various respects. Retention device 6010 does not receive an outer member which is positioned in the first body space. Instead, retention device 6010 has at its proximal portion 6014 a plurality of radially extending tabs 6018 with a proximal undersurface configured to abut the external wall of the first body space, e.g., the artery. As shown, the tabs 6018 lie in a plane angled with respect to a longitudinal axis of the device 6010 to better conform to the outer wall of the first body space since the flow connector (and second body space e preferably positioned at an angle to the first body space as shown in FIG. 55.

As in the embodiment of FIG. 32, device 6010 is preferably formed from a tube, cut to form the illustrated strut pattern, such as by laser cutting or other methods. The strut pattern forms a series axially stacked interleaved radially extending fingers 6020. These interleaved fingers 6020 are positioned in radial openings 6024 and are positioned in an axial row. The fingers 6020 extend in alternating opposite directions so that the first (distalalmost) and third fingers extend radially in a first direction and the second and fourth (proximalmost) finger extend in an opposite second direction. Each of the fingers 6020 terminates in end region 6022 which as shown is spaced from the wall 6025 to form a gap 6026. Each of the fingers 6020 has a series of elongated axially extending openings 6028 formed therein to reduce the mass thereof and increase flexibility. Note that for clarity, not all identical features of the device 6010 have been labeled.

A series of tabs 6030 which have tips 6032 extending radially inwardly are configured to mate with an anastomotic connector 100c similar to the flow connector of FIG. 1D in that it has barbs or protrusions extending from the conduit portion. The tabs 6030 preferably engage the overlapping wall of the protrusions. As shown, the tabs 6030 are positioned such that within openings 6031 and 6032 two tabs 6030 extend toward each other. A similar arrangement of tabs 6030 is provided spaced about 90 degrees apart (see FIG. 53).

A pair of tool engagement tabs 6034, located on opposite ends of retention device 6010, are preferably spaced about 180 degrees apart. The engagement tabs 6034 extend radially outwardly and are configured to be engaged by a tool to move the device 6010 from its normal position as shown in FIG. 52 to a spread position shown in FIG. 54 (in the same manner as described above with respect to FIG. 39), thereby opening the device 6010 into a substantially C-shape configuration to provide an opening to receive a second body space, e.g., a vein, and attached flow connector, as described below in the discussion of the method of use. Note when the body is moved out of its 360 degree substantially cylindrical configuration, expanded to the position of FIG. 54, fingers 6020 move away from walls 6025, and out of the openings 6024 to open the body member. Note the device 6010 is made of material that enables it to return to its normal substantially cylindrical position after it is opened so it clamps around the circumference of the second body space as its internal diameter is preferably slightly less than the outer diameter of the second body space. A shape memory material such as Nitinol can be used to achieve this, although other materials are also contemplated.

In use, the flow connector, e.g., flow connector 100c, similar to the flow connector of FIG. 1D, is inserted into the first body space, e.g. artery B, with the flange 102c positioned in the body lumen in the same manner as in FIG. 40. After placement of flow connector 100c, the second body space, e.g. the vein, is placed over the flow connector 100c. (Alternatively, the vein could be placed over the flow connector before inserted into the artery). Next, tabs 6032 of device 6010 are pressed by a tool (not shown) to open the device 6010 from its substantially closed (substantially cylindrical) configuration to its open position so that the flow connector 100c and vein can be placed into the device 6010. After such placement, the tabs 6032 are released, allowing the device 6010 to return to its original position to extend circumferentially around and clamp the vein against the flow connector with the tabs 6030 engaging the protrusions on the conduit portion of the flow connector 100c, thereby securely retaining the vein. The tabs 6018 of device 6010 remain external of the artery B, resting on the outer surface of the arterial wall. A suture 6040 is then applied through the vessel wall, interweaving between the tabs 6018, i.e., the suture extends over one tab 6018 and into the vessel wall and then out from the vessel wall and over the next tab 6018, etc., to secure the retention device 6010 to the artery B, thereby maintaining the flow connector 100c in position and maintaining a secure fluid connection between the artery B and vein V.

The method of implanting the flow connector, attaching the retention device and attaching the vein are described above. It should be appreciated that the retention devices and flow connector can be removed and placed at an alternate location one or multiple times if the user is not satisfied with the original placement. This can be achieved by removal of the retention devices and compression of the flow connector. In certain instances, it might be desirable to remove the flow connector and retention device altogether from the body. This can also be achieved by removing the retention device and compressing the flow connector to reduce its profile for withdrawal from the body. In the embodiments where the retention device includes two interlocking components, the components can be unlocked and separated to a non-interlocked position, and then re-interlocked if desired. This locking/unlocking can be repeated multiple times if necessary.

The retention devices disclosed herein can be used with any of the flow connectors described above. Additionally, the retention devices disclosed herein could have structure to engage the protrusions, recesses, or other irregular outer structure of the flow connectors of FIGS. 11A-11Q.

The retention devices described herein can be packaged as a kit with one or more of the flow connectors. However, it is also contemplated that the retention devices can be packaged as a separate unit for utilization with any of the foregoing flow connectors as well as for utilization with other flow connectors or other implants. Still further, in some embodiments, the retention devices described herein can be used itself to couple first and second body spaces without the aforedescribed flow connectors. In these embodiments, the retention device would engage, both the first and second body spaces in the various manners discussed above, such as for example by penetrating members penetrating the wall of the body spaces, to enable fluid coupling of the body spaces or to otherwise join these two body spaces. To enable fluid coupling, in some embodiments, the flow connector can include a non-porous material positioned internal and/or external of the retention device.

It is to be understood that although embodiments of the present invention have been largely described as being used to connect two tissue-enclosed body spaces, for example veins and arteries, other embodiments of the present invention may be used to connect a body space to an artificial device, such as a pump, an artificial conduit connected to the flow connector 100 conduit, sensors, plugs, among others.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents. All patents and publications discussed herein are incorporated in their entirety by reference thereto.

The invention claimed is:

1. A method of implanting and securing an implantable flow connector in a body of a patient for providing communication of a first space within the body of the patient with a second space within the body of the patient, the method comprising:
providing a manufactured flow connector having a longitudinally extending wall forming a conduit having a longitudinally extending lumen within the longitudinally extending wall, the lumen having a first orifice at a first end portion of the conduit and a second orifice at a second end portion of the conduit;
inserting a first retention device through a side opening formed in a wall of the first space within the body;
inserting the flow connector into the first retention device; and
positioning an end opening of the second space within the body external of the flow connector such that the flow connector provides fluid communication in an end to side connection of the first space within the body and the second space within the body.

2. The method of claim 1, further comprising the step of providing a second retention device external of the conduit of the flow connector.

3. The method of claim 1, wherein the method of implanting and securing the flow connector provides a sutureless connection of the first and second spaces within the body.

4. The method of claim 3, further comprising the step of interlocking the first retention device with the second retention device.

5. The method of claim 4, further including the step of positioning the first retention device within the second retention device.

6. The method of claim 1, further including the step of positioning a ring external of the conduit of the flow connector.

7. The method of claim 1, wherein the first retention device comprises at least one hook, and the step of inserting the first retention device comprises inserting the at least one hook through the side opening.

8. A method of implanting and securing an implantable flow connector in a body of a patient for providing communication of a first space within the body of the patient with a second space within the body of the patient, the method comprising:
providing a manufactured flow connector having a longitudinally extending wall forming a conduit having a longitudinally extending lumen within the longitudinally extending wall, the lumen having a first orifice at a first end portion of the conduit and a second orifice at a second end portion of the conduit;
inserting a first retention device separate from the flow connector through a side opening formed in a wall of the first space within the body;
inserting the flow connector through the side opening formed in the wall of the first space within the body; and
positioning an end opening of the second space within the body external of the flow connector such that the flow connector provides fluid communication in an end to side connection of the first space within the body and the second space within the body.

9. The method of claim 8, further comprising the step of providing a second retention device external of the conduit of the flow connector.

10. The method of claim 8, wherein the method of implanting and securing the flow connector provides a sutureless connection of the first and second spaces within the body.

11. The method of claim 10, further comprising the step of interlocking the first retention device with the second retention device.

12. The method of claim 11, further including the step of positioning the first retention device within the second retention device.

13. The method of claim 8, further including the step of positioning a ring external of the conduit of the flow connector.

14. The method of claim 8, wherein the first retention device comprises at least one hook, and the step of inserting the first retention device comprises inserting the at least one hook through the side opening.

15. A method of implanting and securing an implantable flow connector in a body of a patient for providing communication of a first space within the body of the patient with a second space within the body of the patient, the method comprising:
providing a manufactured flow connector having a longitudinally extending wall forming a conduit having a longitudinally extending lumen within the longitudinally extending wall, the lumen having a first orifice at a first end portion of the conduit and a second orifice at a second end portion of the conduit;
attaching a first retention device to a wall of the first space within the body;
inserting the flow connector through the side opening formed in the wall of the first space within the body; and
positioning an end opening of the second space within the body external of the flow connector such that the flow connector provides fluid communication in an end to side connection of the first space within the body and the second space within the body.

16. The method of claim 15, further comprising the step of providing a second retention device external of the conduit of the flow connector.

17. The method of claim 16, further comprising the step of interlocking the first retention device with the second retention device.

18. The method of claim 17, wherein the first retention device is positionable within the second retention device.

19. The method of claim 15, further including the step of positioning a ring external of the conduit of the flow connector.

20. The method of claim 15, wherein the first retention device comprises at least one hook, and the step of attaching the first retention device comprises passing the at least one hook through the wall.

* * * * *